(12) United States Patent
Hogard et al.

(10) Patent No.: US 12,201,762 B2
(45) Date of Patent: Jan. 21, 2025

(54) DIALYSIS SYSTEM AND METHODS

(71) Applicant: OUTSET MEDICAL, INC., San Jose, CA (US)

(72) Inventors: Michael Edward Hogard, Odessa, FL (US); Dean Hu, San Leandro, CA (US); Shih-Paul Chen, Los Altos, CA (US); James Ritson, San Jose, CA (US); Gopi K. Lingam, San Jose, CA (US); Peter Velasco Obico, Santa Clara, CA (US); James R. Curtis, Portland, OR (US); Steven M. Miller, Palo Alto, CA (US)

(73) Assignee: OUTSET MEDICAL, INC., San Jose, CA (US)

( * ) Notice: Subject to any disclaimer, the term of this patent is extended or adjusted under 35 U.S.C. 154(b) by 838 days.

(21) Appl. No.: 16/550,042

(22) Filed: Aug. 23, 2019

(65) Prior Publication Data

US 2020/0061273 A1  Feb. 27, 2020

Related U.S. Application Data

(60) Provisional application No. 62/722,119, filed on Aug. 23, 2018.

(51) Int. Cl.
*A61M 1/00* (2006.01)
*A61M 1/16* (2006.01)
(Continued)

(52) U.S. Cl.
CPC .......... *A61M 1/288* (2014.02); *A61M 1/1656* (2013.01); *A61M 1/1696* (2013.01);
(Continued)

(58) Field of Classification Search
CPC ................ A61M 1/288; A61M 1/1656; A61M 1/1696; A61M 1/1601; A61M 1/1621;
(Continued)

(56) References Cited

U.S. PATENT DOCUMENTS

| 1,662,870 A | 3/1928 | Stancliffe |
| 3,356,360 A | 12/1967 | Ward |

(Continued)

FOREIGN PATENT DOCUMENTS

| CA | 2297271 C | 8/2008 |
| CA | 2887068 A1 | 4/2014 |

(Continued)

OTHER PUBLICATIONS

Allis et al., "Chapter 16: Nanostructural Architectures from Molecular Building Blocks," in Handbook of Nanoscience, Engineering, and Technology, 1st Edition (Electrical Engineering Handbook), CRC Press LLC, Boca Raton, FL, Chapter 16 (70 pgs.), Oct. 2002.
Anglés et al., "Plasticized starch/Tunicin Whiskers Nanocomposite Materials. 2. Mechanical behavior," Macromolecules, 34, pp. 2921-2931, Mar. 2001.

(Continued)

*Primary Examiner* — T. Bennett McKenzie
(74) *Attorney, Agent, or Firm* — Shay Glenn LLP

(57) ABSTRACT

Dialysis systems and methods are described which can include a number of features. The dialysis systems described can be to provide dialysis therapy to a patient in the comfort of their own home. The dialysis system can be configured to prepare purified water from a tap water source in real-time that is used for creating a dialysate solution. The dialysis systems described also include features that make it easy for a patient to self-administer therapy. For example, the dialysis systems include disposable cartridge and patient tubing sets that are easily installed on the dialysis system and automatically align the tubing set, sensors, venous drip chamber, and other features with the corresponding components on the dialysis system. Methods of use are also (Continued)

provided, including automated priming sequences, blood return sequences, and dynamic balancing methods for controlling a rate of fluid transfer during different types of dialysis, including hemodialysis, ultrafiltration, and hemodiafiltration.

5 Claims, 33 Drawing Sheets

(51) Int. Cl.
    *A61M 1/28*         (2006.01)
    *A61M 1/36*         (2006.01)

(52) U.S. Cl.
    CPC .... *A61M 1/36222* (2022.05); *A61M 1/36225* (2022.05); *A61M 1/362262* (2022.05); *A61M 1/1601* (2014.02); *A61M 1/1621* (2014.02); *A61M 2205/3331* (2013.01)

(58) Field of Classification Search
    CPC .............. A61M 1/3624; A61M 1/3638; A61M 1/3649; A61M 1/36; A61M 2202/0413; A61M 2202/07; A61M 2202/3306; A61M 2202/3375; A61M 2202/3317; A61M 2205/3331; B01D 19/00; B01D 19/0063
    USPC ................................................. 95/24; 96/157
    See application file for complete search history.

(56) References Cited

U.S. PATENT DOCUMENTS

| | | |
|---|---|---|
| 3,695,445 A | 10/1972 | Esmond |
| 3,710,237 A | 1/1973 | Watson et al. |
| 3,762,032 A | 10/1973 | Bowling et al. |
| 3,809,309 A | 5/1974 | Batista |
| 3,827,563 A | 8/1974 | Boe et al. |
| 3,965,008 A | 6/1976 | Dawson |
| 4,080,295 A | 3/1978 | Riede |
| 4,089,456 A | 5/1978 | Toppen et al. |
| 4,100,068 A | 7/1978 | Jordan et al. |
| 4,110,220 A | 8/1978 | Lavender |
| 4,115,273 A | 9/1978 | Winstead |
| 4,155,157 A | 5/1979 | Gersbacher |
| 4,172,033 A | 10/1979 | Willock |
| 4,194,014 A | 3/1980 | Hermans et al. |
| 4,204,628 A | 5/1980 | Houston et al. |
| 4,209,391 A | 6/1980 | Lipps |
| 4,229,299 A | 10/1980 | Savitz et al. |
| 4,231,366 A | 11/1980 | Schael |
| 4,267,040 A | 5/1981 | Schal |
| 4,293,409 A | 10/1981 | Riede et al. |
| 4,310,416 A | 1/1982 | Tanaka et al. |
| 4,317,725 A | 3/1982 | Kume et al. |
| 4,342,651 A | 8/1982 | Ahrens |
| 4,476,022 A | 10/1984 | Doll |
| 4,486,303 A | 12/1984 | Brous |
| 4,500,426 A | 2/1985 | Ishii et al. |
| 4,508,622 A | 4/1985 | Polaschegg |
| 4,536,201 A | 8/1985 | Brorsson et al. |
| 4,560,472 A | 12/1985 | Granzow et al. |
| 4,624,784 A | 11/1986 | Lefebvre |
| 4,647,748 A | 3/1987 | Glassman |
| 4,661,246 A | 4/1987 | Ash |
| 4,689,108 A | 8/1987 | Barry, Jr. et al. |
| 4,756,835 A | 7/1988 | Wilson |
| 4,769,134 A | 9/1988 | Allan et al. |
| 4,770,787 A | 9/1988 | Heath et al. |
| 4,773,991 A | 9/1988 | Aid |
| 4,786,411 A | 11/1988 | Benattar et al. |
| 4,827,430 A | 5/1989 | Aid et al. |
| 4,869,421 A | 9/1989 | Norris et al. |
| 4,875,619 A | 10/1989 | Anderson et al. |
| 4,889,635 A | 12/1989 | Chevallet |
| 4,894,164 A | 1/1990 | Polaschegg |
| 4,923,613 A | 5/1990 | Chevallet |
| 5,087,930 A | 2/1992 | Roy et al. |
| 5,092,836 A | 3/1992 | Polaschegg |
| 5,094,749 A | 3/1992 | Seita et al. |
| 5,147,605 A | 9/1992 | Tatsuno et al. |
| 5,227,049 A | 7/1993 | Chevallet et al. |
| 5,232,145 A | 8/1993 | Alley et al. |
| 5,236,476 A | 8/1993 | Klick |
| 5,247,434 A | 9/1993 | Peterson et al. |
| 5,259,961 A | 11/1993 | Eigendorf |
| 5,312,550 A | 5/1994 | Hester |
| 5,313,023 A | 5/1994 | Johnson |
| 5,316,676 A | 5/1994 | Drori |
| 5,326,476 A | 7/1994 | Grogan et al. |
| 5,336,165 A | 8/1994 | Twardowski |
| 5,342,326 A | 8/1994 | Peppel et al. |
| 5,344,392 A | 9/1994 | Senninger et al. |
| 5,346,472 A | 9/1994 | Keshaviah et al. |
| 5,360,395 A | 11/1994 | Utterberg |
| 5,385,623 A | 1/1995 | Diaz |
| 5,394,732 A | 3/1995 | Johnson et al. |
| 5,395,351 A | 3/1995 | Munsch |
| 5,401,238 A | 3/1995 | Pirazzoli |
| 5,409,612 A | 4/1995 | Maltais et al. |
| 5,421,208 A | 6/1995 | Packard et al. |
| 5,439,451 A | 8/1995 | Collinson et al. |
| 5,469,264 A | 11/1995 | Shigemori |
| 5,472,614 A | 12/1995 | Rossi |
| 5,489,385 A | 2/1996 | Raabe et al. |
| 5,498,253 A | 3/1996 | Aswad et al. |
| 5,498,338 A | 3/1996 | Kruger et al. |
| 5,503,624 A | 4/1996 | Roeher et al. |
| 5,520,640 A | 5/1996 | Utterberg |
| 5,526,357 A | 6/1996 | Jandrell |
| 5,533,996 A | 7/1996 | Murphey et al. |
| 5,534,328 A | 7/1996 | Ashmead et al. |
| 5,536,258 A | 7/1996 | Folden |
| 5,580,460 A | 12/1996 | Polaschegg |
| 5,580,523 A | 12/1996 | Bard |
| 5,582,600 A | 12/1996 | Loh |
| 5,591,016 A | 1/1997 | Kubota et al. |
| 5,591,344 A | 1/1997 | Kenley et al. |
| 5,593,581 A | 1/1997 | Lescoche |
| 5,595,712 A | 1/1997 | Harbster et al. |
| 5,609,770 A | 3/1997 | Zimmerman et al. |
| 5,610,645 A | 3/1997 | Moore et al. |
| 5,611,214 A | 3/1997 | Wegeng et al. |
| 5,613,663 A | 3/1997 | Schmidt et al. |
| 5,615,996 A | 4/1997 | Suzuki et al. |
| 5,618,268 A | 4/1997 | Raines et al. |
| 5,618,441 A | 4/1997 | Rosa et al. |
| 5,620,608 A | 4/1997 | Rosa et al. |
| 5,623,969 A | 4/1997 | Raines |
| 5,624,572 A | 4/1997 | Larson et al. |
| 5,629,871 A | 5/1997 | Love et al. |
| 5,630,804 A | 5/1997 | Imada et al. |
| 5,643,190 A | 7/1997 | Utterberg |
| 5,647,984 A | 7/1997 | Hovland et al. |
| 5,648,684 A | 7/1997 | Bertin et al. |
| 5,650,071 A | 7/1997 | Brugger et al. |
| 5,662,144 A | 9/1997 | Lo et al. |
| 5,685,835 A | 11/1997 | Brugger |
| 5,689,966 A | 11/1997 | Zess et al. |
| 5,693,008 A | 12/1997 | Brugger et al. |
| 5,698,916 A | 12/1997 | Eguchi |
| 5,711,883 A | 1/1998 | Folden et al. |
| 5,713,850 A | 2/1998 | Heilmann et al. |
| 5,725,773 A | 3/1998 | Polaschegg |
| 5,743,892 A | 4/1998 | Loh et al. |
| 5,744,031 A | 4/1998 | Bene |
| 5,749,226 A | 5/1998 | Bowman et al. |
| 5,769,985 A | 6/1998 | Kawakami et al. |
| 5,779,833 A | 7/1998 | Cawley et al. |
| 5,782,575 A | 7/1998 | Vincent et al. |
| 5,788,099 A | 8/1998 | Treu et al. |
| 5,788,851 A | 8/1998 | Kenley et al. |
| 5,792,367 A | 8/1998 | Mattisson et al. |
| 5,811,062 A | 9/1998 | Wegeng et al. |

(56) References Cited

U.S. PATENT DOCUMENTS

| | | |
|---|---|---|
| 5,813,235 A | 9/1998 | Peterson |
| 5,851,202 A | 12/1998 | Carlsson |
| 5,858,238 A | 1/1999 | Mcrea et al. |
| 5,858,239 A | 1/1999 | Kenley et al. |
| 5,861,555 A | 1/1999 | Hobro et al. |
| 5,868,930 A | 2/1999 | Kopf |
| 5,879,316 A | 3/1999 | Safar et al. |
| 5,881,774 A | 3/1999 | Utterberg |
| 5,885,456 A | 3/1999 | Charkoudian et al. |
| 5,895,368 A | 4/1999 | Utterberg |
| 5,903,211 A | 5/1999 | Flego et al. |
| 5,910,138 A | 6/1999 | Sperko et al. |
| 5,914,033 A | 6/1999 | Carlsson |
| 5,921,678 A | 7/1999 | Desai et al. |
| 5,928,177 A | 7/1999 | Brugger et al. |
| 5,928,180 A | 7/1999 | Krivitski et al. |
| 5,932,103 A | 8/1999 | Kenley et al. |
| 5,932,940 A | 8/1999 | Epstein et al. |
| 5,938,634 A | 8/1999 | Packard |
| 5,938,938 A | 8/1999 | Bosetto et al. |
| 5,951,863 A | 9/1999 | Kruger et al. |
| 5,951,870 A | 9/1999 | Utterberg |
| 5,957,898 A | 9/1999 | Jepson et al. |
| 5,974,867 A | 11/1999 | Forster et al. |
| 5,976,115 A | 11/1999 | Parris et al. |
| 5,983,947 A | 11/1999 | Utterberg |
| 5,984,903 A | 11/1999 | Nadal |
| 5,993,174 A | 11/1999 | Konishi |
| 6,003,556 A | 12/1999 | Brugger et al. |
| 6,010,623 A | 1/2000 | Schnell et al. |
| 6,024,276 A | 2/2000 | Hirata et al. |
| 6,032,926 A | 3/2000 | Fuchs |
| 6,036,680 A | 3/2000 | Horne et al. |
| 6,039,877 A | 3/2000 | Chevallet et al. |
| 6,041,801 A | 3/2000 | Gray et al. |
| 6,044,691 A | 4/2000 | Kenley et al. |
| 6,048,432 A | 4/2000 | Ecer |
| 6,058,934 A | 5/2000 | Sullivan |
| 6,064,797 A | 5/2000 | Crittendon et al. |
| 6,066,261 A | 5/2000 | Spickermann |
| 6,071,269 A | 6/2000 | Schnell et al. |
| 6,074,559 A | 6/2000 | Hahmann et al. |
| 6,077,443 A | 6/2000 | Goldau |
| 6,082,891 A | 7/2000 | Schubert et al. |
| 6,100,463 A | 8/2000 | Ladd et al. |
| 6,109,994 A | 8/2000 | Cho et al. |
| 6,113,785 A | 9/2000 | Miura et al. |
| 6,117,115 A | 9/2000 | Hill et al. |
| 6,117,123 A | 9/2000 | Barney et al. |
| 6,121,539 A | 9/2000 | Johnson et al. |
| 6,123,798 A | 9/2000 | Gandhi et al. |
| 6,126,723 A | 10/2000 | Drost et al. |
| 6,126,831 A | 10/2000 | Goldau et al. |
| 6,129,973 A | 10/2000 | Martin et al. |
| 6,132,616 A | 10/2000 | Twardowski et al. |
| 6,139,754 A | 10/2000 | Hartranft et al. |
| 6,142,008 A | 11/2000 | Cole et al. |
| 6,143,181 A | 11/2000 | Falkvall et al. |
| 6,143,247 A | 11/2000 | Sheppard et al. |
| 6,148,635 A | 11/2000 | Beebe et al. |
| 6,153,102 A | 11/2000 | Kenley et al. |
| 6,165,149 A | 12/2000 | Utterberg et al. |
| 6,165,161 A | 12/2000 | York et al. |
| 6,167,910 B1 | 1/2001 | Chow |
| 6,187,198 B1 | 2/2001 | Utterberg |
| 6,187,199 B1 | 2/2001 | Goldau |
| 6,192,596 B1 | 2/2001 | Bennett et al. |
| 6,193,462 B1 | 2/2001 | Kubota |
| 6,202,312 B1 | 3/2001 | Rando |
| 6,203,522 B1 | 3/2001 | Holmberg et al. |
| 6,203,535 B1 | 3/2001 | Barney et al. |
| 6,212,333 B1 | 4/2001 | Olk et al. |
| 6,220,299 B1 | 4/2001 | Arvidsson et al. |
| 6,221,040 B1 | 4/2001 | Kleinekofort |
| 6,221,064 B1 | 4/2001 | Nadal |
| 6,223,130 B1 | 4/2001 | Gray et al. |
| 6,225,497 B1 | 5/2001 | Becker et al. |
| 6,234,773 B1 | 5/2001 | Hill et al. |
| 6,251,279 B1 | 6/2001 | Peterson et al. |
| 6,254,567 B1 | 7/2001 | Treu et al. |
| 6,254,754 B1 | 7/2001 | Ross et al. |
| 6,258,276 B1 | 7/2001 | Mika et al. |
| 6,261,282 B1 | 7/2001 | Jepson et al. |
| 6,277,277 B1 | 8/2001 | Jacobi et al. |
| 6,280,406 B1 | 8/2001 | Dolecek et al. |
| 6,284,141 B1 | 9/2001 | Shaldon et al. |
| 6,302,653 B1 | 10/2001 | Bryant et al. |
| 6,308,721 B1 | 10/2001 | Bock et al. |
| 6,309,673 B1 | 10/2001 | Duponchelle et al. |
| 6,322,551 B1 | 11/2001 | Brugger |
| 6,323,662 B2 | 11/2001 | Ferri |
| 6,325,774 B1 | 12/2001 | Bene et al. |
| 6,329,139 B1 | 12/2001 | Nova et al. |
| 6,331,252 B1 | 12/2001 | El Sayyid et al. |
| 6,334,301 B1 | 1/2002 | Otsap et al. |
| 6,343,614 B1 | 2/2002 | Gray et al. |
| 6,344,033 B1 | 2/2002 | Jepson et al. |
| 6,346,084 B1 | 2/2002 | Schnell et al. |
| 6,347,711 B1 | 2/2002 | Goebel et al. |
| 6,349,170 B1 | 2/2002 | Fressinet et al. |
| 6,350,260 B1 | 2/2002 | Goebel et al. |
| 6,355,161 B1 | 3/2002 | Shah et al. |
| 6,357,332 B1 | 3/2002 | Vecchio |
| 6,365,041 B1 | 4/2002 | Hoadley |
| 6,368,505 B1 | 4/2002 | Grummert et al. |
| 6,375,871 B1 | 4/2002 | Bentsen et al. |
| 6,382,923 B1 | 5/2002 | Gray |
| 6,387,069 B1 | 5/2002 | Utterberg |
| 6,395,180 B2 | 5/2002 | Chioini et al. |
| 6,415,860 B1 | 7/2002 | Kelly et al. |
| 6,416,293 B1 | 7/2002 | Bouchard et al. |
| 6,423,022 B1 | 7/2002 | Roeher et al. |
| 6,432,309 B1 | 8/2002 | Fuke et al. |
| 6,454,736 B1 | 9/2002 | Ludt et al. |
| 6,454,942 B1 | 9/2002 | Shintani et al. |
| 6,468,056 B1 | 10/2002 | Murakoshi |
| 6,477,058 B1 | 11/2002 | Luebs et al. |
| 6,481,982 B1 | 11/2002 | Yokomichi |
| 6,485,263 B1 | 11/2002 | Bryant et al. |
| 6,488,842 B2 | 12/2002 | Nagaoka |
| 6,488,872 B1 | 12/2002 | Beebe et al. |
| 6,503,062 B1 | 1/2003 | Gray et al. |
| 6,514,225 B1 | 2/2003 | Utterberg et al. |
| 6,514,412 B1 | 2/2003 | Insley et al. |
| 6,526,357 B1 | 2/2003 | Soussan et al. |
| 6,527,728 B2 | 3/2003 | Zhang |
| 6,530,262 B1 | 3/2003 | Esser |
| 6,536,742 B2 | 3/2003 | Lotz et al. |
| 6,537,506 B1 | 3/2003 | Schwalbe et al. |
| 6,544,229 B1 | 4/2003 | Danby et al. |
| 6,546,998 B2 | 4/2003 | Oh et al. |
| 6,554,789 B1 | 4/2003 | Brugger et al. |
| 6,572,576 B2 | 6/2003 | Brugger et al. |
| 6,572,641 B2 | 6/2003 | Brugger et al. |
| 6,575,927 B1 | 6/2003 | Weitzel et al. |
| 6,579,241 B2 | 6/2003 | Roeher |
| 6,579,253 B1 | 6/2003 | Burbank et al. |
| 6,581,906 B2 | 6/2003 | Pott et al. |
| 6,582,385 B2 | 6/2003 | Burbank et al. |
| 6,592,558 B2 | 7/2003 | Quah |
| 6,601,432 B1 | 8/2003 | Ericson et al. |
| 6,602,424 B1 | 8/2003 | Krämer et al. |
| 6,604,908 B1 | 8/2003 | Bryant et al. |
| 6,607,644 B1 | 8/2003 | Apffel, Jr. |
| 6,607,697 B1 | 8/2003 | Müller |
| 6,616,877 B2 | 9/2003 | Close et al. |
| 6,616,909 B1 | 9/2003 | Tonkovich et al. |
| 6,623,860 B2 | 9/2003 | Hu et al. |
| 6,630,068 B1 | 10/2003 | Vinci |
| 6,635,226 B1 | 10/2003 | Tso et al. |
| 6,640,611 B2 | 11/2003 | Ericson et al. |
| 6,649,046 B2 | 11/2003 | Chevallet |
| 6,649,063 B2 | 11/2003 | Brugger et al. |
| 6,652,627 B1 | 11/2003 | Tonkovich et al. |

(56) References Cited

U.S. PATENT DOCUMENTS

| | | |
|---|---|---|
| 6,653,841 B1 | 11/2003 | Koerdt et al. |
| 6,654,660 B1 | 11/2003 | Singh et al. |
| 6,666,840 B1 | 12/2003 | Falkvall et al. |
| 6,666,909 B1 | 12/2003 | Tegrotenhuis et al. |
| 6,672,502 B1 | 1/2004 | Paul et al. |
| 6,673,311 B1 | 1/2004 | Sotoyama et al. |
| 6,676,621 B1 | 1/2004 | Menninger |
| 6,676,835 B2 | 1/2004 | O'Connor et al. |
| 6,684,710 B2 | 2/2004 | Chevallet et al. |
| 6,685,831 B2 | 2/2004 | Dönig et al. |
| 6,686,946 B2 | 2/2004 | Masuda et al. |
| 6,688,381 B2 | 2/2004 | Pence et al. |
| 6,695,807 B2 | 2/2004 | Bell et al. |
| 6,716,356 B2 | 4/2004 | Collins et al. |
| 6,730,233 B2 | 5/2004 | Pedrazzi |
| 6,731,216 B2 | 5/2004 | Ho et al. |
| 6,733,676 B2 | 5/2004 | Takai |
| 6,736,789 B1 | 5/2004 | Spickermann |
| 6,738,052 B1 | 5/2004 | Manke et al. |
| 6,743,193 B2 | 6/2004 | Brugger et al. |
| 6,744,038 B2 | 6/2004 | Wang et al. |
| 6,746,514 B2 | 6/2004 | Bedingfield et al. |
| 6,749,814 B1 | 6/2004 | Bergh et al. |
| 6,767,333 B1 | 7/2004 | Müller et al. |
| 6,775,577 B2 | 8/2004 | Crnkovich et al. |
| 6,793,831 B1 | 9/2004 | Paul et al. |
| 6,797,056 B2 | 9/2004 | David |
| 6,804,991 B2 | 10/2004 | Balschat et al. |
| 6,806,947 B1 | 10/2004 | Ekdahl et al. |
| 6,811,707 B2 | 11/2004 | Rovatti et al. |
| 6,814,547 B2 | 11/2004 | Childers et al. |
| 6,814,726 B1 | 11/2004 | Lauer |
| 6,814,859 B2 | 11/2004 | Koehler et al. |
| 6,818,179 B1 | 11/2004 | Edgson et al. |
| 6,821,432 B2 | 11/2004 | Metzner |
| 6,827,698 B1 | 12/2004 | Kleinekofort |
| 6,830,693 B2 | 12/2004 | Govoni et al. |
| 6,838,156 B1 | 1/2005 | Neyer et al. |
| 6,852,231 B2 | 2/2005 | Ivansons et al. |
| 6,858,137 B2 | 2/2005 | Hahmann et al. |
| 6,863,867 B2 | 3/2005 | Vanden Bussche et al. |
| 6,868,309 B1 | 3/2005 | Begelman |
| 6,869,538 B2 | 3/2005 | Yu et al. |
| 6,871,838 B2 | 3/2005 | Raines et al. |
| 6,877,713 B1 | 4/2005 | Gray et al. |
| 6,878,283 B2 | 4/2005 | Thompson |
| 6,880,034 B2 | 4/2005 | Manke et al. |
| 6,881,344 B2 | 4/2005 | Vasta et al. |
| 6,889,556 B2 | 5/2005 | Steger |
| 6,892,781 B2 | 5/2005 | Mcherron et al. |
| 6,903,332 B2 | 6/2005 | Weiss et al. |
| 6,905,479 B1 | 6/2005 | Bouchard et al. |
| 6,911,262 B2 | 6/2005 | Sallavanti et al. |
| 6,913,877 B1 | 7/2005 | Chaplen et al. |
| 6,929,751 B2 | 8/2005 | Bowman, Jr. et al. |
| 6,936,031 B2 | 8/2005 | Caleffi |
| 6,939,111 B2 | 9/2005 | Huitt et al. |
| 6,939,471 B2 | 9/2005 | Gross et al. |
| 6,952,963 B2 | 10/2005 | Delnevo |
| 6,953,323 B2 | 10/2005 | Childers et al. |
| 6,955,655 B2 | 10/2005 | Burbank et al. |
| 6,967,002 B1 | 11/2005 | Edgson et al. |
| 6,974,301 B2 | 12/2005 | Suzuki et al. |
| 6,976,964 B2 | 12/2005 | Chevallet et al. |
| 6,979,309 B2 | 12/2005 | Burbank et al. |
| 6,981,522 B2 | 1/2006 | O'Connor et al. |
| 6,986,428 B2 | 1/2006 | Hester et al. |
| 6,989,134 B2 | 1/2006 | Tonkovich et al. |
| 6,994,829 B2 | 2/2006 | Whyatt et al. |
| 7,004,924 B1 | 2/2006 | Brugger et al. |
| 7,014,705 B2 | 3/2006 | David |
| 7,021,148 B2 | 4/2006 | Kuhn et al. |
| 7,022,098 B2 | 4/2006 | Wariar et al. |
| 7,029,456 B2 | 4/2006 | Ware et al. |
| 7,033,498 B2 | 4/2006 | Wong |
| 7,033,539 B2 | 4/2006 | Krensky et al. |
| 7,040,142 B2 | 5/2006 | Burbank |
| 7,044,432 B2 | 5/2006 | Beden et al. |
| 7,044,927 B2 | 5/2006 | Mueller et al. |
| 7,063,512 B2 | 6/2006 | Haesloop et al. |
| 7,070,589 B2 | 7/2006 | Lolachi et al. |
| 7,074,191 B2 | 7/2006 | Bosetto et al. |
| 7,087,033 B2 | 8/2006 | Brugger et al. |
| 7,087,036 B2 | 8/2006 | Busby et al. |
| 7,094,345 B2 | 8/2006 | Gilbert et al. |
| 7,112,273 B2 | 9/2006 | Weigel et al. |
| 7,114,701 B2 | 10/2006 | Peppel |
| 7,115,206 B2 | 10/2006 | Chevallet et al. |
| 7,115,228 B2 | 10/2006 | Lundtveit et al. |
| 7,118,920 B2 | 10/2006 | Brophy et al. |
| 7,121,815 B2 | 10/2006 | Knuth et al. |
| 7,122,149 B2 | 10/2006 | Li et al. |
| 7,122,156 B2 | 10/2006 | Bergh et al. |
| 7,125,540 B1 | 10/2006 | Wegeng et al. |
| 7,131,956 B1 | 11/2006 | Pirazzoli et al. |
| 7,147,615 B2 | 12/2006 | Wariar et al. |
| 7,150,815 B2 | 12/2006 | Ashmead et al. |
| 7,152,469 B2 | 12/2006 | Milleker et al. |
| 7,163,531 B2 | 1/2007 | Seese et al. |
| 7,166,084 B2 | 1/2007 | Utterberg |
| 7,168,334 B1 | 1/2007 | Drott |
| 7,170,591 B2 | 1/2007 | Ohishi et al. |
| 7,175,697 B2 | 2/2007 | Neri |
| 7,186,342 B2 | 3/2007 | Pirazzoli et al. |
| 7,188,151 B2 | 3/2007 | Kumar et al. |
| 7,211,442 B2 | 5/2007 | Gilbert et al. |
| 7,214,312 B2 | 5/2007 | Brugger et al. |
| 7,217,108 B2 | 5/2007 | Herwig et al. |
| 7,217,364 B2 | 5/2007 | Lauer et al. |
| 7,223,262 B2 | 5/2007 | Brehm et al. |
| 7,223,338 B2 | 5/2007 | Duchamp et al. |
| 7,232,418 B2 | 6/2007 | Neri et al. |
| 7,238,164 B2 | 7/2007 | Childers et al. |
| 7,247,146 B2 | 7/2007 | Tonelli et al. |
| 7,279,134 B2 | 10/2007 | Chan et al. |
| 7,291,123 B2 | 11/2007 | Baraldi et al. |
| 7,306,197 B2 | 12/2007 | Parrino et al. |
| 7,314,061 B2 | 1/2008 | Peppel |
| 7,316,780 B1 | 1/2008 | Fendya et al. |
| 7,337,674 B2 | 3/2008 | Burbank et al. |
| 7,341,568 B2 | 3/2008 | Zhang |
| 7,354,426 B2 | 4/2008 | Young |
| 7,355,685 B2 | 4/2008 | Scibona et al. |
| 7,378,280 B2 | 5/2008 | Quake et al. |
| 7,381,195 B2 | 6/2008 | Mori et al. |
| 7,393,337 B2 | 7/2008 | Tonelli et al. |
| 7,402,249 B2 | 7/2008 | Ikeda |
| 7,469,716 B2 | 12/2008 | Parrino et al. |
| 7,470,265 B2 | 12/2008 | Brugger et al. |
| 7,488,301 B2 | 2/2009 | Beden et al. |
| 7,488,447 B2 | 2/2009 | Sternby |
| 7,493,824 B2 | 2/2009 | Brucksch et al. |
| 7,494,590 B2 | 2/2009 | Felding et al. |
| 7,503,908 B2 | 3/2009 | Bartholomew |
| 7,507,380 B2 | 3/2009 | Chang et al. |
| 7,510,545 B2 | 3/2009 | Peppel |
| 7,517,332 B2 | 4/2009 | Tonelli et al. |
| 7,517,387 B2 | 4/2009 | Chevallet et al. |
| 7,520,919 B2 | 4/2009 | Caleffi |
| 7,537,687 B2 | 5/2009 | Toyoda et al. |
| 7,544,300 B2 | 6/2009 | Brugger et al. |
| 7,551,043 B2 | 6/2009 | Nguyen et al. |
| 7,559,911 B2 | 7/2009 | Giannella |
| 7,575,562 B2 | 8/2009 | Oishi et al. |
| 7,575,564 B2 | 8/2009 | Childers |
| 7,591,449 B2 | 9/2009 | Raines et al. |
| 7,603,907 B2 | 10/2009 | Reiter et al. |
| 7,615,035 B2 | 11/2009 | Peppel |
| 7,618,531 B2 | 11/2009 | Sugioka et al. |
| 7,622,043 B2 | 11/2009 | Sawada et al. |
| 7,632,470 B2 | 12/2009 | Tabata et al. |
| 7,647,834 B2 | 1/2010 | O'Mahony et al. |
| 7,648,474 B2 | 1/2010 | Paolini et al. |
| 7,648,476 B2 | 1/2010 | Bock et al. |

(56) References Cited

U.S. PATENT DOCUMENTS

| | | |
|---|---|---|
| 7,648,792 B2 | 1/2010 | Kaschmitter et al. |
| 7,656,527 B2 | 2/2010 | Scarpaci |
| 7,661,294 B2 | 2/2010 | Dam |
| 7,671,974 B2 | 3/2010 | O'Mahony et al. |
| 7,682,328 B2 | 3/2010 | Han et al. |
| 7,686,778 B2 | 3/2010 | Burbank et al. |
| 7,699,992 B2 | 4/2010 | Sternby |
| 7,708,714 B2 | 5/2010 | Connell et al. |
| 7,713,226 B2 | 5/2010 | Ash et al. |
| 7,726,361 B2 | 6/2010 | Bartholomew |
| 7,727,220 B2 | 6/2010 | Wieslander et al. |
| 7,744,553 B2 | 6/2010 | Kelly et al. |
| 7,749,184 B2 | 7/2010 | Cavalcanti et al. |
| 7,758,082 B2 | 7/2010 | Weigel et al. |
| 7,758,547 B2 | 7/2010 | Tonelli et al. |
| 7,771,379 B2 | 8/2010 | Treu |
| 7,771,380 B2 | 8/2010 | Jönsson et al. |
| 7,775,986 B2 | 8/2010 | Roeher et al. |
| 7,776,219 B2 | 8/2010 | Brugger et al. |
| 7,780,848 B2 | 8/2010 | Kim et al. |
| 7,788,038 B2 | 8/2010 | Oshita et al. |
| 7,790,029 B2 | 9/2010 | Dannenmaier et al. |
| 7,794,141 B2 | 9/2010 | Perry et al. |
| 7,794,419 B2 | 9/2010 | Paolini et al. |
| 7,801,746 B2 | 9/2010 | Moll et al. |
| 7,815,852 B2 | 10/2010 | Sternby |
| 7,824,354 B2 | 11/2010 | Vinci et al. |
| 7,871,390 B2 | 1/2011 | Rambod et al. |
| 7,873,489 B2 | 1/2011 | Dolgos et al. |
| 7,896,831 B2 | 3/2011 | Sternby et al. |
| 7,901,579 B2 | 3/2011 | Brugger et al. |
| 7,913,751 B2 | 3/2011 | Zwittig |
| 7,918,993 B2 | 4/2011 | Harraway |
| 7,922,899 B2 | 4/2011 | Vasta et al. |
| 7,955,504 B1 | 6/2011 | Jovanovic et al. |
| 7,968,250 B2 | 6/2011 | Kaschmitter et al. |
| 8,002,727 B2 | 8/2011 | Brugger et al. |
| 8,012,114 B2 | 9/2011 | Daniel et al. |
| 8,075,509 B2 | 12/2011 | Molducci et al. |
| 8,105,265 B2 | 1/2012 | Demers et al. |
| 8,105,266 B2 | 1/2012 | Childers et al. |
| 8,128,822 B2 | 3/2012 | Browning et al. |
| 8,137,554 B2 | 3/2012 | Jovanovic et al. |
| 8,182,440 B2 | 5/2012 | Cruz et al. |
| 8,182,691 B2 | 5/2012 | Stahl |
| 8,190,651 B2 | 5/2012 | Treu et al. |
| 8,192,387 B2 | 6/2012 | Brugger et al. |
| 8,210,049 B2 | 7/2012 | Brugger |
| 8,235,931 B2 | 8/2012 | Burbank et al. |
| 8,236,599 B2 | 8/2012 | Chang et al. |
| 8,267,881 B2 | 9/2012 | O'Mahony et al. |
| 8,273,245 B2 | 9/2012 | Jovanovic et al. |
| 8,293,113 B2 | 10/2012 | Jönsson et al. |
| 8,293,114 B2 | 10/2012 | Jönsson et al. |
| 8,298,427 B2 | 10/2012 | Ficheux et al. |
| 8,323,492 B2 | 12/2012 | Childers et al. |
| 8,329,030 B2 | 12/2012 | Childers et al. |
| 8,343,085 B2 | 1/2013 | Toyoda et al. |
| 8,394,046 B2 | 3/2013 | Nuernberger et al. |
| 8,414,182 B2 | 4/2013 | Paul et al. |
| 8,419,945 B2 | 4/2013 | Browning et al. |
| 8,449,487 B2 | 5/2013 | Hovland et al. |
| 8,460,228 B2 | 6/2013 | Burbank et al. |
| 8,475,398 B2 | 7/2013 | O'Mahony |
| 8,491,518 B2 | 7/2013 | Schnell et al. |
| 8,496,824 B2 | 7/2013 | Remkes et al. |
| 8,501,009 B2 | 8/2013 | Peterson et al. |
| 8,506,536 B2 | 8/2013 | Schnell |
| 8,512,553 B2 | 8/2013 | Cicchello et al. |
| 8,512,554 B2 | 8/2013 | Yu et al. |
| 8,524,086 B2 | 9/2013 | Peterson et al. |
| 8,529,491 B2 | 9/2013 | Beiriger |
| 8,535,525 B2 | 9/2013 | Heyes et al. |
| 8,603,020 B2 | 12/2013 | Roger et al. |
| 8,608,658 B2 | 12/2013 | Burbank et al. |
| 8,647,290 B2 | 2/2014 | Masala et al. |
| 8,679,348 B2 | 3/2014 | Burbank et al. |
| 8,685,244 B2 | 4/2014 | Heyes et al. |
| 8,685,251 B2 | 4/2014 | Smejtek et al. |
| 8,753,515 B2 | 6/2014 | Curtis et al. |
| 8,801,922 B2 | 8/2014 | Wrazel et al. |
| 8,840,581 B2 | 9/2014 | McGill et al. |
| 9,024,746 B2 | 5/2015 | Burbank et al. |
| 9,097,370 B2 | 8/2015 | Schnell et al. |
| 9,138,687 B2 | 9/2015 | Peterson et al. |
| 9,220,825 B2 | 12/2015 | Buckberry |
| 9,220,828 B2 | 12/2015 | Coates |
| 9,283,320 B2 | 3/2016 | Brugger et al. |
| 9,328,969 B2 | 5/2016 | Wrazel et al. |
| 9,402,945 B2 | 8/2016 | Hogard et al. |
| 9,480,455 B2 | 11/2016 | Buckberry |
| 9,482,218 B2 | 11/2016 | Coates et al. |
| 9,504,777 B2 | 11/2016 | Hogard et al. |
| 9,545,469 B2 | 1/2017 | Curtis et al. |
| 9,579,440 B2 | 2/2017 | Hogard et al. |
| 9,592,029 B2 | 3/2017 | Buckberry |
| 9,636,444 B2 | 5/2017 | Burbank et al. |
| 9,700,663 B2 | 7/2017 | Burbank et al. |
| 9,835,509 B2 | 12/2017 | Brugger et al. |
| 9,879,807 B2 | 1/2018 | Brugger et al. |
| 9,895,480 B2 | 2/2018 | Wrazel et al. |
| 10,105,476 B2 | 10/2018 | Peterson et al. |
| 2002/0023879 A1 | 2/2002 | Hadden |
| 2002/0032398 A1 | 3/2002 | Steele et al. |
| 2002/0108859 A1 | 8/2002 | Wang et al. |
| 2002/0108869 A1 | 8/2002 | Savtchenko |
| 2002/0115200 A1 | 8/2002 | Zou et al. |
| 2002/0162784 A1 | 11/2002 | Kohlheb et al. |
| 2002/0187069 A1 | 12/2002 | Levin et al. |
| 2003/0010717 A1 | 1/2003 | Brugger et al. |
| 2003/0039169 A1 | 2/2003 | Ehrfeld et al. |
| 2003/0052429 A1 | 3/2003 | Vigna et al. |
| 2003/0082066 A1 | 5/2003 | Hajaligol et al. |
| 2003/0138349 A1 | 7/2003 | Robinson et al. |
| 2003/0156991 A1 | 8/2003 | Halas et al. |
| 2003/0163077 A1 | 8/2003 | Kim et al. |
| 2003/0183345 A1 | 10/2003 | Soberay |
| 2003/0220598 A1 | 11/2003 | Busby et al. |
| 2004/0004589 A1 | 1/2004 | Shih |
| 2004/0008370 A1 | 1/2004 | Keane et al. |
| 2004/0012122 A1 | 1/2004 | Nagaoka et al. |
| 2004/0016700 A1 | 1/2004 | Kellam et al. |
| 2004/0020286 A1 | 2/2004 | Blakley et al. |
| 2004/0022691 A1 | 2/2004 | Allen et al. |
| 2004/0035452 A1 | 2/2004 | Ma |
| 2004/0035462 A1 | 2/2004 | McCarty et al. |
| 2004/0072278 A1 | 4/2004 | Chou et al. |
| 2004/0084370 A1 | 5/2004 | Singh et al. |
| 2004/0084371 A1 | 5/2004 | Kellam et al. |
| 2004/0086427 A1 | 5/2004 | Childers et al. |
| 2004/0125689 A1 | 7/2004 | Ehrfeld et al. |
| 2004/0157096 A1 | 8/2004 | Peterson |
| 2004/0158189 A1 | 8/2004 | Tonelli et al. |
| 2004/0208751 A1 | 10/2004 | Lazar et al. |
| 2004/0215129 A1 | 10/2004 | Edgson et al. |
| 2004/0256230 A1 | 12/2004 | Yager et al. |
| 2005/0006296 A1 | 1/2005 | Sullivan et al. |
| 2005/0007748 A1 | 1/2005 | Callahan et al. |
| 2005/0040110 A1 | 2/2005 | Felding |
| 2005/0070837 A1 | 3/2005 | Ferrarini et al. |
| 2005/0074834 A1 | 4/2005 | Chaplen et al. |
| 2005/0082225 A1 | 4/2005 | Kreymann |
| 2005/0126211 A1 | 6/2005 | Drost et al. |
| 2005/0129580 A1 | 6/2005 | Swinehart et al. |
| 2005/0131332 A1 | 6/2005 | Kelly et al. |
| 2005/0145497 A1 | 7/2005 | Gilbert et al. |
| 2005/0179748 A1 | 8/2005 | Malik et al. |
| 2005/0202557 A1 | 9/2005 | Borenstein et al. |
| 2006/0046113 A1 | 3/2006 | Wang et al. |
| 2006/0079698 A1 | 4/2006 | Joshi et al. |
| 2006/0157413 A1 | 7/2006 | Bene et al. |
| 2006/0174715 A1 | 8/2006 | Wehrs et al. |
| 2006/0200064 A1 | 9/2006 | Gross et al. |
| 2006/0266692 A1 | 11/2006 | Foster et al. |

(56) References Cited

U.S. PATENT DOCUMENTS

| | | |
|---|---|---|
| 2007/0020400 A1 | 1/2007 | Chang |
| 2007/0029365 A1 | 2/2007 | Paul et al. |
| 2007/0119771 A1 | 5/2007 | Schukar et al. |
| 2007/0125489 A1 | 6/2007 | Paul et al. |
| 2007/0128707 A1 | 6/2007 | Rorrer et al. |
| 2007/0131403 A1 | 6/2007 | Vetrovec et al. |
| 2007/0149914 A1 | 6/2007 | Axelsson et al. |
| 2007/0158249 A1 | 7/2007 | Ash |
| 2007/0158268 A1 | 7/2007 | Decomo |
| 2007/0184576 A1 | 8/2007 | Chang et al. |
| 2007/0215644 A1 | 9/2007 | Otis et al. |
| 2007/0243990 A1 | 10/2007 | Kolenbrander et al. |
| 2007/0278155 A1 | 12/2007 | Lo et al. |
| 2007/0295651 A1 | 12/2007 | Martinez et al. |
| 2008/0006040 A1 | 1/2008 | Peterson et al. |
| 2008/0009780 A1 | 1/2008 | Leonard et al. |
| 2008/0053842 A1 | 3/2008 | Williams et al. |
| 2008/0097274 A1 | 4/2008 | Neri et al. |
| 2008/0108122 A1 | 5/2008 | Paul et al. |
| 2008/0108930 A1 | 5/2008 | Weitzel et al. |
| 2008/0149563 A1 | 6/2008 | Ash |
| 2008/0196725 A1 | 8/2008 | Mele |
| 2008/0200858 A1 | 8/2008 | Ichiishi et al. |
| 2008/0296226 A1 | 12/2008 | Gotch |
| 2009/0008331 A1 | 1/2009 | Wilt et al. |
| 2009/0012452 A1 | 1/2009 | Slepicka et al. |
| 2009/0038393 A1 | 2/2009 | Chaung et al. |
| 2009/0076433 A1 | 3/2009 | Folden et al. |
| 2009/0087326 A1 | 4/2009 | Voltenburg et al. |
| 2009/0092526 A1 | 4/2009 | Miller |
| 2009/0095679 A1 | 4/2009 | Demers et al. |
| 2009/0101549 A1 | 4/2009 | Kamen et al. |
| 2009/0101576 A1 | 4/2009 | Rohde et al. |
| 2009/0114595 A1 | 5/2009 | Wallenas et al. |
| 2009/0124963 A1 | 5/2009 | Hogard et al. |
| 2009/0165366 A1 | 7/2009 | Jovanovic et al. |
| 2009/0211977 A1 | 8/2009 | Miller |
| 2009/0230036 A1 | 9/2009 | Apel et al. |
| 2009/0306573 A1 | 12/2009 | Gagner et al. |
| 2009/0309835 A1 | 12/2009 | Levin et al. |
| 2009/0312686 A1 | 12/2009 | Sakamoto et al. |
| 2010/0018923 A1 | 1/2010 | Rohde et al. |
| 2010/0022934 A1 | 1/2010 | Hogard |
| 2010/0051552 A1 | 3/2010 | Rohde et al. |
| 2010/0078385 A1 | 4/2010 | Kawarabata et al. |
| 2010/0089807 A1 | 4/2010 | Heyes et al. |
| 2010/0192686 A1 | 8/2010 | Kamen et al. |
| 2010/0271296 A1 | 10/2010 | Kopychev et al. |
| 2010/0292627 A1 | 11/2010 | Caleffi et al. |
| 2010/0292657 A1 | 11/2010 | Fontanazzi et al. |
| 2010/0292944 A1 | 11/2010 | Howell et al. |
| 2010/0321046 A1 | 12/2010 | Randall et al. |
| 2010/0326914 A1 | 12/2010 | Drost et al. |
| 2011/0005986 A1 | 1/2011 | Kelly et al. |
| 2011/0105979 A1 | 5/2011 | Schlaeper et al. |
| 2011/0106466 A1 | 5/2011 | Furmanski et al. |
| 2011/0132841 A1 | 6/2011 | Rohde et al. |
| 2011/0186517 A1 | 8/2011 | Hedmann et al. |
| 2011/0189048 A1 | 8/2011 | Curtis et al. |
| 2011/0257579 A1 | 10/2011 | Rossi et al. |
| 2011/0295175 A1 | 12/2011 | Felder et al. |
| 2012/0029937 A1 | 2/2012 | Neftel et al. |
| 2012/0065581 A1 | 3/2012 | Childers et al. |
| 2012/0103902 A1 | 5/2012 | Childers et al. |
| 2012/0138533 A1 | 6/2012 | Curtis et al. |
| 2012/0204968 A1 | 8/2012 | Fulkerson et al. |
| 2012/0226236 A1 | 9/2012 | Fini et al. |
| 2012/0267291 A1 | 10/2012 | Coates |
| 2012/0292246 A1 | 11/2012 | Jovanovic et al. |
| 2012/0298580 A1 | 11/2012 | Gronau et al. |
| 2012/0318740 A1 | 12/2012 | Ekdahl et al. |
| 2013/0018301 A1 | 1/2013 | Weaver et al. |
| 2013/0020237 A1 | 1/2013 | Wilt et al. |
| 2013/0030344 A1 | 1/2013 | Gronau et al. |
| 2013/0037485 A1 | 2/2013 | Wilt et al. |
| 2013/0056418 A1 | 3/2013 | Kopperschmidt et al. |
| 2013/0056419 A1 | 3/2013 | Curtis |
| 2013/0060233 A1 | 3/2013 | O'Connor et al. |
| 2013/0146541 A1 | 6/2013 | Weigel et al. |
| 2013/0180339 A1 | 7/2013 | Brugger |
| 2013/0186829 A1 | 7/2013 | Callan et al. |
| 2013/0206693 A2 | 8/2013 | Thys |
| 2013/0213890 A1 | 8/2013 | Kelly et al. |
| 2013/0267883 A1 | 10/2013 | Medrano |
| 2013/0303962 A1* | 11/2013 | Bernard ............... B01F 3/0865 604/6.09 |
| 2013/0303963 A1 | 11/2013 | Breuch et al. |
| 2014/0014580 A1 | 1/2014 | Ritter |
| 2014/0018727 A1 | 1/2014 | Burbank et al. |
| 2014/0021111 A1 | 1/2014 | Roger et al. |
| 2014/0069861 A1 | 3/2014 | Browning et al. |
| 2014/0072288 A1 | 3/2014 | Newell |
| 2014/0076058 A1 | 3/2014 | Brugger et al. |
| 2014/0158589 A1 | 6/2014 | Furuhashi et al. |
| 2014/0178215 A1 | 6/2014 | Baxter et al. |
| 2014/0209540 A1 | 7/2014 | Smejtek et al. |
| 2014/0276424 A1 | 9/2014 | Davis et al. |
| 2014/0291243 A1 | 10/2014 | Curtis et al. |
| 2014/0319035 A1 | 10/2014 | Burbank et al. |
| 2015/0005699 A1 | 1/2015 | Burbank et al. |
| 2015/0027951 A1 | 1/2015 | Wallace et al. |
| 2015/0041377 A1 | 2/2015 | Heyes |
| 2015/0076053 A1 | 3/2015 | Higgitt et al. |
| 2015/0129481 A1 | 5/2015 | Higgitt et al. |
| 2015/0196702 A1 | 7/2015 | Burbank et al. |
| 2015/0204733 A1 | 7/2015 | Newell et al. |
| 2015/0238676 A1 | 8/2015 | Giordano et al. |
| 2015/0252800 A1 | 9/2015 | Buckberry et al. |
| 2015/0267821 A1 | 9/2015 | Brugger et al. |
| 2015/0306294 A1 | 10/2015 | Jansson et al. |
| 2015/0314055 A1 | 11/2015 | Hogard et al. |
| 2015/0343128 A1 | 12/2015 | Hogard et al. |
| 2015/0343132 A1* | 12/2015 | Hogard ............... A61M 1/166 73/290 R |
| 2015/0343133 A1 | 12/2015 | Hogard et al. |
| 2015/0354906 A1 | 12/2015 | Miller |
| 2015/0359973 A1 | 12/2015 | Onken et al. |
| 2016/0051739 A1 | 2/2016 | Buckberry |
| 2016/0051743 A1 | 2/2016 | Buckberry |
| 2016/0082172 A1 | 3/2016 | Miller et al. |
| 2016/0084785 A1 | 3/2016 | Buckberry |
| 2016/0106906 A1 | 4/2016 | Buckberry |
| 2016/0199558 A1 | 7/2016 | Buckberry |
| 2016/0325034 A1 | 11/2016 | Wiktor et al. |
| 2017/0239411 A1 | 8/2017 | Lura et al. |
| 2017/0290970 A1 | 10/2017 | Friederichs et al. |
| 2017/0296727 A1 | 10/2017 | Burbank et al. |
| 2017/0296730 A1 | 10/2017 | Soto et al. |
| 2017/0312419 A1 | 11/2017 | Burbank et al. |
| 2017/0326285 A1 | 11/2017 | Hogard et al. |
| 2018/0071447 A1 | 3/2018 | Gronau et al. |
| 2018/0104400 A1 | 4/2018 | Burbank et al. |
| 2018/0126056 A1 | 5/2018 | Wrazel et al. |
| 2018/0128688 A1 | 5/2018 | Newell et al. |
| 2018/0128698 A1 | 5/2018 | Brugger et al. |
| 2019/0022293 A1 | 1/2019 | Peterson et al. |
| 2019/0192758 A1 | 6/2019 | Ritson et al. |
| 2019/0201604 A1 | 7/2019 | Hogard et al. |
| 2020/0033897 A1 | 1/2020 | Jensen et al. |
| 2021/0069401 A1 | 3/2021 | Peterson et al. |

FOREIGN PATENT DOCUMENTS

| | | |
|---|---|---|
| CA | 2930431 A1 | 5/2015 |
| CN | 200951223 Y | 9/2007 |
| DE | 8702995 U1 | 6/1987 |
| DE | 69217519 T2 | 6/1997 |
| EP | 0165751 A2 | 12/1985 |
| EP | 0324922 A2 | 7/1989 |
| EP | 0679100 A1 | 11/1995 |
| EP | 0796997 A1 | 9/1997 |
| EP | 0547025 B2 | 6/2002 |
| EP | 1892000 A1 | 2/2008 |
| EP | 1898000 A2 | 3/2008 |

(56) References Cited

FOREIGN PATENT DOCUMENTS

| | | |
|---|---|---|
| EP | 2319551 A2 | 5/2011 |
| EP | 2535067 A1 | 12/2012 |
| GB | 1289738 A | 9/1972 |
| JP | 59-58002 A | 4/1984 |
| JP | 60-143803 A | 7/1985 |
| JP | H4-35669 A | 2/1992 |
| JP | H11-33111 A | 2/1999 |
| JP | 2001510266 A | 7/2001 |
| JP | 2002143298 A | 5/2002 |
| JP | 2002527212 A | 8/2002 |
| JP | 2003508179 A | 3/2003 |
| JP | 2007167108 A | 7/2007 |
| JP | 2007268490 A | 10/2007 |
| JP | 2007529707 A | 10/2007 |
| JP | 2007327950 A | 12/2007 |
| JP | 2012152286 A | 8/2012 |
| JP | 55-14045 A | 6/2014 |
| JP | 2014531922 A | 12/2014 |
| JP | 2018524074 A | 8/2018 |
| WO | WO00/16916 A1 | 3/2000 |
| WO | WO00/25843 A1 | 5/2000 |
| WO | WO00/57935 A1 | 10/2000 |
| WO | WO02/40874 A1 | 5/2002 |
| WO | WO02/076529 A1 | 10/2002 |
| WO | WO03/076661 A1 | 9/2003 |
| WO | WO2006/011009 A2 | 2/2006 |
| WO | WO2006/039293 A2 | 4/2006 |
| WO | WO2007/073739 A1 | 7/2007 |
| WO | WO2007/089855 A2 | 8/2007 |
| WO | WO2008/027967 A1 | 3/2008 |
| WO | WO2008/106191 A2 | 9/2008 |
| WO | WO2010/027435 A1 | 3/2010 |
| WO | WO2010/062698 A2 | 6/2010 |
| WO | WO2010/085764 A2 | 7/2010 |
| WO | WO2010/146343 A2 | 12/2010 |
| WO | WO2013/031966 A1 | 3/2013 |
| WO | WO2014/117000 A2 | 7/2014 |
| WO | WO2014/124180 A2 | 8/2014 |
| WO | WO2014/160370 A1 | 10/2014 |
| WO | WO2015/150179 A1 | 10/2015 |
| WO | WO2015/173151 A1 | 11/2015 |
| WO | WO2015/185920 A1 | 12/2015 |
| WO | WO2016/030147 A1 | 3/2016 |
| WO | WO2016/049542 A2 | 3/2016 |
| WO | WO2016/057981 A1 | 4/2016 |
| WO | WO2016/057982 A1 | 4/2016 |
| WO | WO2016/130679 A2 | 9/2016 |
| WO | WO2017/072511 A1 | 5/2017 |
| WO | WO2018/035520 A1 | 2/2018 |
| WO | WO2020/223500 A1 | 11/2020 |

OTHER PUBLICATIONS

California Energy Commission; Development of Supported Polymeric Liquid Membrane Technology for Aqueous MTBE Mitigation, EPRI, Palo Alto, CA, California Energy Commission, Sacramento, CA: Doc. No. 1006577; 70 pgs.; Jul. 2002.
Demura et al., "Ductile Thin Foil of Ni3Al," Mechanical Properties of Structural Films, ASTM International Nov. 2000 Symposium (Orlando, FL), pp. 248-261, published Oct. 1, 2001.

Favier et al.; Nanocomposite materials from latex and cellulose whiskers; Polymers for Advanced Technologies; 6; pp. 351-355; Jan. 1995.
Federal Energy Technology Center, "Technology Development Through Industrial Partnerships," (Tech. Dev. Data Sheet), 12 pgs., Sep. 1998.
Grunert et al., "Progress in the Development of Cellulose Reinforced Nanocomposites," PMSE Preprints 2000, 82, 232, 2 pgs., Mar. 2000.
Haas, "Further development of MMW and SMMW platelet feed horn arrays," Astron. Soc. Pac. Conf. Ser., vol. 75, pp. 99-105, Multi-Feed Systems for Radio Telescopes, Workshop held in Tucson, Arizona, May 16-18, 1994.
Introtek International; Drip chamber liquid level sensor (sales literature); 2 pages; retrieved from the internet (http://www.introtek.com/PDFs/1/DDS-14.0_DripDetectSensor.pdf); © Jan. 1, 2009.
Koeneman et al., "Feasibility of Micro Power Supplies for MEMS," (pre-publication copy) J. MicroElectoMechanical Sys., 6(4), pp. 355-362, Dec. 1997.
Morin et al., "Nanocomposites of Chitin Whiskers from Riftia Tubes and Poly (caprolactone)," Macromolecules, vol. 35, pp. 2190-2199, Feb. 2002.
Nakamura et al., "Research on Pressure Welding Conditions of Various Work Metals (Effects of Contact Pressure, Surface Expansion Ratio and Temperature)," JSME International Journal, Series III 31(3), 612-617, Sep. 1988.
Nakao et al., "Diffusion Bonding of Intermetallic Compound TiAl," ISIJ International, 31(10), 1260-1266, Oct. 1991.
Oddy et al., "Electrokinetic Instability Micromixing," Anal. Chem., 73(24), pp. 5822-5832, Dec. 2001.
Omega Engineering Inc.; Load Cell (definition, information); 3 pgs; retrieved from the internet on Jun. 17, 2015 (http://www.omega.com/prodinfo/LoadCells.html).
Orts et al., "Effect of Fiber Source on Cellulose Reinforced Polymer Nanocomposites," ANTEC 2004: Conference Proceedings, 62nd Annual Tech. Conference; Chicago, IL, pp. 2427-2431, May 2004.
Paillet et al., "Chitin Whisker Reinforced Thermoplastic Nanocomposites," Macromolecules, vol. 34, No. 19, pp. 6527-6530, Sep. 2001.
Paul et al., "Microlamination for Microtechnology-based Energy, Chemical, and Biological Systems," ASME IMECE, ASE vol. 39, pp. 45-52, Nashville, Tennessee, Nov. 15-20, 1999.
Pluess, "Application of Controlled Thermal Expansion in Diffusion Bonding for the High-Volume Microlamination of MECS Devices," Thesis (MS), Oregon State University, 193 pgs., Sep. 2004.
Porter et al.; Cost drivers in microlamination based on a high volume production system design; ASME 2002 Conf. Proc.; New Orleans, Louisiana; pp. 267-274; Nov. 17-22, 2002.
Sharma et al., "The Application of Surface Mount Technology to Multi-Scale Process Intensification," ASPE, pp. 1-4, Oct. 2003.
Stroock et al., "Chaotic Mixer for Microchannels," Science, 295, pp. 647-651, Jan. 2002.
Thorsen et al.; Microfluidic Large-Scale Integration; Science; 298; pp. 580-584; Oct. 18, 2002.
Wegeng et al., "Chemical system miniaturization," Proceedings of the AIChE Spring National Meeting, pp. 1-13, Feb. 1996.
Hogard et al.; U.S. Appl. No. 17/244,672 entitled "Dialysis system and methods," filed Apr. 29, 2021.
Hogard et al.; U.S. Appl. No. 17/244,684 entitled "Dialysis system and methods," filed Apr. 29, 2021.

* cited by examiner

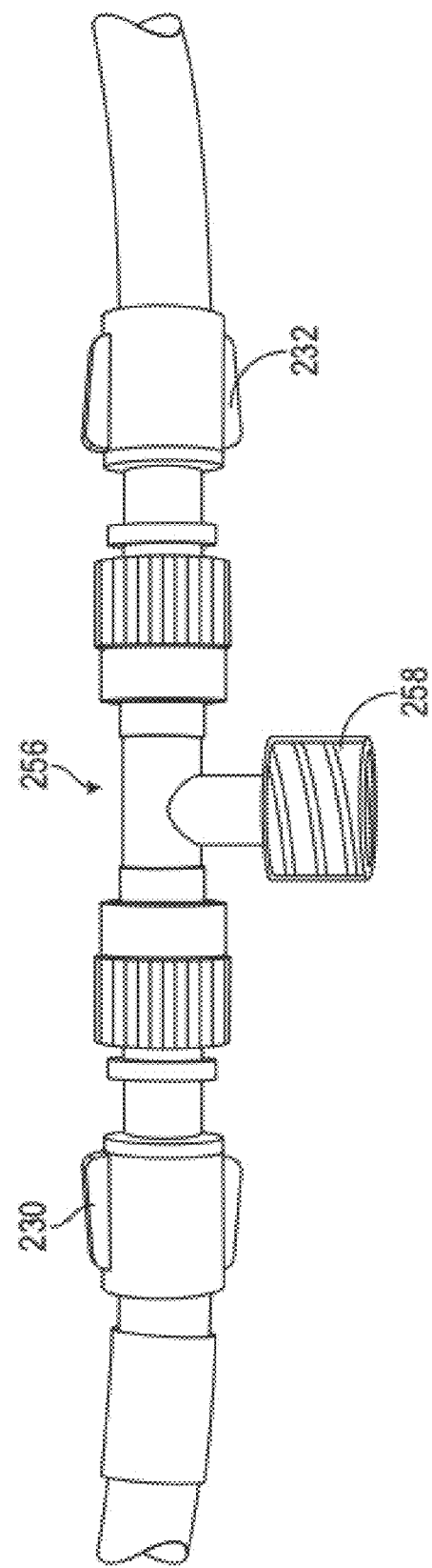

DIALYSIS SYSTEM AND METHODS

CROSS REFERENCE TO RELATED APPLICATIONS

This application claims the benefit of U.S. Provisional Appln. No. 62/722,119, filed Aug. 23, 2018, titled "Dialysis System and Methods", which is incorporated herein by reference in its entirety. This application is related to U.S. Pat. No. 9,504,777, titled "Dialysis System and Methods", which is incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure generally relates to dialysis systems. More specifically, this disclosure relates to dialysis systems that include many features that reduce the need for technician involvement in the preparation and administration of dialysis treatment.

BACKGROUND

There are, at present, hundreds of thousands of patients in the United States with end-stage renal disease. Most of those require dialysis to survive. Many patients receive dialysis treatment at a dialysis center, which can place a demanding, restrictive and tiring schedule on a patient. Patients who receive in-center dialysis typically must travel to the center at least three times a week and sit in a chair for 3 to 4 hours each time while toxins and excess fluids are filtered from their blood. After the treatment, the patient must wait for the needle site to stop bleeding and blood pressure to return to normal, which requires even more time taken away from other, more fulfilling activities in their daily lives. Moreover, in-center patients must follow an uncompromising schedule as a typical center treats three to five shifts of patients in the course of a day. As a result, many people who dialyze three times a week complain of feeling exhausted for at least a few hours after a session.

Many dialysis systems on the market require significant input and attention from technicians prior to, during, and after the dialysis therapy. Before therapy, the technicians are often required to manually install patient blood tubing sets onto the dialysis system, connect the tubing sets to the patient, and to the dialyzer, and manually prime the tubing sets to remove air from the tubing set before therapy. During therapy, the technicians are typically required to monitor venous pressure and fluid levels, and administer boluses of saline and/or heparin to the patient. After therapy, the technicians are often required to return blood in the tubing set to the patient and drain the dialysis system. The inefficiencies of most dialysis systems and the need for significant technician involvement in the process make it even more difficult for patients to receive dialysis therapy away from large treatment centers.

Given the demanding nature of in-center dialysis, many patients have turned to home dialysis as an option. Home dialysis provides the patient with scheduling flexibility as it permits the patient to choose treatment times to fit other activities, such as going to work or caring for a family member. Unfortunately, current dialysis systems are generally unsuitable for use in a patient's home. One reason for this is that current systems are too large and bulky to fit within a typical home. Current dialysis systems are also energy-inefficient in that they use large amounts of energy to heat large amounts of water for proper use. Although some home dialysis systems are available, they generally are difficult to set up and use. As a result, most dialysis treatments for chronic patients are performed at dialysis centers.

Hemodialysis is also performed in the acute hospital setting, either for current dialysis patients who have been hospitalized, or for patients suffering from acute kidney injury. In these care settings, typically a hospital room, water of sufficient purity to create dialysate is not readily available. Therefore, hemodialysis machines in the acute setting rely on large quantities of pre-mixed dialysate, which are typically provided in large bags and are cumbersome for staff to handle. Alternatively, hemodialysis machines may be connected to a portable RO (reverse osmosis) machine, or other similar water purification device. This introduces another independent piece of equipment that must be managed, transported and disinfected.

SUMMARY

A method of priming a tubing set and a dialyzer of a dialysis system is provided, comprising the steps of connecting an arterial line of a tubing set to a venous line of the tubing set to form a continuous loop in the tubing set, pumping air out of the tubing set with an air pump, pulling a flow of fluid from a fluid source into the tubing set with the air pump, operating a blood pump of the dialysis system in a forward operating mode to flow fluid from the fluid source into the tubing set in a first direction, and operating the blood pump in a reverse operating mode to flow fluid through the tubing set in a second direction opposite to the first direction.

In some examples, the pulling step further comprises pulling the fluid into the tubing set with the air pump until the fluid is detected by a first level sensor in a venous drip chamber.

In one embodiment, operating the blood pump in the forward operating mode further comprises operating the blood pump in a forward operating mode to flow fluid from the fluid source into the tubing set until the fluid is detected by a second level sensor in the venous drip chamber.

In some examples the method can include, after the pulling step, allowing a fluid level in the venous drip chamber to fall below the first level sensor.

In one embodiment, operating the blood pump in the forward operating mode further comprises operating the blood pump in a forward operating mode to flow fluid from the fluid source into the tubing set until the fluid is detected by the first level sensor in the venous drip chamber.

In another example, the method can comprise pumping air out of the tubing set with an air pump during the operating steps.

A dialysis system is also provided, comprising a fluid source, a patient tubing set fluidly coupled to the fluid source, the patient tubing set including a venous drip chamber, an air pump coupled to the venous drip chamber, the air pump being configured to pump air into or out of the venous drip chamber, a blood pump coupled to the patient tubing set, the blood pump being configured to flow fluid through the patient tubing set, at least one sensor coupled to the venous drip chamber and being configured to monitor a fluid level in the venous drip chamber, and an electronic controller in communication with the at least one sensor, the blood pump, and the air pump, the electronic controller being configured to control the air pump to pump air out of the tubing set, control the air pump to pull a flow of fluid from the fluid source into the patient tubing set, control the blood pump in a forward direction to flow fluid from the fluid source into the tubing set, and control the blood pump in a reverse direction to flow fluid through the tubing set.

A method of testing for leaks in a tubing set of a dialysis system is provided, comprising pressurizing a first segment of the tubing set, measuring a baseline pressure of the first segment tubing set, exposing a second segment of the tubing set to the pressurized first segment, measuring a pressure of the second segment of the tubing set, and comparing the measured pressure of the second segment to the baseline pressure of the tubing set to identify a leak in the second segment.

In some embodiments, exposing the second segment further comprises opening one or more pinch valves of the tubing set.

In one example, the method can include monitoring the pressure of the second segment for a pressure decay rate that exceeds a pressure decay threshold to identify a leak in the second segment.

A method of priming a tubing set of a dialysis system is provided, comprising removing the tubing set from a sterile shipping receptacle, attaching the tubing set to the dialysis system, priming the tubing set with a flow of fluid from the dialysis system to remove air from the tubing set, and draining the fluid from the tubing set into the shipping receptacle.

In some examples, the method further comprises attaching the shipping receptacle to the dialysis system.

In one embodiment, attaching the shipping receptacle further comprises engaging attachment features of the shipping receptacle with corresponding mechanical features on the dialysis system.

In some examples, the mechanical features on the dialysis system are angled with respect to another so as to impose a curvature on one or more surfaces of the shipping receptacle to enlarge an opening of the shipping receptacle.

In another embodiment, the method includes draining the fluid from the tubing set into the shipping receptacle through a junction fitting that connects an arterial line of the tubing set to a venous line of the tubing set.

A method of improving durability and operation of one or more displacement pumps is provided, comprising connecting one or more displacement pumps to a pump burn-in fixture to form a closed-loop fluidic path between the one or more displacement pumps and the pump burn-in fixture, increasing a temperature and pressure of fluid within the closed-loop fluidic path, operating the one or more displacement pumps to flow the fluid through the closed-loop fluidic path for a predetermined period of time to reduce surface imperfections internal to the one or more displacement pumps.

In one embodiment, the increasing step further comprises increasing the temperature and pressure of the fluid to levels that are above what the one or more displacement pumps encounter during normal operation.

In another embodiment, the method comprises increasing the temperature of the fluid above 25 deg C.

In another embodiment, the method comprises increasing the pressure of the fluid above 100 psi.

A pump burn-in fixture is provided, comprising a housing, a fluid source, one or more connection ports in or on the housing, one or more displacement pumps coupled to the one or more connection ports so as to form a closed-loop fluidic path between the fluid source, the one or more displacement pumps, and the one or more connection ports, a heating element configured to heat a fluid within the closed-loop fluidic path to an elevated temperature above a normal operating temperature of the one or more displacement pumps, and an electronic controller configured to control operation of the one or more displacement pumps with the elevated temperature fluid for a predetermined time to reduce surface imperfections internal to the one or more displacement pumps.

In some examples, a method of providing dialysis therapy to a patient is provided, comprising combining a dialysate concentrate and water with a dialysate system to produce a dialysate in real-time, providing a first flow of the dialysate through the dialysis system at a first dialysate flow rate, monitoring consumption of the dialysate concentrate by the dialysis system, determining if enough dialysate concentrate remains to complete the dialysis therapy at the first dialysate flow rate, and if there is not enough dialysate concentrate to complete the dialysis therapy at the first dialysate flow rate providing a second flow of the dialysate through the dialysis system at a second dialysate flow rate that allows for completion of the dialysis therapy.

In one embodiment, the method includes, before providing the second flow, calculating the second dialysate flow rate that allows for completion of the dialysis therapy.

In some embodiments, the dialysis system houses a finite supply of dialysate concentrate.

In one embodiment, the second dialysate flow rate is lower than the first dialysate flow rate.

In one example, the first dialysis flow rate is approximately 300 ml/min, and the second dialysis flow rate is approximately 100 ml/min.

In another embodiment, the determining step further comprises determining if enough dialysate concentrate remains based on the first dialysate flow rate, an amount of dialysate concentrate remaining, and a total treatment time.

In one example, the method further comprises maintaining a pressure within the dialysis system when the second flow of dialysate is provided.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 18 shows one embodiment of a union joint adapted to connect venous and arterial lines of a patient tubing set during a priming sequence.

DETAILED DESCRIPTION

This disclosure describes systems, devices, and methods related to dialysis therapy, including a dialysis system that is simple to use and includes automated features that eliminate or reduce the need for technician involvement during dialysis therapy. In some embodiments, the dialysis system can be a home dialysis system. Embodiments of the dialysis system can include various features that automate and improve the performance, efficiency, and safety of dialysis therapy.

In some embodiments, a dialysis system is described that can provide acute and chronic dialysis therapy to users. The system can include a water purification system configured to prepare water for use in dialysis therapy in real-time using available water sources, and a dialysis delivery system configured to prepare the dialysate for dialysis therapy. The dialysis system can include a disposable cartridge and tubing set for connecting to the user during dialysis therapy to retrieve and deliver blood from the user.

Figure 1:
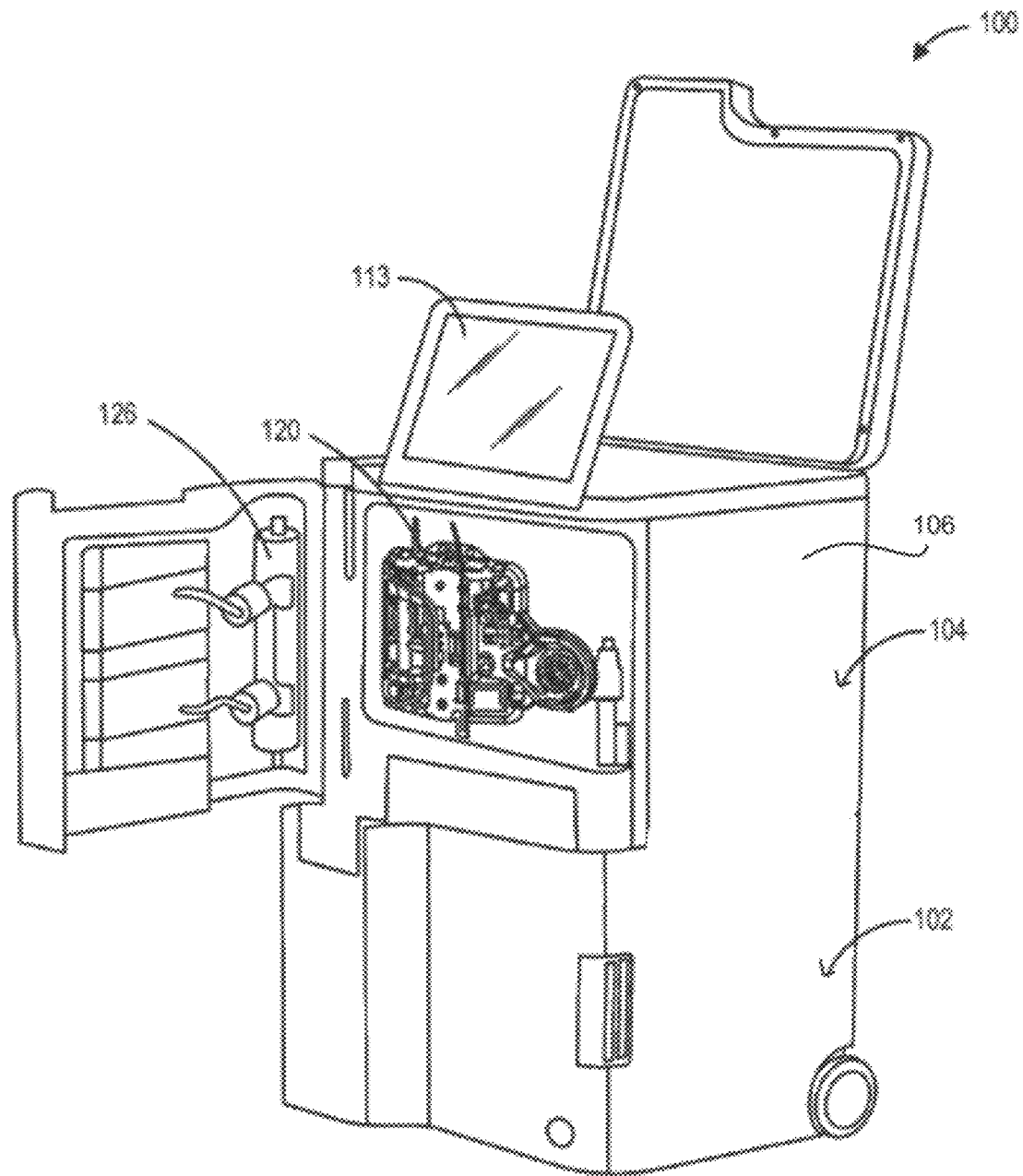
FIG. 1 shows one embodiment of a dialysis system.

FIG. 1 illustrates one embodiment of a dialysis system 100 configured to provide dialysis treatment to a user in either a clinical or non-clinical setting, such as the user's home. The dialysis system 100 can comprise a water purification system 102 and a dialysis delivery system 104 disposed within a housing 106. The water purification system 102 can be configured to purify a water source in real-time for dialysis therapy. For example, the water purification system can be connected to a residential water source (e.g., tap water) and prepare pasteurized water in real-time. The pasteurized water can then be used for dialysis therapy (e.g., with the dialysis delivery system) without the need to heat and cool large batched quantities of water typically associated with water purification methodologies.

Dialysis system 100 can also include a cartridge 120 which can be removably coupled to the housing 106 of the system. The cartridge can include a patient tubing set attached to an organizer, which will be described in more detail below. The cartridge and tubing set, which can be sterile, disposable, one-time use components, are configured to connect to the dialysis system prior to therapy. This connection correctly aligns corresponding components between the cartridge, tubing set, and dialysis system prior to dialysis therapy. For example, the tubing set is automatically associated with one or more pumps (e.g., peristaltic pumps), clamps and sensors for drawing and pumping the user's blood through the tubing set when the cartridge is coupled to the dialysis system. The tubing set can also be associated with a saline source of the dialysis system for automated priming and air removal prior to therapy. In some embodiments, the cartridge and tubing set can be connected to a dialyzer 126 of the dialysis system. In other embodiments, the cartridge and tubing set can include a built-in dialyzer that is pre-attached to the tubing set. A user or patient can interact with the dialysis system via a user interface 113 including a display.

Figure 2:
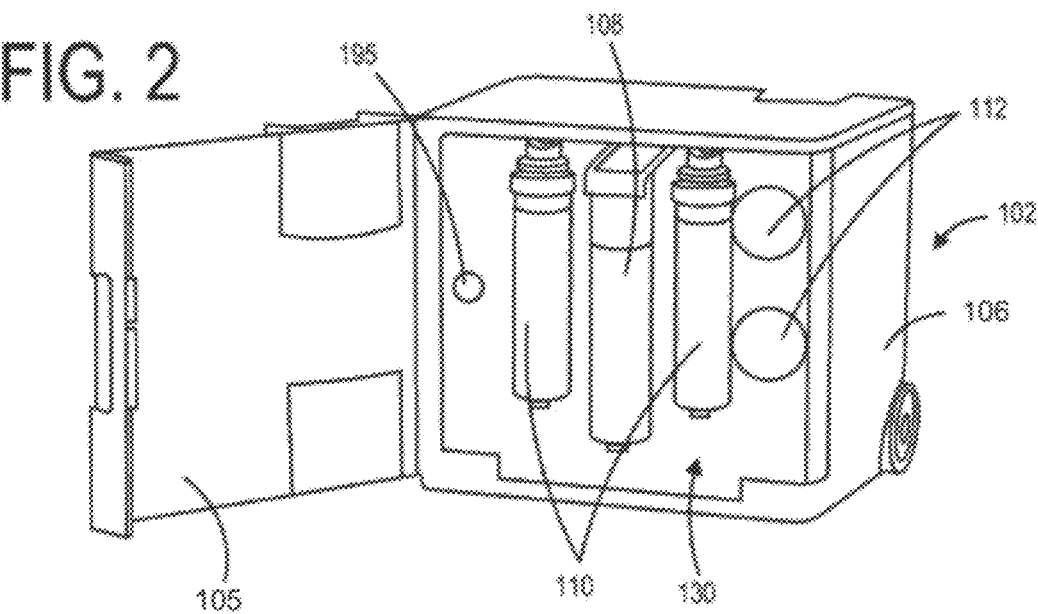
FIG. 2 illustrates one embodiment of a water purification system of the dialysis system.
Figure 3:
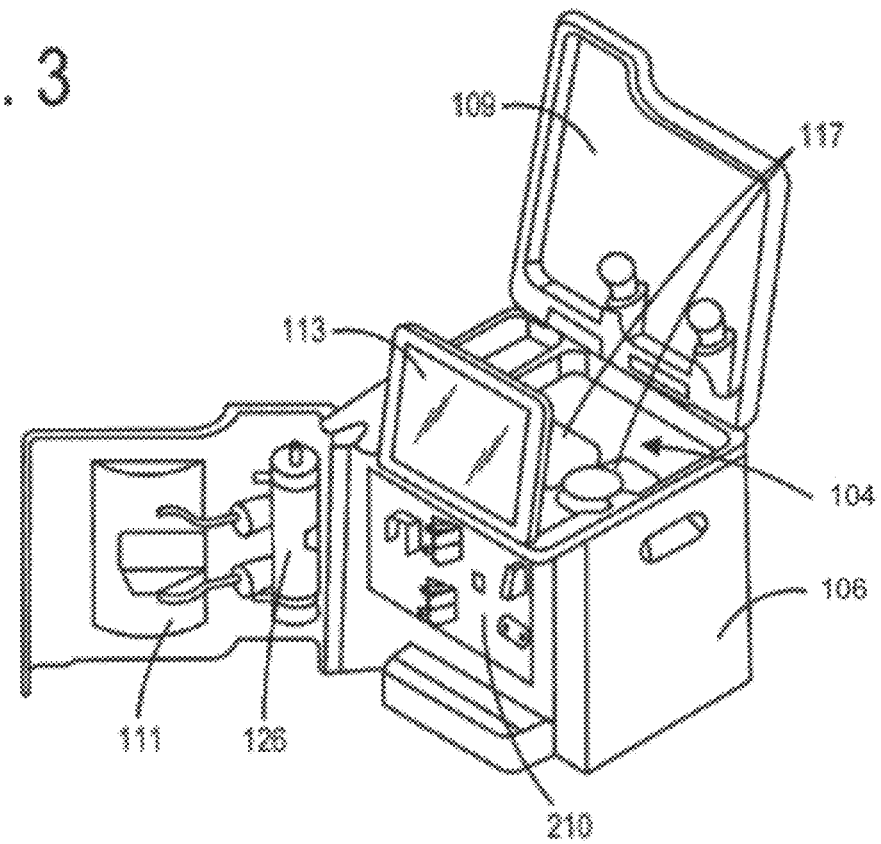
FIG. 3 illustrates one embodiment of a dialysis delivery system of the dialysis system.

FIGS. 2 and 3 illustrate the water purification system 102 and the dialysis delivery system 104, respectively, of one embodiment of the dialysis system 100. The two systems are illustrated and described separately for ease of explanation, but it should be understood that both systems can be included in a single housing 106 of the dialysis system. FIG. 2 illustrates one embodiment of the water purification system 102 contained within housing 106 that can include a front door 105 (shown in the open position). The front door 105 can provide access to features associated with the water purification system such as one or more filters, including sediment filter(s) 108, carbon filter(s) 110, and reverse osmosis (RO) filter(s) 112. The filters can be configured to assist in purifying water from a water source (such as tap water) in fluid communication with the water purification system 102. The water purification system can further include heating and cooling elements, including heat exchangers, configured to pasteurize and control fluid temperatures in the system, as will be described in more detail below. The system can optionally include a chlorine sample port 195 to provide samples of the fluid for measuring chlorine content.

In FIG. 3, the dialysis delivery system 104 contained within housing 106 can include an upper lid 109 and front door 111, both shown in the open position. The upper lid 109 can open to allow access to various features of the dialysis system, such as user interface 113 (e.g., a computing device including an electronic controller and a display such as a touch screen) and dialysate containers 117. Front door 111 can open and close to allow access to front panel 210, which can include a variety of features configured to interact with cartridge 120 and its associated tubing set, including alignment and attachment features configured to couple the cartridge 120 to the dialysis system 100. Dialyzer 126 can be mounted in front door 111 or on the front panel, and can include lines or ports connecting the dialyzer to the prepared dialysate as well as to the tubing set of the cartridge.

In some embodiments, the dialysis system 100 can also include a blood pressure cuff to provide for real-time monitoring of user blood pressure. The system (i.e., the electronic controller of the system) can be configured to monitor the blood pressure of the user during dialysis therapy. If the blood pressure of the user drops below a threshold value (e.g., a blood pressure threshold that indicates the user is hypotonic), the system can alert the user with a low blood pressure alarm and the dialysis therapy can be stopped. In the event that the user ignores a configurable number of low blood pressure alarms from the system, the system can be configured to automatically stop the dialysis therapy, at which point the system can inform the user that return of the user's blood (the blood that remains in the tubing set and dialyzer) back to the user's body is necessary. For example, the system can be pre-programmed to automatically stop therapy if the user ignores three low blood pressure alarms. In other embodiments, the system can give the user a bolus of saline to bring user fluid levels back up before resuming dialysis therapy. The amount of saline delivered to the patient can be tracked and accounted for during ultrafiltration fluid removal.

The dialysis delivery system 104 of FIG. 3 can be configured to automatically prepare dialysate fluid with purified water supplied by the water purification system 102 of FIG. 2. Furthermore, the dialysis delivery system can de-aerate the purified water, and proportion and mix in acid and bicarbonate concentrates from dialysate containers 117. The resulting dialysate fluid can be passed through one or more ultrafilters (described below) to ensure the dialysate fluid meets certain regulatory limits for microbial and endotoxin contaminants.

Dialysis can be performed in the dialysis delivery system 104 of the dialysis system 100 by passing a user's blood and dialysate through dialyzer 126. The dialysis system 100 can include an electronic controller configured to manage various flow control devices and features for regulating the flow of dialysate and blood to and from the dialyzer in order to achieve different types of dialysis, including hemodialysis, ultrafiltration, and hemodiafiltration.

Figure 4:
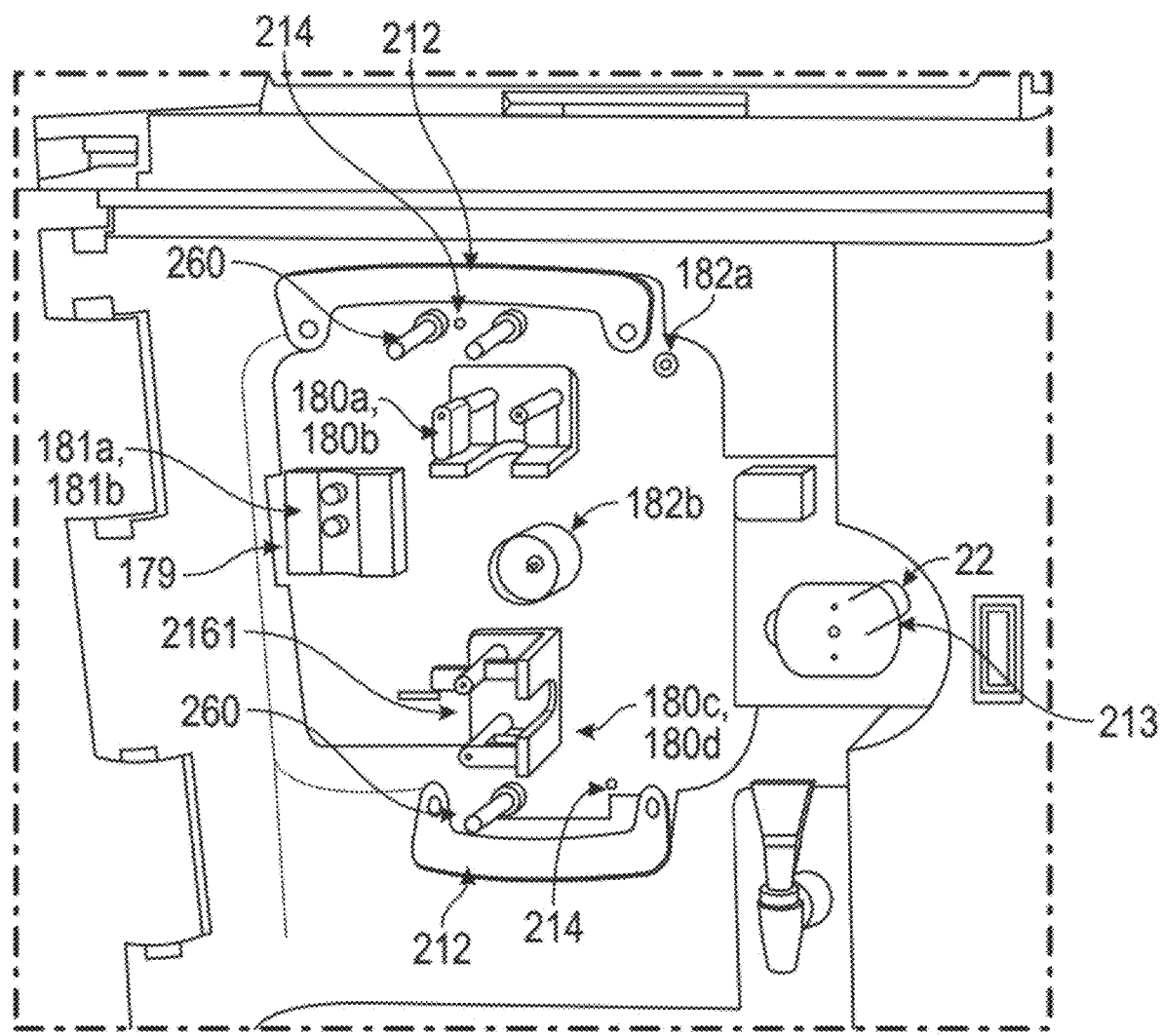
FIG. 4 shows one example of a front panel of the dialysis delivery system.

FIG. 4 shows one example of front panel 210 of the dialysis delivery system 104 of FIG. 3, which can include a number of features that assist with positioning and attaching cartridge 120 and its associated tubing set to the dialysis system 100, and for monitoring and controlling fluid flow along the tubing set of the cartridge. During installation of a new sterile cartridge onto the dialysis system, alignment features on the cartridge (e.g., holes 125 through the cartridge, shown in FIG. 5) can be lined up with locator pegs 260. The locator pegs also serve to align the cartridge and the tubing set with features on the front panel used for dialysis treatment, including blood pump 213 and spring wire 22, positioning features 212, venous and arterial pressure sensor(s) 182a and 182b, venous air sensor 2161, arterial air sensor 216, pinch valve(s) 18a-d, and venous drip chamber holder 179. Blood pump 213 can be a peristaltic pump, for example. A holder or slot 215 for an infusion pump or syringe is also shown.

The cartridge can be pressed into place on the front panel using these locator pegs 260 to ensure that all the features of the cartridge and tubing set line up and are installed properly with the corresponding features of the front panel 210. In some embodiments, the cartridge can be easily installed with a single hand, and closing the door of the system can seat the cartridge onto the system. As shown in FIG. 1, the dialysis system can include wheels for ease of transport. In one specific embodiment, a force applied to seat the cartridge horizontally onto the front panel 210 by closing the door with a downward rotating motion of a lever on the door does not tend to move the dialysis system 100 on its wheels.

The pinch valves can be used for a number of functions before, during, and after dialysis therapy. The pinch valves 180a-d can be controlled by the electronic controller of the dialysis delivery system. Pinch valves 180a and 180b can be configured to control the flow of saline from a saline source (such as a saline bag) to the tubing set. In some embodiments, the pinch valves can be opened and the blood pump 213 can be operated to draw saline into the tubing set to remove air during a priming sequence, to flush impurities from the dialyzer before treatment, and to displace blood back to the user at the end of a treatment. The pinch valves 180a and 180b can also be used to deliver therapeutic boluses of saline to the user during therapy to maintain blood pressure or adjust electrolytes or fluid levels of the patient. In other embodiments, pumps such as peristaltic pumps may be configured to deliver therapeutic boluses of saline to the user.

Pinch valves 180c and 180d can be configured to close the arterial and venous lines of the tubing set that connect to the user. They can also be opened and closed multiple times before, during, and after treatment to facilitate actions such as tubing set pre-conditioning tubing to achieve proper compliance, priming, discarding of priming saline, blood return to the patient, and/or draining the dialyzer after treatment. In one embodiment, the system can incorporate information from venous air sensor 2161, arterial air sensor 216, or other air sensors in the system to close pinch valves 180c and 180d in the event that air bubbles are found in the lines, particularly in the venous line. In a further embodiment, the system can be configured to remove the detected air bubble(s) by reversing the operation of the blood pump to attempt to clear the air bubble(s) through the venous drip chamber.

Pinch valves 180a-d can also be actuated to perform a series of self-tests on the tubing set prior to each treatment. The tubing set can be pressurized with the blood pump, and the pressure can be held in the tubing set by closing the pinch valves. The arterial and venous pressure sensors can then be used to look for pressure decay in the tubing set.

FIG. 4 also illustrates venous drip chamber holder 179, which can include a pair of venous level sensors 181a and 181b. When the cartridge is coupled to the dialysis delivery system, the venous drip chamber (described in more detail below) can engage the venous drip chamber holder 179. During dialysis therapy, the venous level sensors 181a and 181b can monitor the fluid level in the venous drip chamber. If the fluid level rises above sensor 181a, then the dialysis delivery system can automatically pump air into the venous drip chamber to lower the fluid level. Alternatively, if the fluid level dips below sensor 181b, then the dialysis delivery system can automatically pump air out of the venous drip chamber (or alternatively, vent air out of the chamber) to raise the fluid level. Automatic level control reduces labor, as periodic adjustments to the level can be made by the machine instead of by clinic staff or the patient.

In other embodiments, the system may comprise algorithmic features to protect itself from the failure of one or more of the venous level sensors 181a or 181b and still allow automatic level control. During treatment, the venous drip chamber 361 will be filled with blood. Detecting blood level in a drip chamber can be hindered by the tendency of blood to clot. These conditions can cause venous level sensors to not accurately sense the true level of the blood, causing the system to raise or lower the level incorrectly. This could lead to the fluid level to drop excessively, resulting in the air detector creating an alarm, or for the fluid level to raise excessively, which can cause blood to enter line 363 and foul venous transducer protector 371, hindering pressure readings.

In these embodiments, algorithmically improved automatic level control within the venous drip chamber can be maintained under the adverse conditions of clots and foam. The algorithmically improved automatic level control may utilize the ideal gas law to determine a set amount ("air budget") of air for air pump 250 to either inject or remove to lower or raise the level, based on pressure detected within the chamber by venous pressure sensor 182a. This is possible because the geometric gas volumes of drip chamber and tubing connections are known. At high pressure, air is volumetrically compressed, and therefore the linear distance that a level within a substantially straight-walled chamber is raised or lowered will be smaller, for a given amount of air injected or removed. If the lower level sensor 181b detects air (or a clot forms that is sensed as air), the algorithm will begin raising the level. For a given venous pressure, the pump removes air up until the budget of air has been reached. The budget is determined to place the fluid level between the two level sensors, and is dynamically calculated using the ideal gas law as described above. In the event that the system is actually detecting air as opposed to a clot, the fluid rises and as a result the lower level 181b sensor will again detect fluid. At this point the algorithm resets the air budget available to be used the next time lower level sensor 181b detects air. If, however, lower level sensor 181b incorrectly detects air because it is confounded by a clot or other phenomena, it will still not detect air after the air pump removes air and raises the level. At this point, the algorithm begins controlling the level dynamically based on the pressure in the drip chamber. If the pressure increases, the gas space above the fluid compresses, causing the fluid level to rise. Conversely, if the pressure decreases, the gas space above the fluid expands, causing the fluid level to drop. A pressure increase or decrease will be detected by venous pressure sensor 182a. If a pressure change of sufficient magnitude is detected, the control algorithm uses the pressure/volume relationship of the ideal gas law and calculates an amount of air to add or remove using the air pump 250 to counteract the rise or drop in level. In some embodiments, the pressure change threshold is 20 mmHg. In some embodiments, the pressure change threshold is 50 mmHg. In some embodiments, the pressure change threshold is 100 mmHg. The amount of air to be removed or injected is calculated dynamically using the both the magnitude and change in venous pressure. In further embodiments, if pressure in the chamber is not changed, and the upper level sensor 181a senses fluid, the control algorithm will cause air pump 250 to inject a calculated budget of air into the chamber to drive the level down.

Figure 30:
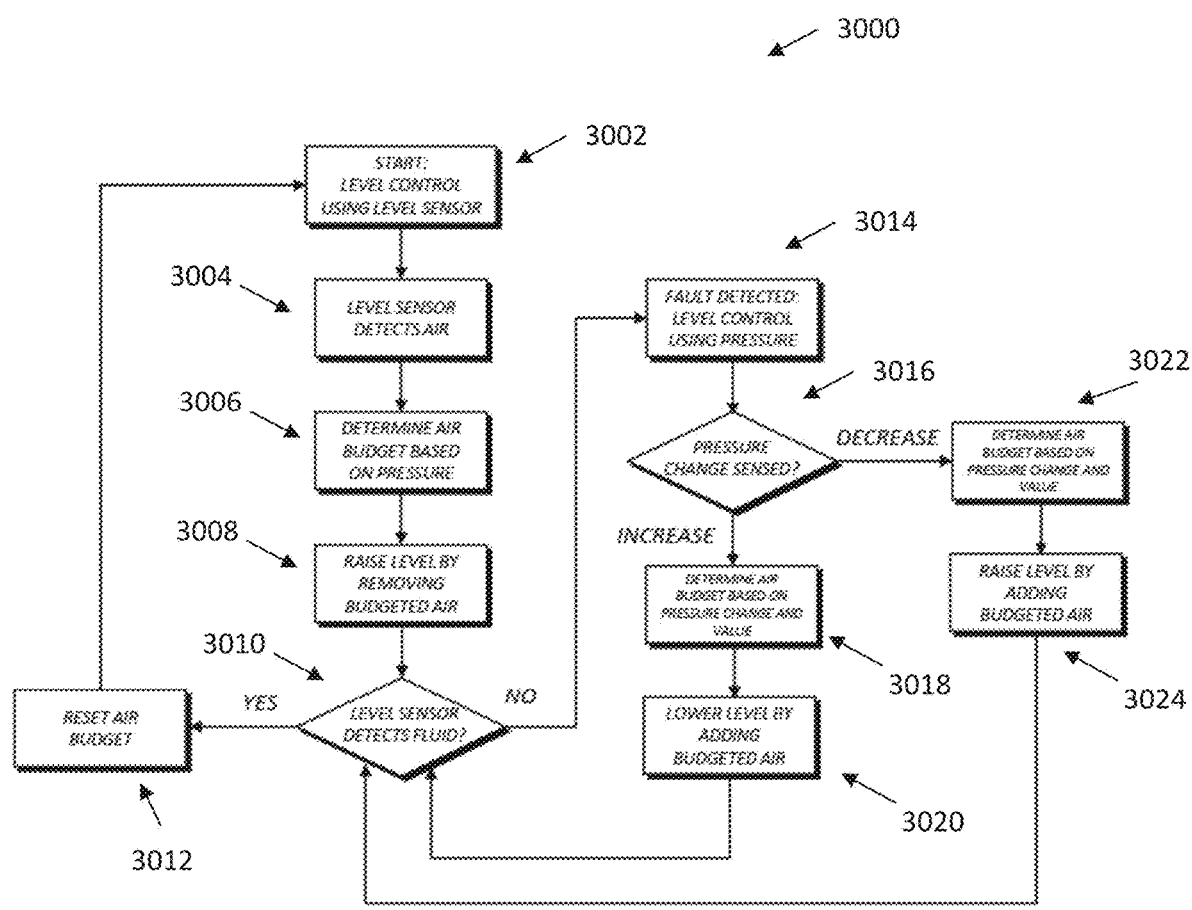
FIG. 30 is a flowchart describing one method for automatically controlling a fluid level within a venous drip chamber during dialysis therapy.

FIG. 30 illustrates a flowchart 3000 that describes the automatic level control process described above. At step 3002 of flowchart 3000, the dialysis system can automatically control the fluid level in the venous drip chamber during therapy as described above (e.g., but measuring the fluid level with a low level sensor and a high level sensor in the venous drip chamber and automatically raising or lowering the fluid level based on the sensed fluid level). During the dialysis therapy, at step 3004, if the lower level sensor detects air (instead of fluid), then at step 3006 the dialysis system can determine an "air budget" of air for the air pump of the system to either inject or remove from the venous drip chamber. This "air budget" can be based on a measured pressure within the venous drip chamber and is dynamically calculated so as to place the fluid level between the upper level sensor and the lower level sensor. In some embodiments, the pressure within the venous drip chamber is measured with a venous pressure sensor of the dialysis system. Next, at step 3008, the dialysis system can raise the fluid level by removing a volume air from the venous drip chamber with air pump that is equal to the calculated "air budget". After the volume of air has been removed from the venous drip chamber, if at step 3010 the lower level sensor detects fluid, then the "air budget" can be reset at step 3012.

Referring to step 3010 again, in some instances the lower level sensor will still detect air, even after removing the budgeted air in step 3008. This could be caused, for example, by a clot or other phenomena in the venous drip chamber. In this event, at step 3014, a fault is detected and the dialysis system can switch to controlling the fluid level in the venous drip chamber based on measured pressure. At step 3016, the system will continuously measure the pressure within the venous drip chamber. If a pressure change above a pressure threshold is detected (e.g., a pressure change greater than 20-50 mmHg) then at steps 3018/3022, the system can determine an "air budget" based on the pressure change and pressure magnitude. At step 3020, the fluid level can be lowered by adding the budgeted air, and at step 3024, the fluid level can be raised by adding the budgeted air.

In other embodiments, the system may comprise a single analog or non-binary digital level sensor in the place of the two venous level sensors to detect the actual level within the drip chamber. The dialysis delivery system can then be configured to perform analogous adjustments as described above based on the level detected by this single sensor. The single sensor can comprise, for example, an ultrasonic, optical, or capacitive level sensor.

Still referring to FIG. 4, in one embodiment, attaching the cartridge onto the front panel 210 properly will engage cartridge presence detector 214, which can be a switch or a sensor configured to communicate to the dialysis system (e.g., to a controller of the system) that a cartridge is installed on the front panel. As a safety precaution, the system will not allow pinch valves 180a-d to be closed until the cartridge presence detector 214 indicates that the cartridge is installed properly. The presence detector can also initiate automatic loading of a blood pump portion of the tubing set into the blood pump. In one embodiment, the blood pump can include a spring wire 22 that is actuated to grasp and pull the blood pump portion of the tubing set into the blood pump when the presence detector 214 is depressed. Furthermore, the connection of the cartridge and tubing set to the front panel can also initiate a self-check in each portion of the tubing set to identify any leaks in the tubing.

Figure 5:
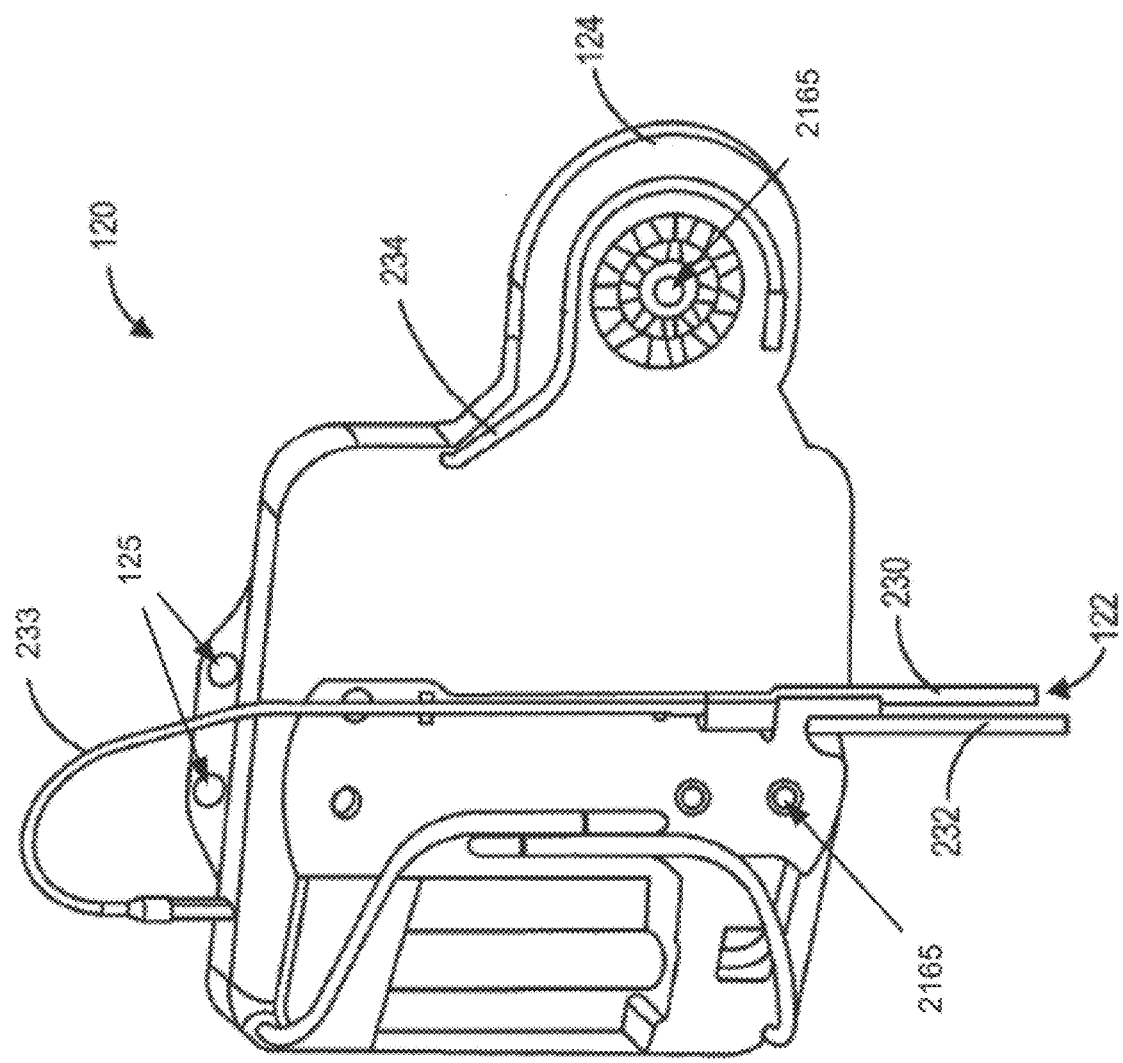
FIGS. 5 and 6 illustrate one embodiment of a cartridge including a tubing set attached to an organizer.
Figure 6:
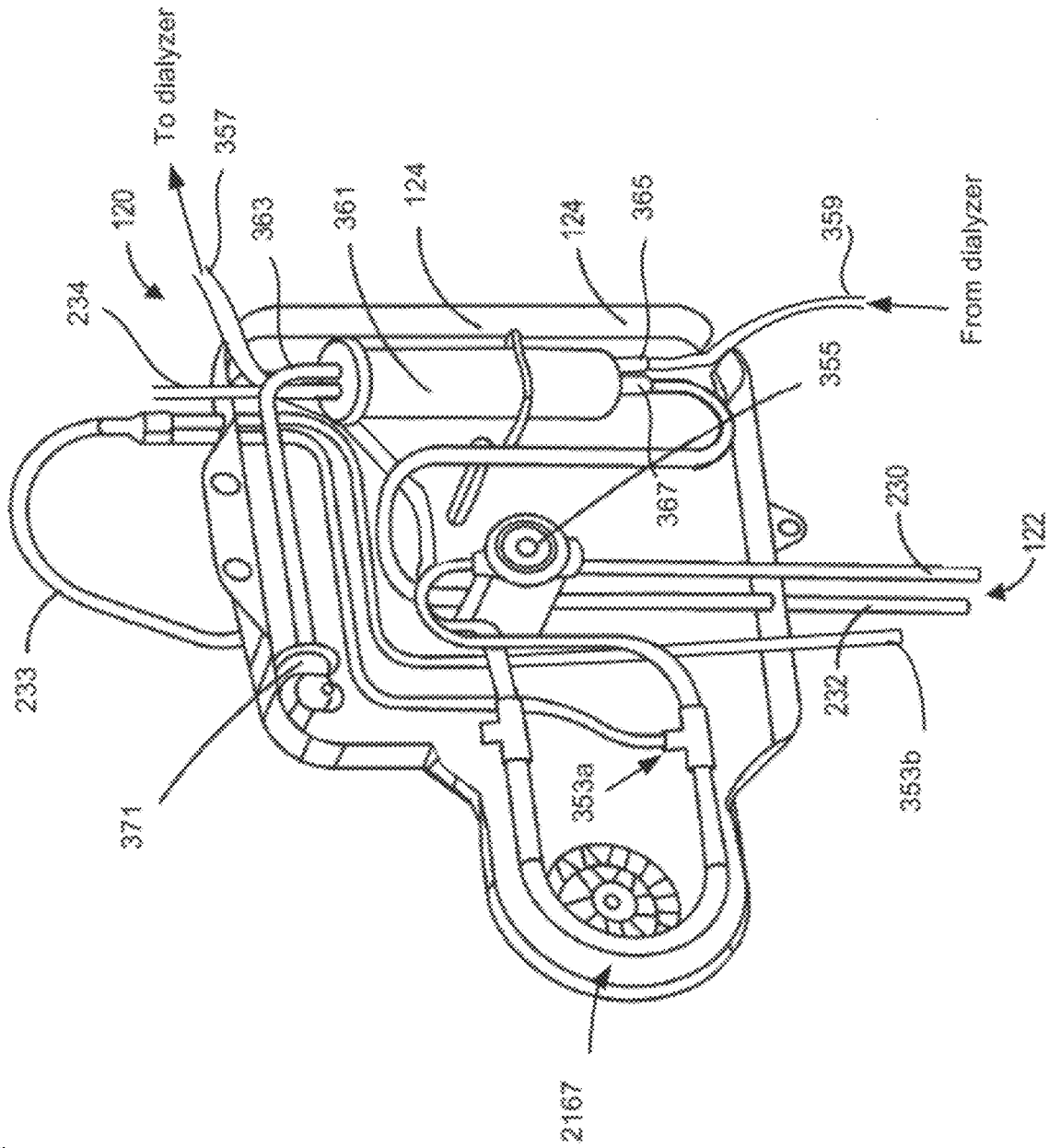

FIGS. 5 and 6 illustrate one embodiment of a cartridge 120 including tubing set 122 attached to an organizer 124. Although the majority of the tubing set 122 is blocked from view in FIG. 5 by the organizer, arterial line 230, venous line 232, saline line 233, and infusion line 234 can be seen. Referring to FIG. 5, a user can ensure proper placement of the cartridge relative to the front panel with organizer 124 by aligning holes 125 of the organizer with the locator pegs 260 of the front panel. FIG. 5 shows a plurality of aligning holes 125 near the top of the organizer, but it should be understood that any number and location of aligning holes and locator pegs can be used to align and mount the cartridge 120. In addition, the organizer 124 can ensure proper placement of the tubing set 122 relative to one or more features of the dialysis system, including valves (such as pinch valves 180a-d described above), sensors (such as pressure and air sensors) the blood pump, the venous drip chamber, etc. Also shown in FIG. 5, the cartridge can include a number of access holes 2165 for gaining access to features on the dialysis delivery system, such as gaining access to pinch valves or the blood pump when the cartridge is installed on the system.

FIG. 6 shows the back side of the cartridge 120 and organizer 124 which is configured to interface with the front panel 210 of the dialysis delivery system, including the tubing set 122. The tubing set 122 of the cartridge 120 can include an arterial line 230, a venous line 232, and a blood pump portion 2167 configured to interface with the blood pump 213 on the front panel 210. The blood pump 213 can be configured to draw blood from a user through arterial line 230, pass the blood through a dialyzer, and return the treated blood to the patient through venous line 232. The tubing set 122 can also be connected to venous drip chamber 361 for the removal of air from the lines during therapy and priming. A continuous pathway through which blood can circulate and dialyze can be created by connecting one end of the arterial line 230 and one end of the venous line 232 of the tubing set 122 to the user's blood vessels, such as via an access point (e.g., fistula needles or catheter). Opposite ends of the arterial and venous lines can be attached to the dialyzer (described below), such as via color coded connectors (e.g., red for arterial and blue for venous).

The tubing set can further include saline connections 353a and 353b to a saline solution, such as a saline bag, via a saline line 233. As shown in FIG. 6, saline connection 353a can connect to the tubing set proximal to the blood pump portion of the tubing set. Tubing set 353b can exit the cartridge and connect to the tubing set on arterial line 230 near where the arterial line is connected to the user. Connecting the saline connection 353b near the arterial connection to the user improves blood return after a dialysis treatment since all the blood in the arterial line can be flushed back into the user. The tubing set can also include a connection to an infusion pump or syringe via the infusion line 234. The infusion pump and infusion line can connect to the tubing set at a non-pulsatile location, such as at the top of the venous drip chamber, to prevent back-streaming of blood up into the heparin line. In some embodiments, the infusion pump is integral to the system. In other embodiments, the infusion pump is separate from the system. The connection at the top of the venous drip chamber can be a non-pulsatile location due to the air gap created between the heparin line and fluid in the venous drip chamber.

Flow of fluid, such as blood, through the tubing set 122 will now be described. As described above, the blood pump that interacts with blood pump portion 2167 of tubing set 122 can be a peristaltic pump. The blood pump can operate in two modes of operation. One mode of operation can be a "forward" operating mode of the blood pump that can be used during dialysis therapy to move blood from the patient into the tubing set and back to the patient. Another mode of operation can be a "reverse" operating mode of the blood pump that can be used during a priming sequence to move saline through the tubing set. Fluid flows through the tubing set in the "forward" operating mode in a direction opposite to fluid flowing through the tubing set in the "reverse" operating mode. During dialysis therapy, blood can be drawn from the patient into the tubing set 122 through arterial line 230, due to the blood pump 213 interacting with the tubing set in the "forward" operating mode. Arterial pressure pod 355 can mate with a pressure sensor (arterial pressure sensor 182b of FIG. 4) or transducer on the front panel of the dialysis delivery system to measure the pressure on the arterial line during therapy. The arterial pressure pod 355 comprises a diaphragm that allows for pressure to be transmitted without the transmission of blood into the system. The blood can continue through the tubing set, past saline connection 353a and through the blood pump portion of the tubing set, and through tubing portion 357 towards the dialyzer. Once the blood has traveled through the dialyzer, it can continue in the tubing set 122 through tubing portion 359 back into the cartridge, where it enters venous drip chamber 361 at the bottom of the drip chamber at entry port 365. Blood flows into the venous drip chamber 361, where air is separated from the blood into the venous drip chamber and removed from the system (e.g., such as from a vent or port at the top of the drip chamber). The venous drip chamber can be connected to a venous pressure sensor or transducer on the dialysis delivery system via line 363 and venous transducer protector 371, which prevents blood or other fluids from contaminating the pressure sensor. Blood that has entered the venous drip chamber can then exit the chamber via exit port 367 and continue to flow through the tubing set until it is returned to the patient through venous line 232.

As shown in FIG. 6, the venous drip chamber includes entry and exit ports 365 and 367 that allows blood to enter and exit the venous drip chamber from the bottom of the venous drip chamber. Any air bubbles caught in the line or the blood percolate into the chamber and are removed from the blood before it is returned to the patient. This configuration allows for fluid flow through the tubing set to be reversed during priming of the dialyzer to push air up and out of the dialyzer. It also allows for the flow of blood to be reversed in the tubing set in the event that air is detected in the venous line of the tubing set.

Priming and Prime Discard

Before treatment, the tubing set can be primed with saline to remove air from the line and prepare the system for dialysis therapy. During a priming sequence, the arterial and venous lines of the tubing set can be connected together to form a continuous loop in the tubing set. FIG. 18 shows one embodiment of a union joint 256 configured to attach arterial line 230 to venous line 232. In some embodiments, the union joint 256 may be shaped like a "T" or "Y" or other configuration that has at least three connected tubing paths: 1) the arterial line, 2) the venous line, and 3) a conduit for priming fluid to exit the tubing set. This third tubing path may be selectively opened or closed, i.e. with an external cap 258. This junction fitting will be the only exposed open surface during the prime discard procedure, which provides improved infection control over having two exposed patient connection points.

During a priming sequence to remove air from the tubing set and prepare the system for therapy, saline can be drawn into the tubing set through saline connections 353a and/or 353b by activating the blood pump in the "forward" and "reverse" operating modes to cause the blood pump to interact with the tubing set and move saline into the tubing set from the saline source. When the pump operates in this "reverse" operating mode, the saline moves from the saline source into the tubing set and the blood-side of the dialyzer to fill the tubing set and the dialyzer with fluid and remove air from the tubing set via the venous drip chamber. In this "reverse" operating mode, saline flows through the tubing set in the opposite direction of blood flow during dialysis therapy. Thus, the saline flows through the venous drip chamber before flowing through the blood-side of the dialyzer. Air in the venous drip chamber can be monitored with the venous level sensors. Any air in the system can be pushed by the saline into the venous drip chamber.

When the venous level sensors no longer detect any changes to the fluid level in the venous drip chamber, or when air sensors no longer detect air circulating through the tubing set, then the tubing set is primed and ready for treatment. The blood pump can then be operated in the "forward" operating mode to move the saline in the other direction than described above and out of the tubing set. In the "forward" operating mode, the saline travels through the blood-side of the dialyzer before passing through the venous drip chamber and into the patient through venous line 232. In some embodiments, the saline used during the priming sequence is delivered into the patient at the start of dialysis therapy. The amount of saline delivered is tracked and accounted for during dialysis therapy depending on the patient's individual fluid removal requirements. In another embodiment, some or all of the saline is pumped or drained out of the tubing set prior to therapy.

To complete the priming sequence, dialysate can be pumped or moved through the dialysate-side of the dialyzer with a dialysate pump (described below). The dialysate is pumped through the dialysate-side of the dialyzer in the same direction that saline is pumped through the blood-side of the dialyzer. The direction of the saline and dialysate through the dialyzer can be in the direction of bottom to top through the dialyzer, which allows the bubbles to naturally purge through the top of the dialyzer. Thus, the priming sequence of the present disclosure can remove air from both the blood-side and dialysate-sides of the dialyzer without physically manipulating or "flipping" an orientation of the dialyzer, as is required by other conventional systems, since the priming sequence moves fluid through both sides of the dialyzer in the same direction.

During therapy, blood in the tubing set normally passes through the blood-side of the dialyzer in the top down direction. However, during priming, the blood pump can be operated in the "reverse" direction to push saline through the dialyzer in the bottom to top direction to more effectively remove air from the dialyzer. The unique configuration of the tubing set and venous drip chamber allows for the flow of saline in the "reverse" direction through the tubing set because fluid both enters and exits the venous drip chamber at connections on the bottom of the venous drip chamber. Conventional venous drip chambers, in which tubing connections are made at the top and bottom of the venous drip chamber, only allow for fluid flow through the venous drip chamber in one direction. The unique configuration of this disclosure allows for priming of both the blood and dialysate sides of the dialyzer without having to physically flip the dialyzer. Any air generated in the venous drip chamber during priming can be removed by either venting out of the system, or pumping out of the system. In one embodiment, the pinch valves of the system can be periodically actuated to open and close the saline lines of the tubing set depending on the timing of the priming sequence to "bang" bubbles loose in the dialyzer. For example, the pinch valves can be opened and closed every 4-8 seconds to create a pulsing effect of the saline in the lines.

Figure 29A:
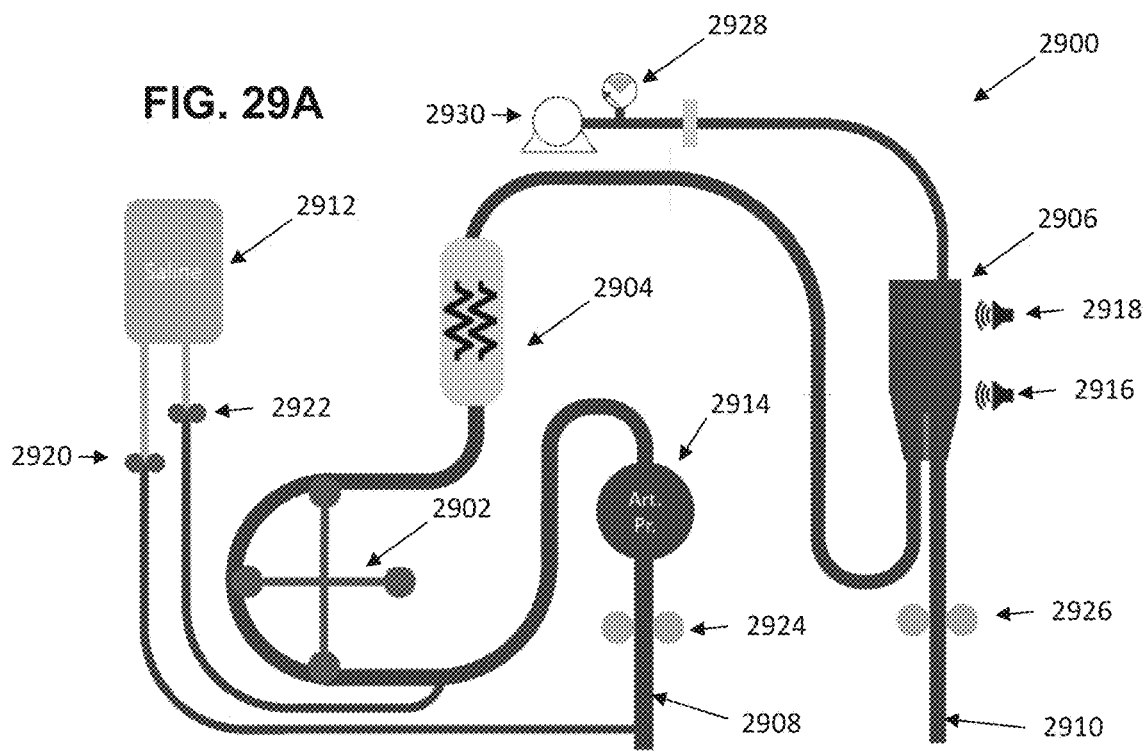
FIGS. 29A, 29B, 29C, 29D, 29E, 29F, 29G, 29H, 29I, 29J, 29K and 29L illustrate another sequence of priming a patient tubing set prior to dialysis therapy.

FIGS. 29A-29L illustrate another sequence of priming a patient tubing set prior to dialysis therapy. As shown in FIG. 29A, the patient tubing set and dialysis system 2900 can include a blood pump 2902, a dialyzer 2904, a venous drip chamber 2906, an arterial line 2908, a venous line 2910, and a saline source 2912. The tubing set can further include an arterial pressure sensor 2914 configured to sense a pressure in the arterial line, and one or more level sensors 2916 and 2918 coupled to the venous drip chamber. The one or more level sensors can be configured to detect fluid within the venous drip chamber during priming and during dialysis therapy. In the illustrated embodiment, two level sensors are shown, but it should be understood that one, or more than two, sensor(s) can be implemented to achieve the same or similar functionality described herein. The system can further include a plurality of valves, such as pinch valves, including first and second saline pinch valves 2920 and 2922, arterial pinch valve 2924, and venous pinch valve 2926, which can be actuated by an electronic controller (not shown but described herein) to change and adapt flow paths of fluid within the tubing set. Finally, the patient tubing set and dialysis system can include an air pump 2928 and a pressure sensor 2930, both of which are disposed upstream of the venous drip chamber.

Figure 29B:
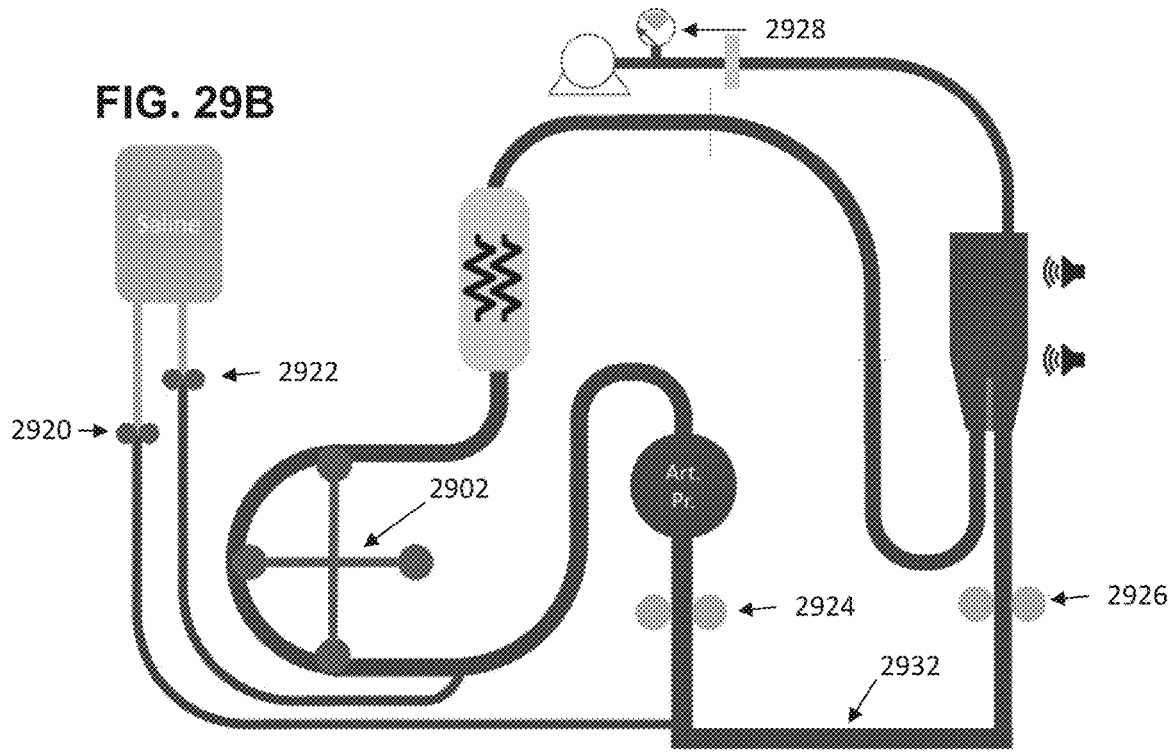

FIG. 29B illustrates the initial conditions of the tubing set and dialysis system prior to beginning a priming sequence. In FIG. 29, first and second saline pinch valves 2920 and 2922 can be closed, and arterial pinch valve 2924 and venous pinch valve 2926 can be opened. Also, connector 2932 can be used to connect the arterial line with the venous line to create a closed-loop flow path in the patient tubing set. In this initial state, the blood pump 2902 can turned off, and the air pump 2928 can be operated to begin to pull air out of the tubing set. Since the first and second saline pinch valves are closed at this step, the patient tubing set forms a closed-loop and the air pump can begin to form a vacuum in the tubing set.

Figure 29C:
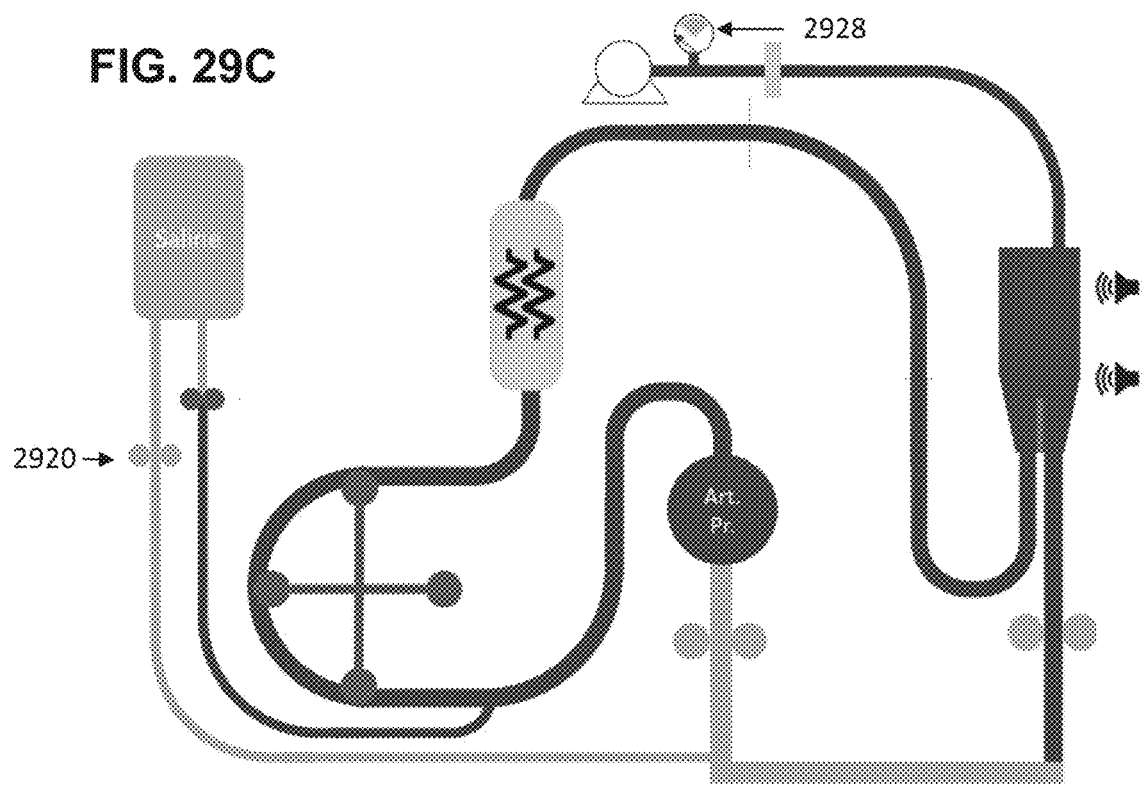

Next, as shown in FIG. 29C, the first saline pinch valve 2920 can be opened while the air pump 2928 continues to operate, which pulls saline into the patient tubing set from the saline source. This step can be performed for a predetermined time period. For example, the air pump can be used to pull saline into the tubing set for 2-20 seconds. In the illustrated example, the saline level rises to the arterial pressure sensor during this step.

Figure 29D:
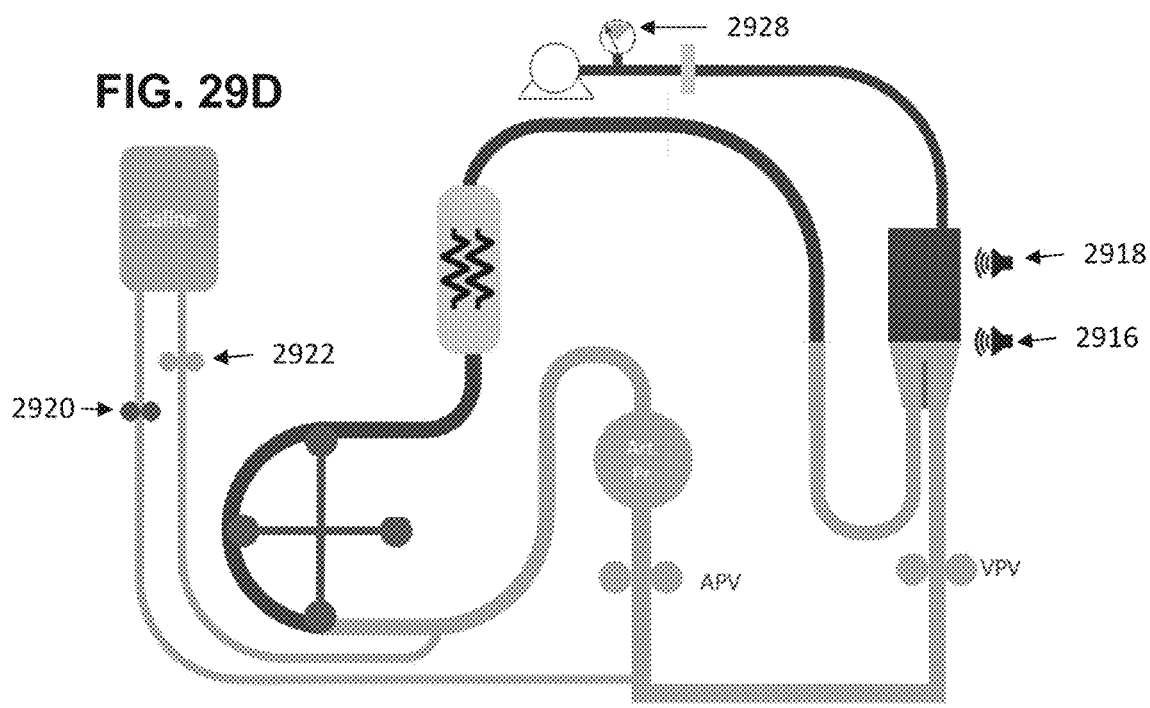

Next, as shown in FIG. 29D, the first saline pinch valve 2920 can be closed, the second saline pinch valve 2922 can be opened, and the air pump 2928 can continue to pull saline into the tubing set. This operation can be continued until the fluid level in the tubing set reaches a predetermined level. In one example, the air pump can pull saline into the tubing set until the saline or fluid level is detected in the venous drip chamber by one or more level sensors. In the illustrated embodiment, this operation ceases when fluid is detected by the lower level sensor 2916. However, it should be understood that this operation could continue until detection by the upper level sensor 2918. In embodiments with a single level sensor, the operation can cease when the fluid is detected by that single sensor.

Figure 29E:
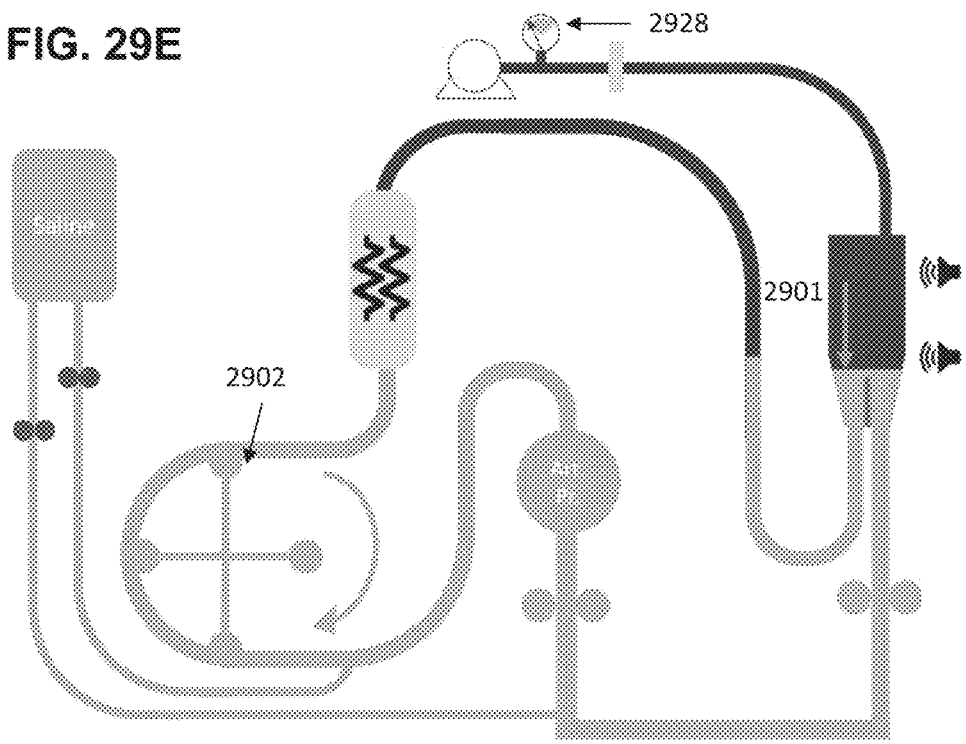
Figure 29F:
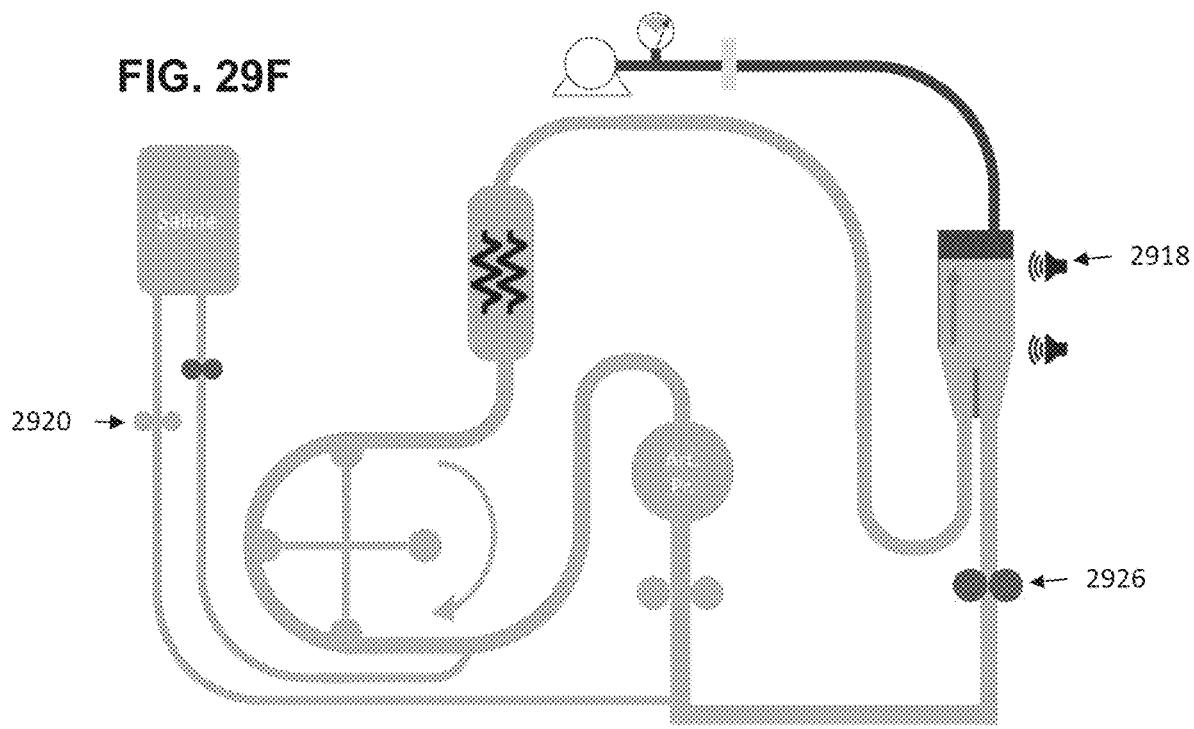
Figure 29G:
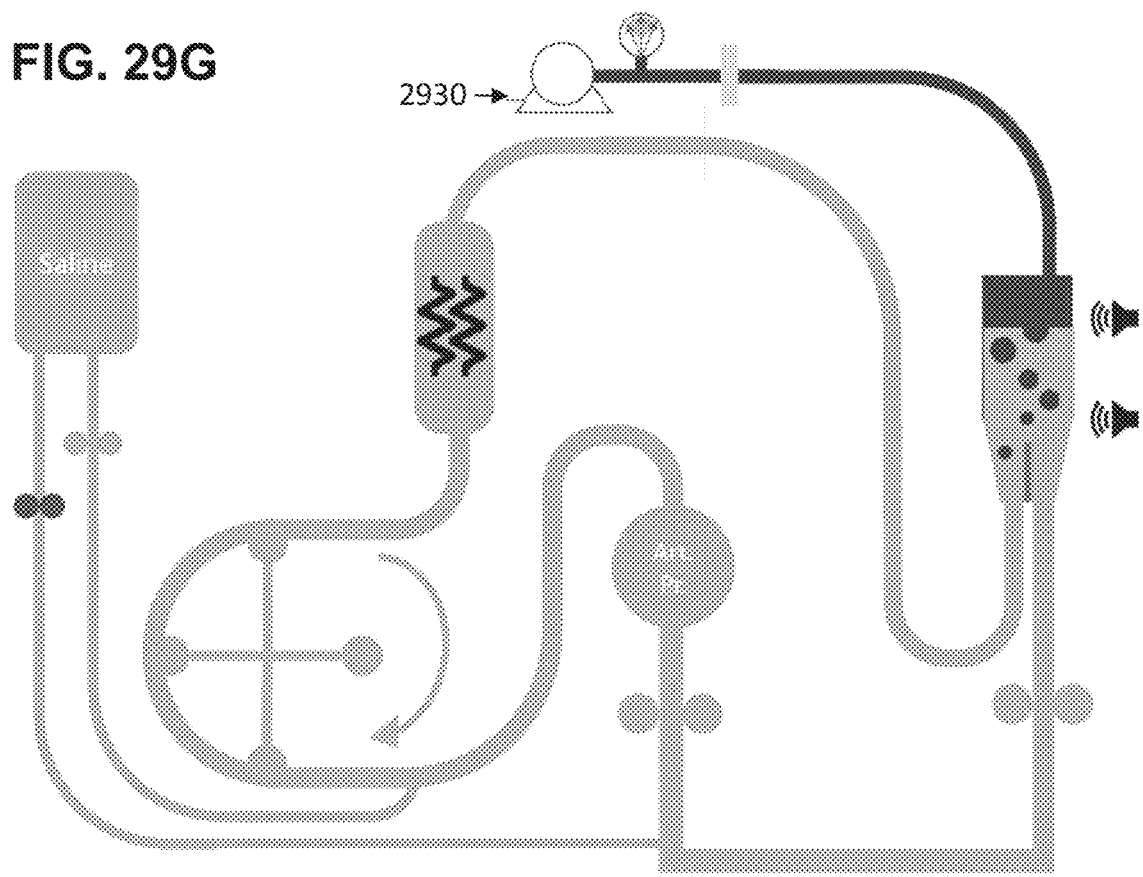

Referring now to FIG. 29E, the first and second saline pinch valves can both be closed, and the blood pump 2902 can be operated in a "forward" direction (e.g., the same direction as during dialysis therapy) while the air pump 2928 continues to operate. This causes the fluid level to go down in the venous drip chamber, as indicted by arrow 2901. Next, as shown in FIG. 29F, the first saline pinch valve 2920 can be opened and the venous pinch valve 2926 can be closed, while the blood pump and air pump continue to operate, to cause the fluid level to rise again in the patient tubing set. This operation can continue until one or more of the level sensors detects fluid in the venous drip chamber. in the illustrated example, this operation continues until the upper level sensor 2918 detects fluid in the venous drip chamber. At FIG. 29G, the blood pump and air pump can continue to operate as in FIG. 29F, but the patient tubing set can be vented through vent 2930. This allows air bubbles to percolate out of the patient tubing set through the venous drip chamber.

Figure 29H:
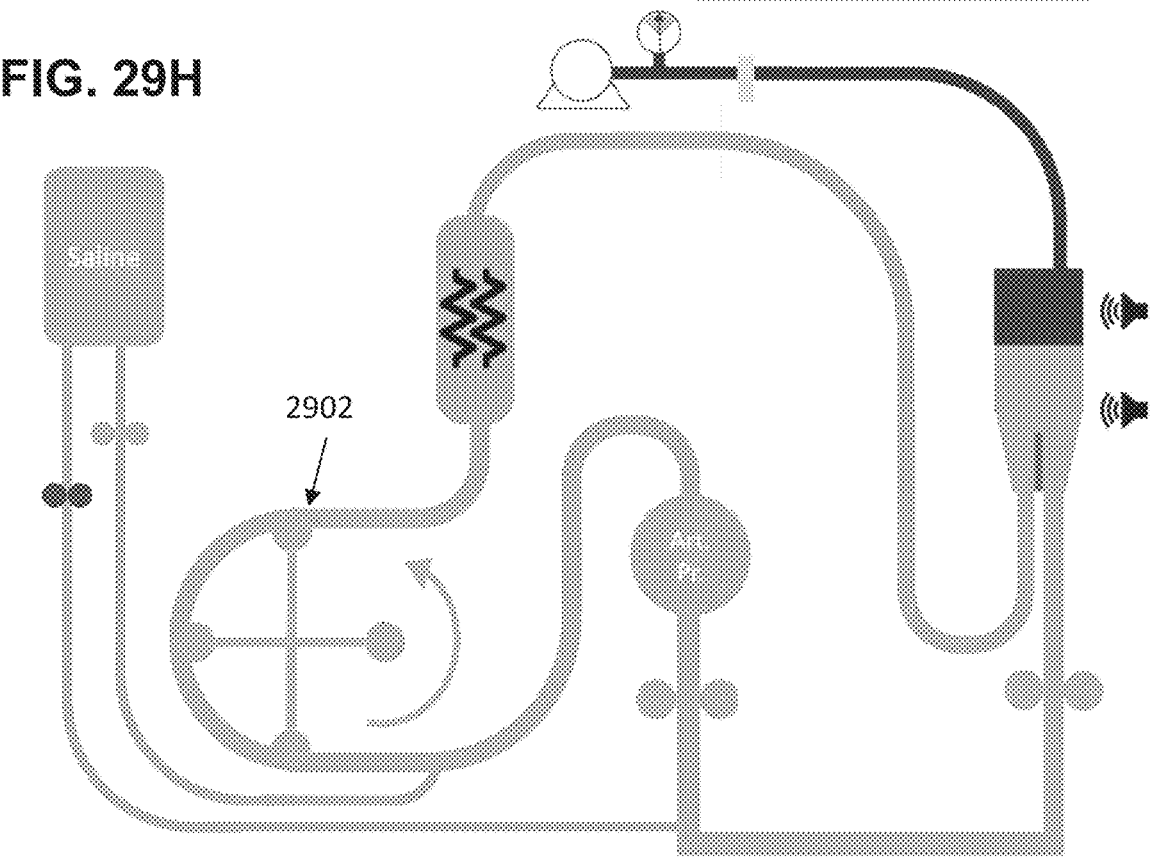
Figure 29I:
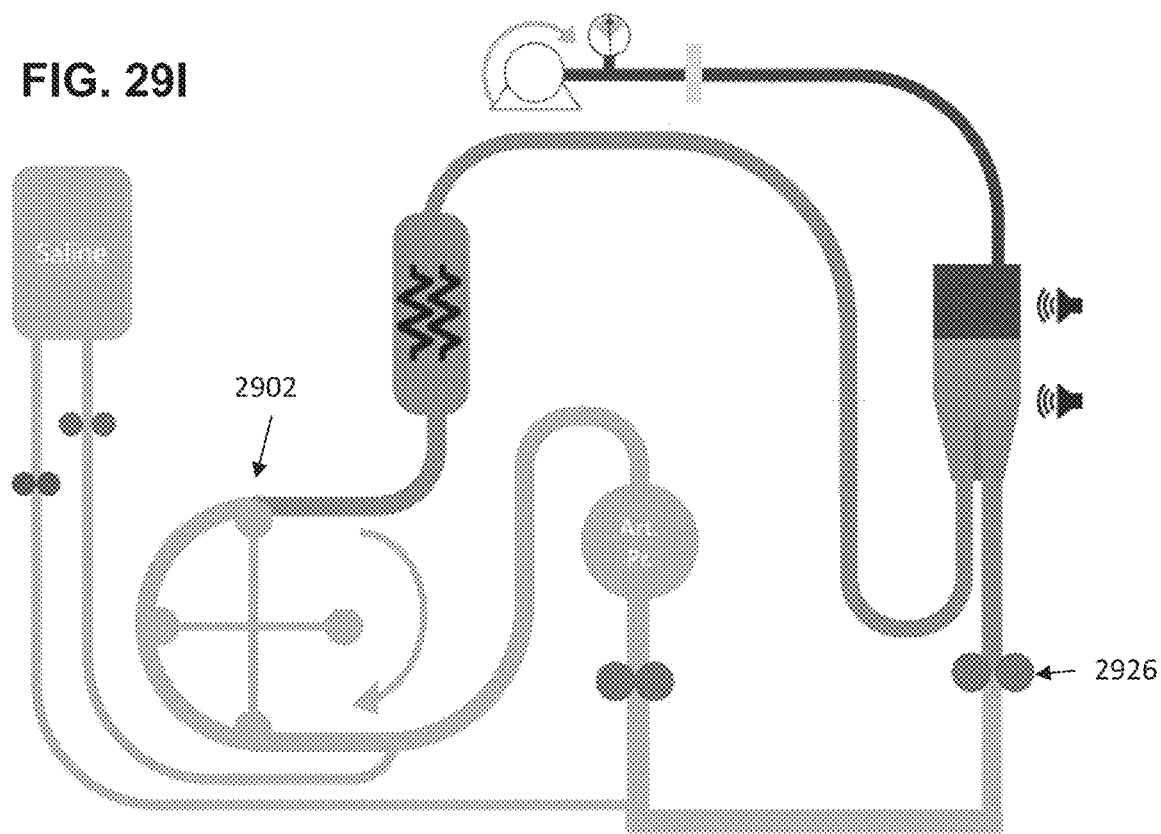
Figure 29J:
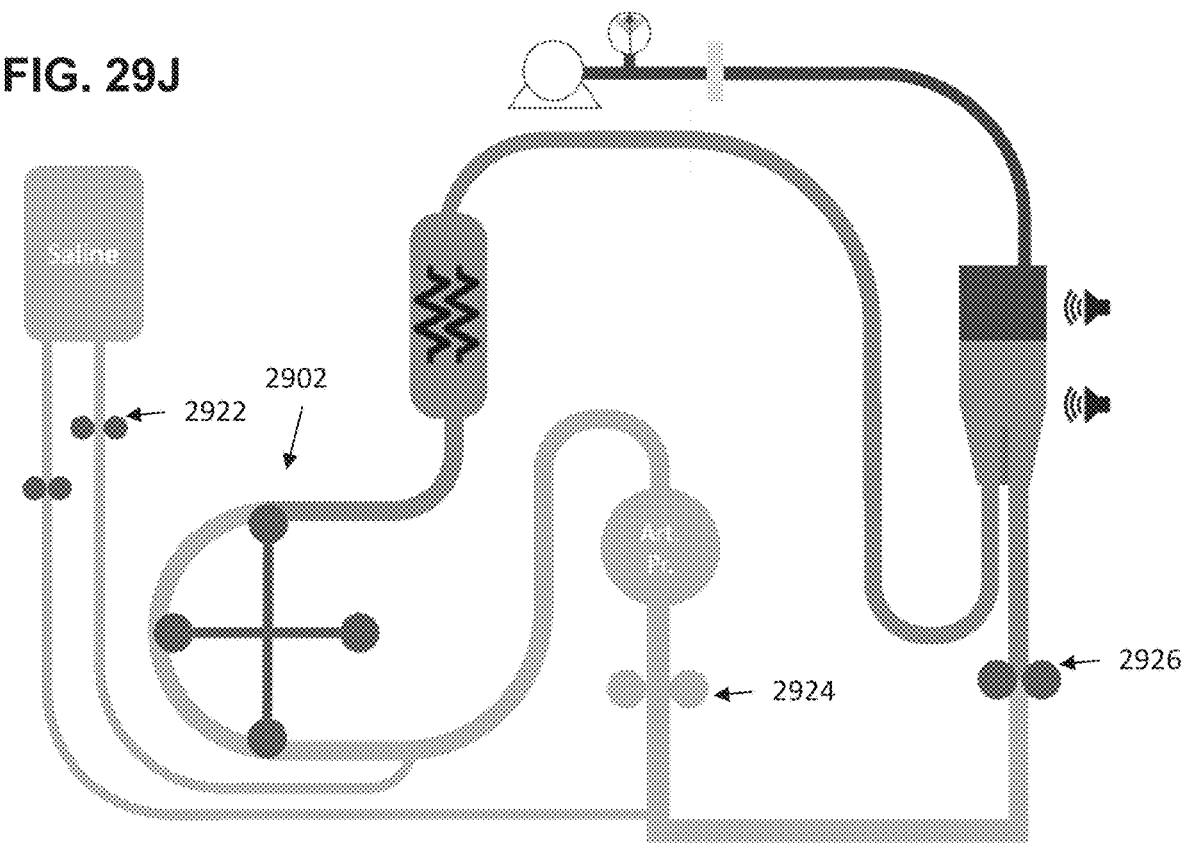

Next, as shown in FIG. 29H, the blood pump 2902 can be operated in a "reverse" direction (e.g., the opposite direction as during dialysis therapy) while the air pump 2928 continues to operate. This continues the process of priming the tubing set and filling every aspect of the tubing set with saline while removing and dislodging air bubbles from the tubing set.

Figure 29K:
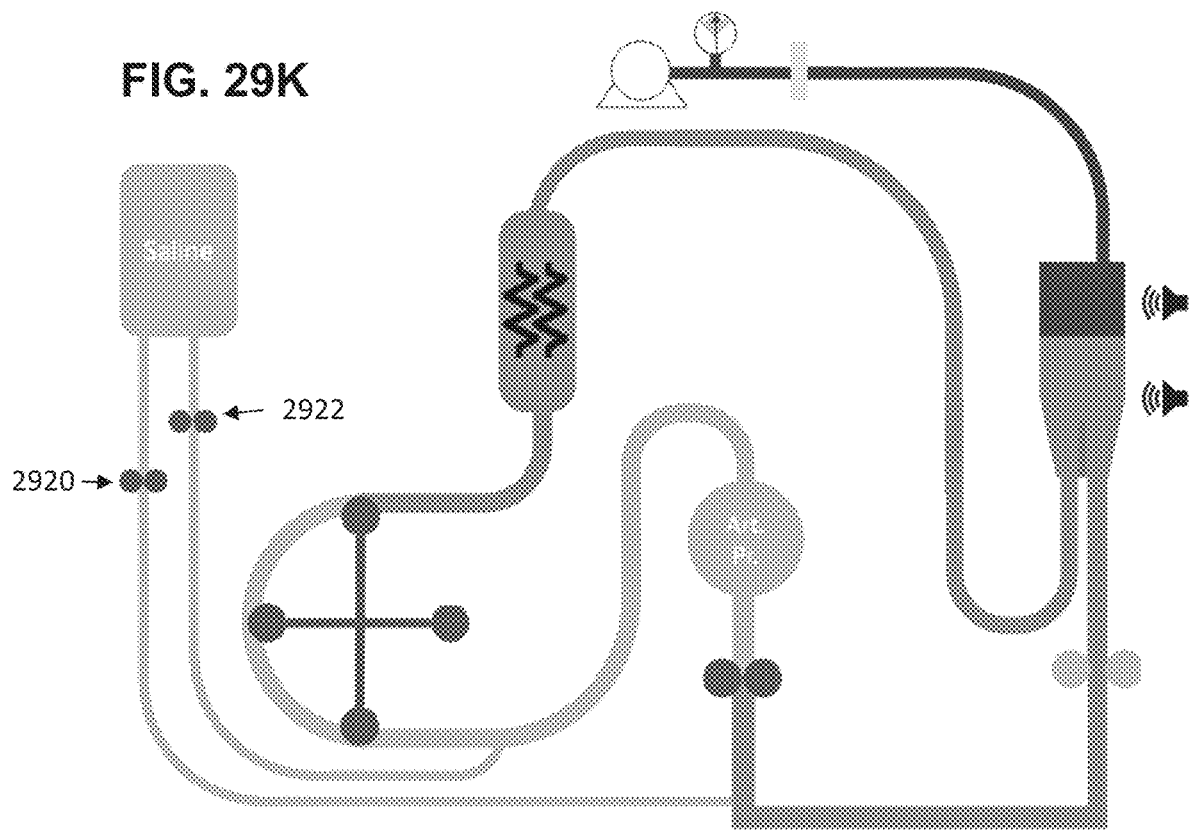
Figure 29L:
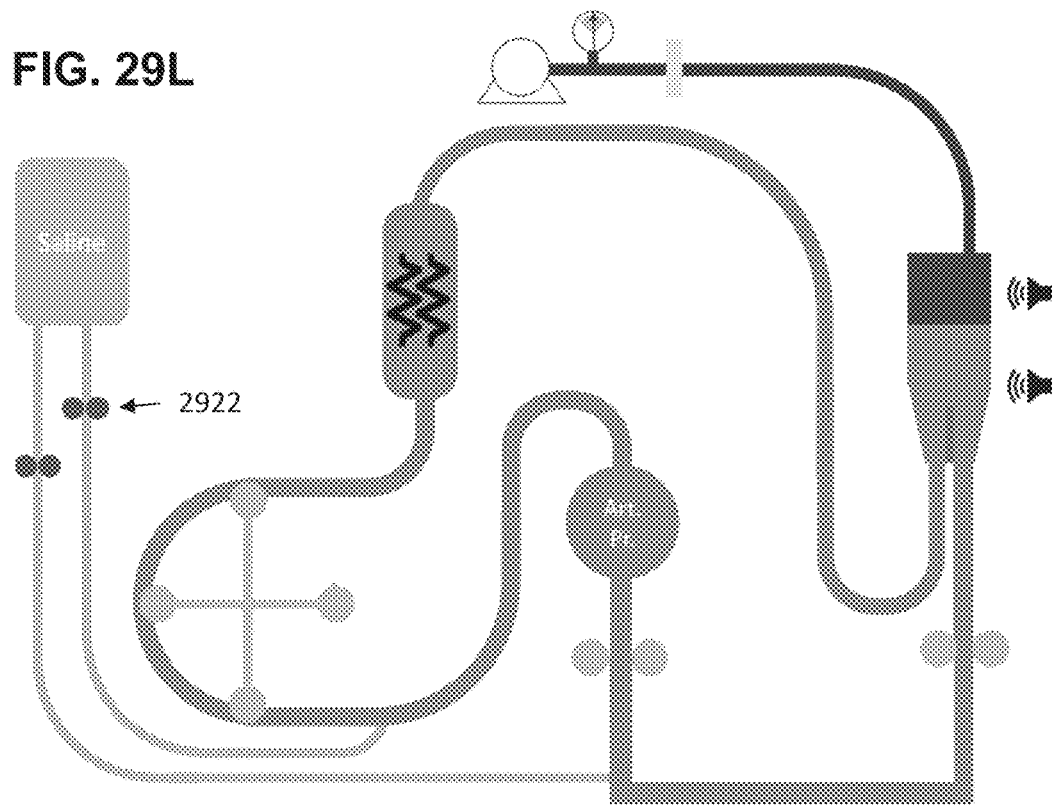

FIGS. 29I-29L illustrate one embodiment that includes pressure testing individual segments of the patient tubing set after the priming sequence to identify localized leaks in the patient tubing set. The pressure testing sequence can include the steps of sequentially opening and closing various pinch valves and changing the operation of the blood pump to evaluate different segments of the patient tubing set. For example, in FIG. 29I, all pinch valves can be closed, and the blood pump can continue to operate in the "forward" operating mode. This pressurizes the segment of the patient tubing set between the blood pump 2902 and the venous pinch valve 2926. Once the patient tubing set segment has been pressurized, the pressure within the patient tubing set segment can be measured and stored as a baseline pressurized value. Next referring to FIG. 29J, the blood pump 2902 can be turned off and the arterial pinch valve 2924 can be opened. Opening the arterial pinch valve 2924 exposes a new segment of the patient tubing set, between the blood pump and the venous pinch valve 2926, to the pressurized fluid from the first tubing set segment. The pressure within the patient tubing set can be measured again, and compared against the baseline pressurized value and have a pressure decay rate calculated. If the measured pressure at this step is lower than the baseline pressurized value, or exhibits a pressure decay rate above a certain threshold, it can indicate a leak in the patient tubing set between the blood pump and the venous pinch valve, including through saline pinch valve 2922. In FIG. 29K, the blood pump can be turned off and venous pinch valve 2926 can be opened. Opening the venous pinch valve 2926 exposes a new segment of the patient tubing set, between the venous pinch valve and the arterial pinch valve, to the pressurized fluid from the first tubing set segment. The pressure within this patient tubing set segment can be measured again, and compared against the baseline pressurized value or have a pressure decay rate calculated. If the measured pressure at this step is lower than the baseline pressurized value or exhibits a pressure decay rate above a certain threshold, it can indicate a leak in the patient tubing set between the venous pinch valve and the arterial pinch valve, including through saline pinch valve 2920. Finally, in FIG. 29L, the arterial pinch valve can be opened and the blood pump can be operated again. The measured pressure at this step can be compared to the baseline pressure, or be determined to exhibit a pressure decay rate above a certain threshold, to indicate a leak through saline pinch valve 2922.

After a priming sequence when saline is in the tubing set, the system can further run self-tests to check for leaks in the tubing set. In one embodiment, the pinch valve on the venous line can be closed with the blood pump running, and air can be pumped into the venous drip chamber. Next, the arterial pinch valve can be closed, and the venous pinch valve can be opened, and the system can check for pressure stabilization. If there is no pressure decay, it can be confirmed that there are no leaks in the system.

In one embodiment, the dialyzer can be flushed prior to beginning dialysis therapy with a patient. The system can be configured to flush the dialyzer with up to 500 ml of saline. Upon completion of the priming procedure, the used priming fluid may be discarded. Typically there have been two different types of destinations for the used priming fluid: 1) a receptacle or fluidic connection that leads to the inside the dialysis machine itself, which routes to a drain, or 2) an external receptacle, which is typically reusable and manually dumped into a sink and cleaned. Both of these approaches present challenges in terms of maintaining cleanliness and disinfection of surfaces, either internal or external. Additionally, often times the open end(s) of the tubing set that are used to interface with the disposal receptacle are the same ends which will later be connected to the patient during treatment. Infection control is of critical importance while performing hemodialysis treatments and setups, and exposing the open ends of the tubing set during the prime discard procedure presents an infection risk, especially since the tubing set must be handled by a user to position it correctly for discarding the fluid.

As described above, the tubing set is filled with saline during the priming sequence. During this priming, the arterial and venous lines are attached to each other with union joint 256 as illustrated in FIG. 18. In a first prime discard embodiment, after the tubing set is primed, the patient can remove cap 258 from the union joint 256 and position the union joint over a waste bucket. The dialysis system can then be placed into a prime discard sequence, which first confirms that valves 180b and 180c (from FIG. 17) are closed, and that valves 180a and 180d (from FIG. 17) are open. The blood pump can be operated in a forward direction to draw saline into the tubing set until the desired prime discard amount is pumped through the system and drained though the union joint 256 of FIG. 18. Next, valve 180d is closed, valve 180C is opened, and the saline is allowed to be gravity drained through the union joint until the proper amount of saline feeds out of the union joint (e.g., 40 ml of saline in one embodiment).

Figure 19A:
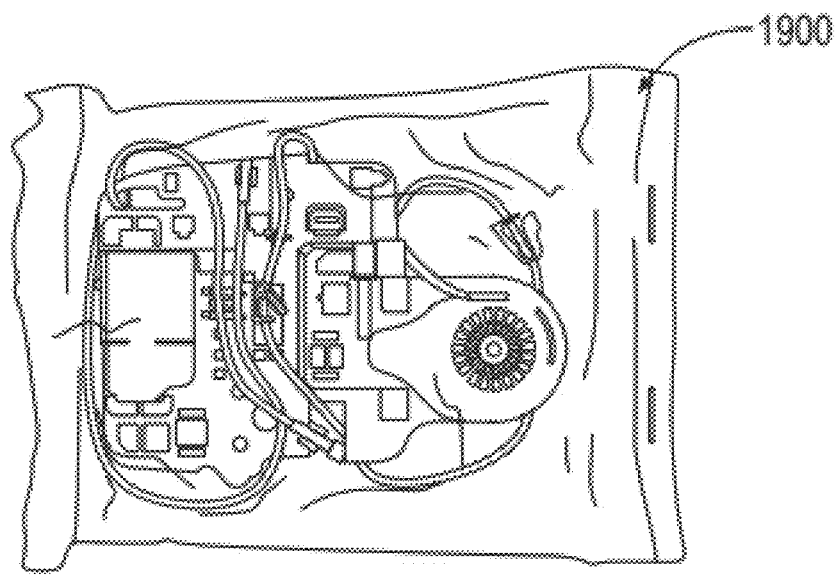
FIGS. 19A, 19B and 19C illustrate one embodiment of a discard receptacle for discarding of priming saline following a priming sequence.

In another prime discard embodiment, the sterile packaging for the cartridge and tubing set can also be used as a discard receptacle after priming. The cartridge and tubing set is supplied sterile, and is typically packaged in a disposable pouch which serves as a sterile barrier. In a first configuration, shown in FIG. 19A, a sterile receptacle 1900 is used as the sterile packaging to ship and maintain sterility of the cartridge and tubing set prior to treatment. In a second configuration, shown in FIG. 19B, the sterile receptacle 1900 serves as a disposable prime discard receptacle for drainage of priming saline. In operation, a user removes the cartridge and tubing set from the sterile pouch, which will later serve as the prime discard receptacle. The cartridge and tubing set can be connected the dialysis machine, including to a saline source and dialyzer, as described above. The arterial and venous lines of the cartridge and tubing set can be pre-connected to the union joint, and the cartridge and tubing set are primed with saline, as described above. After priming the tubing set, the user can attach the sterile receptacle to the dialysis system, remove the cap from the union joint, and allow the dialysis system to displace saline from the tubing set into the sterile receptacle 1900. Saline is allowed to flow through both the arterial and venous lines into the receptacle since they both meet at the union joint. After the prime discard is completed, the user removes the sterile receptacle and for disposal. Finally, the user disconnects the union joint from the arterial/venous lines, connects the lines to the patient's access site(s), and disposes of the union joint. At this point, dialysis treatment is ready to begin.

Figure 19B:
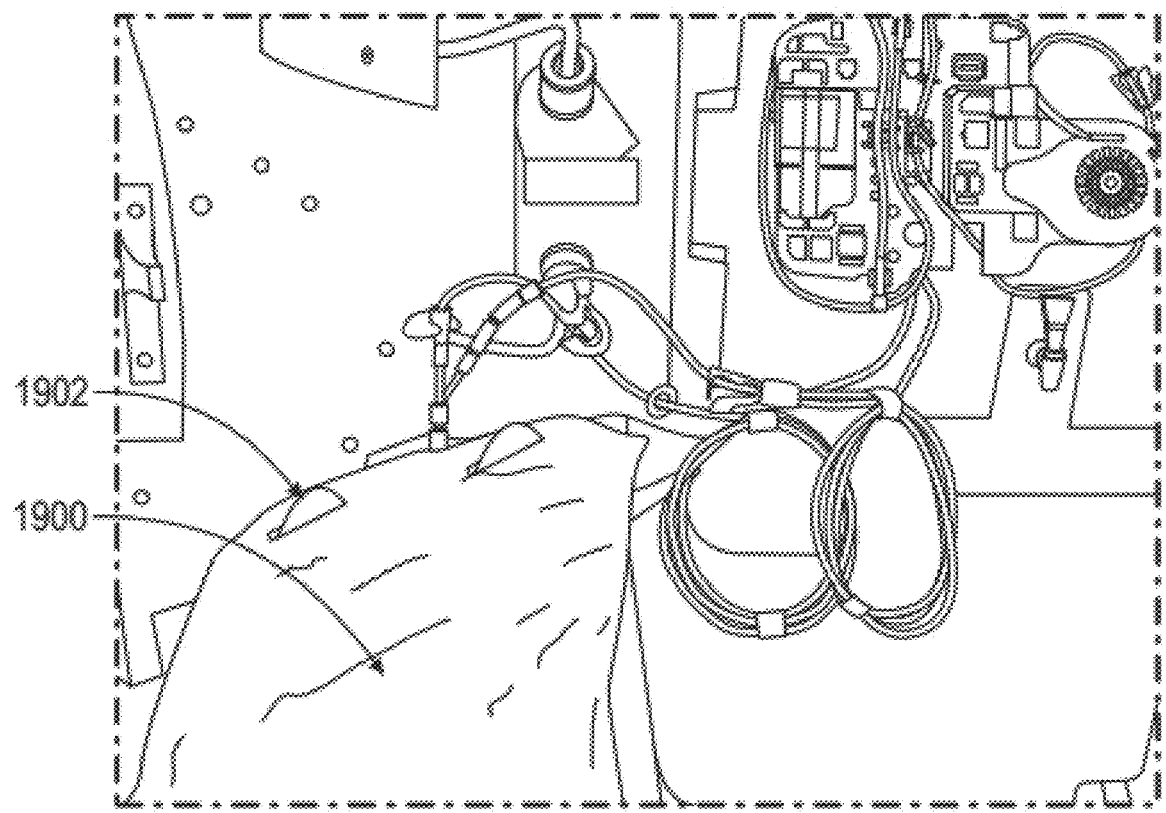

The sterile receptacle 1900 can include mounting features 1902, shown in FIG. 19B, such as cutouts, tabs, or other mounting features to interface with the dialysis system to hold the receptacle in place during prime discard. For example, in one embodiment the mounting features 1902 comprise cutouts, and the dialysis system comprises tabs that extend through the cutouts to hold the receptacle on the dialysis system.

Additionally, the dialysis system can include mounting features to hold the union joint in place on the dialysis system relative to the mounted receptacle. The mounting features on the dialysis system may include snap fit features, spring grip features, semicircular cup features, hole and shaft features, or any other similar mounting features. For example, the receptacle may include linear slits cut into one of the sheets which interface with linear extrusions which are hook-shaped in cross section located on the dialysis system. In one specific example, these hook-shaped features may be mounted on surfaces which are not co-planar with one another but meet at a slight angle, such that the hook-shaped features impose a slight curvature on of the sheets on the pouch. This would force the other sheet that is welded to the first sheet at its edges into an opposite curvature, enlarging the opening between the sheets at the top of the pouch.

Figure 19C:
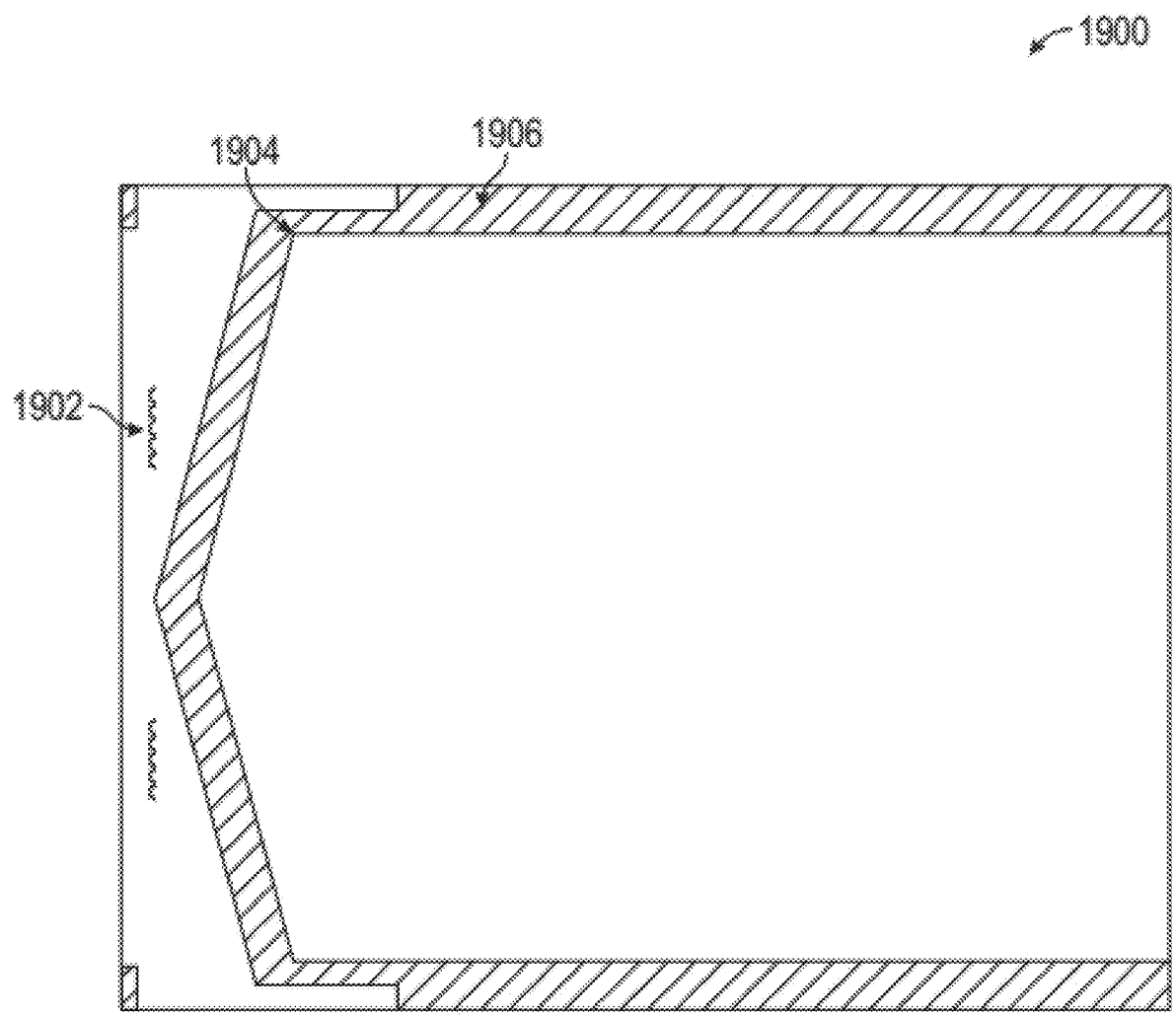

In some embodiments, the sterile receptacle may be constructed of two thin sheets welded together at the edges, which may be opened by de-laminating the weld at one edge of the pouch. If a user were to completely delaminate both sheets, the pouch could not be used as a prime discard receptacle because it would not be able to hold any liquid volume. FIG. 19C shows an engineering drawing of the sterile receptacle 1900, including mounting features 1902, first welds 1904, and second welds 1906. In this embodiment, the welding of the two sheets is configured such that the user is able to open the pouch to remove its contents while preventing the user from opening the pouch to such an extent that it would not be able to hold enough volume to serve as a discard receptacle. As shown, the first welds 1904 along the side of the receptacle may be thin up until a point, and then becomes much thicker, as shown by second welds 1906, such that the resistance to opening the pouch past the resistance point may be much higher. This ensures that the user is able to open the receptacle to remove the cartridge and tubing set, but still be able to use the receptacle for the prime discard saline.

Figure 26:
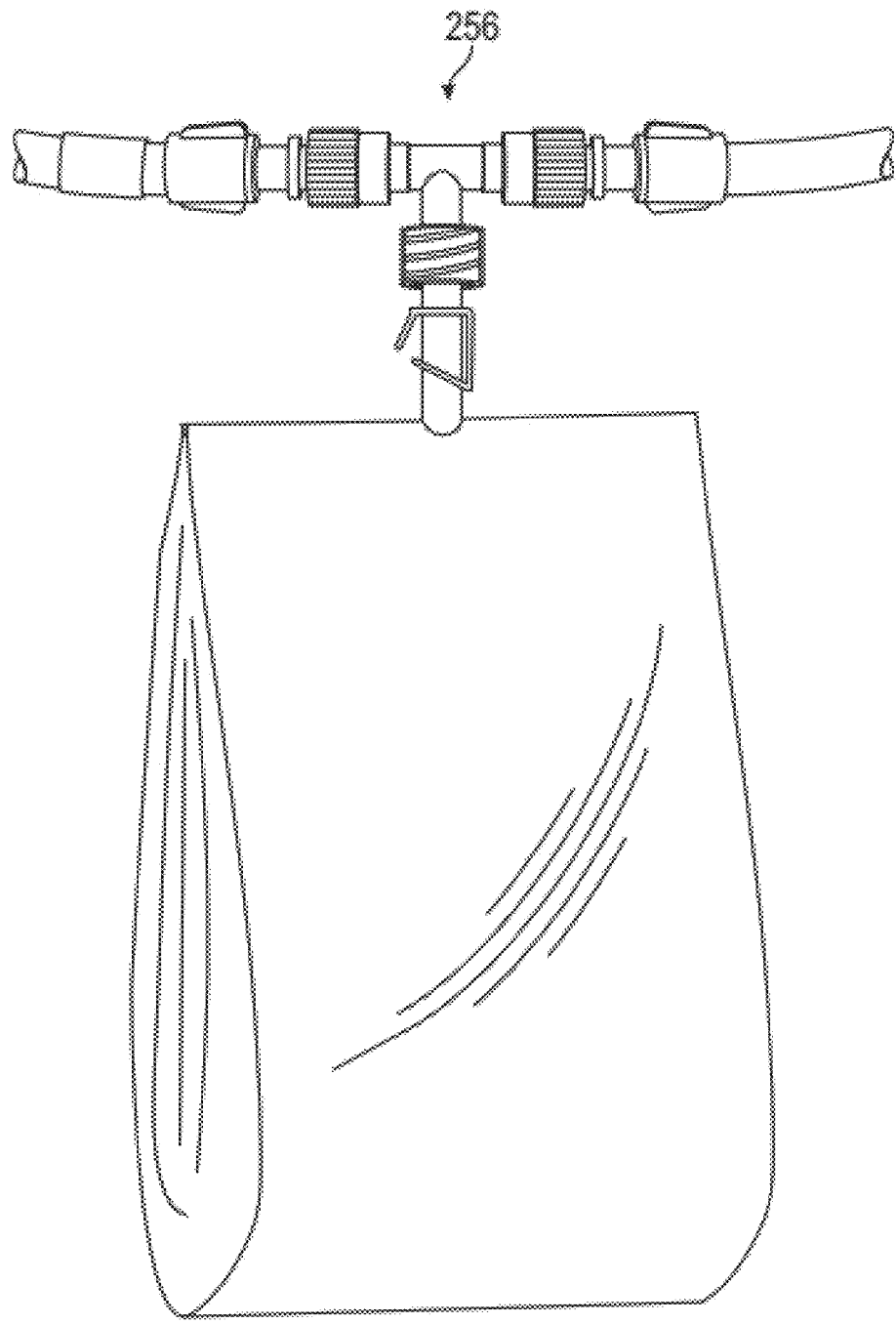
FIGS. 26 and 27 show embodiments of a receptacle for discarding the priming fluid.

An alternative embodiment, as shown in FIG. 26, can include a cartridge and tubing set that has a receptacle that is pre-attached to the tubing set (i.e., not the sterile receptacle that it ships in). The embodiment can include a union joint 256, as described above, that includes connections to the patient lines as described above. The embodiment can optionally include a clip as shown to secure the receptacle and patient lines onto the console during treatment. In this embodiment, the user can attach and detach the patient lines to vascular access without needing to manage the other side of the tubing.

Figure 27:
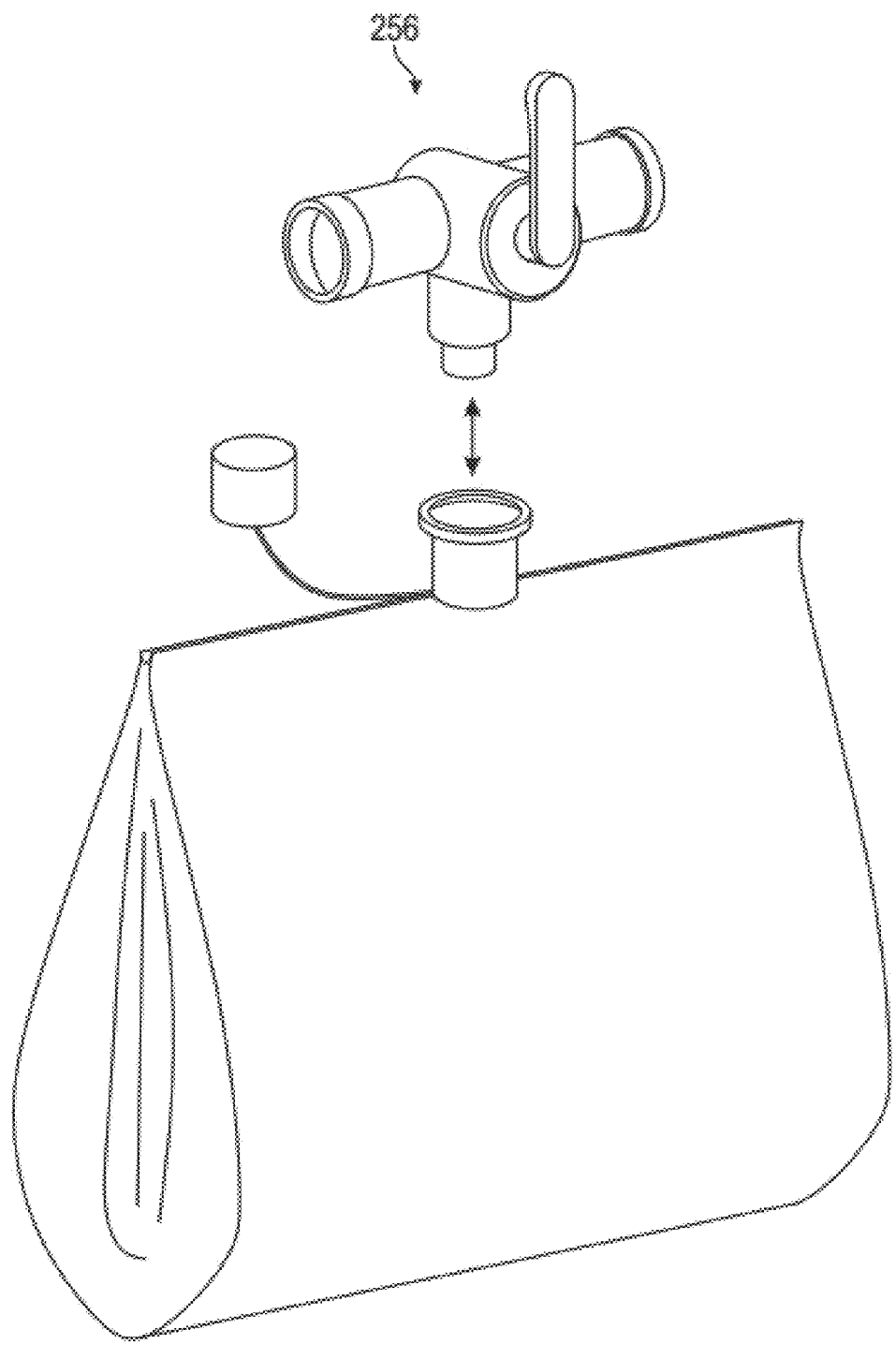

In yet another example as shown in FIG. 27, the union joint 256 can comprise a 3-way stopcock that includes two female luers that connect to the patient arterial and venous lines and a male luer that connects to a pre-attached discard receptacle. The union joint can be used to direct the flow of saline into the discard receptacle after a priming sequence. The receptacle can optionally include a floating cap on the bag to close and seal the bag after use.

In another embodiment, the pre-attached receptacle interfaces with a prime discard valve that is controlled by the dialysis system. In this embodiment, priming is performed as described above, and upon completion of priming the dialysis system can control the prime discard valve to route the priming saline into the pre-attached receptacle. Alternatively, the dialysis system itself could include a discard receptacle, and the tubing set could be configured to automatically discard into the discard receptacle via the prime discard valve at the completion of a priming sequence. In some embodiments, the connection between the discard receptacle on the dialysis system and the blood tubing set is automatically made when the blood tubing set is mounted onto the system, as is enabled by the organizer configuration described above. In these embodiments, flow from the blood tubing set into the discard receptacle can be controlled automatically by a pinch valve that engages the tubing of the blood tubing set connector. In further embodiments, the discard receptacle of the dialysis system is disinfected by the system's automatic disinfection sequences.

At the completion of a dialysis treatment, blood still remains inside the tubing set. The blood pump 213 can be controlled to draw saline into the tubing set to push the remaining blood back into the patient. This blood return mechanism can be highly controlled by the controller and blood pump of the system. For example, during dialysis therapy and blood return, the controller of the system can monitor and track the exact number of revolutions made by the blood pump when the pinch valves that control saline administration are open to know exactly how much saline has been pushed into the tubing set. The blood pump can then be stopped or de-activated when the desired volume of saline is drawn into the tubing set. This allows the system to know exactly how much saline has been used, and how much remains in the saline source or bag. At the end of the dialysis therapy, the amount of blood in the tubing set is known (typically around 250 ml), so the system can precisely meter the correct amount of saline into the tubing set to push the blood back into the user. The anticipated amount of saline to use for blood return (typically 300-600 ml depending on the varying degree of thoroughness of the blood return) can be integrated into the overall fluid removal target for ultrafiltration so that after the blood return the patient target weight is attained. If the needed amount of saline does not remain in the saline source prior to blood return, the system can alert the user that the saline source needs to be refilled or replaced.

In one embodiment, the dialyzer can be flushed prior to beginning dialysis therapy with a patient. In some cases, clinics ignore this labeling and do not flush the dialyzer. The system can be configured to flush the dialyzer with up to 1000 ml of saline.

The system can also automatically drain any fluid out of the dialyzer after a dialysis treatment. In one embodiment, the blood pump can be run in the reverse direction with the venous line clamped to pull fluid from the dialysate chamber of the dialyzer through the dialyzer microtube walls against gravity through the dialyzer and into the saline source or bag.

Figure 7:
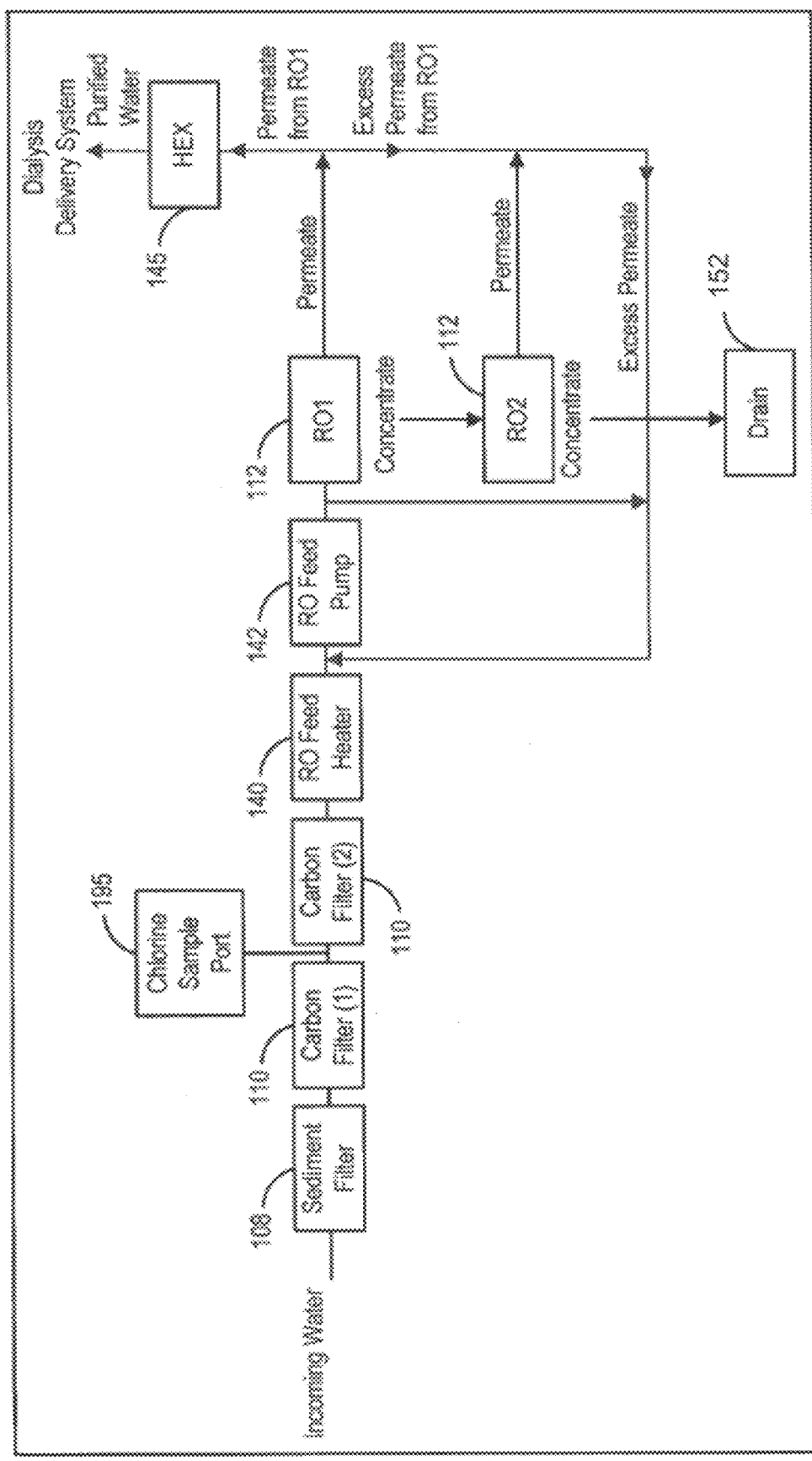
FIG. 7 shows a flow diagram of the water purification system contained within the dialysis system.

FIG. 7 shows a flow diagram of the water purification system 102 contained within the dialysis system 100. Incoming water, such as from the tap, can flow through a number of filters, including one or more sediment filters 108 and one or more carbon filters 110. A chlorine sample port 195 can be placed between the carbon filters 110 to provide samples of the fluid for measuring chlorine content. Redundant or dual carbon filters can be used to protect the system and the user in the event of a carbon filter failure. The water can then pass through a reverse osmosis (RO) feed heater 140, a RO feed pump 142, one or more RO filters 112 (shown as RO1 and RO2), and a heat exchanger (HEX) 144. Permeate from the RO filters 112 can be delivered to the HEX 144, while excess permeate can be passively recirculated to pass through the RO feed pump and RO filters again. The recirculation helps with operating of the water purification system by diluting the incoming tap water with RO water to achieve higher rejection of salts from incoming water. After passing through the HEX 144, the purified water can be sent to the dialysis delivery system 104 for preparing dialysate and assisting with dialysis treatments. Additionally, concentrate from the RO filters during the water purification process can be sent to drain 152.

Figure 8:
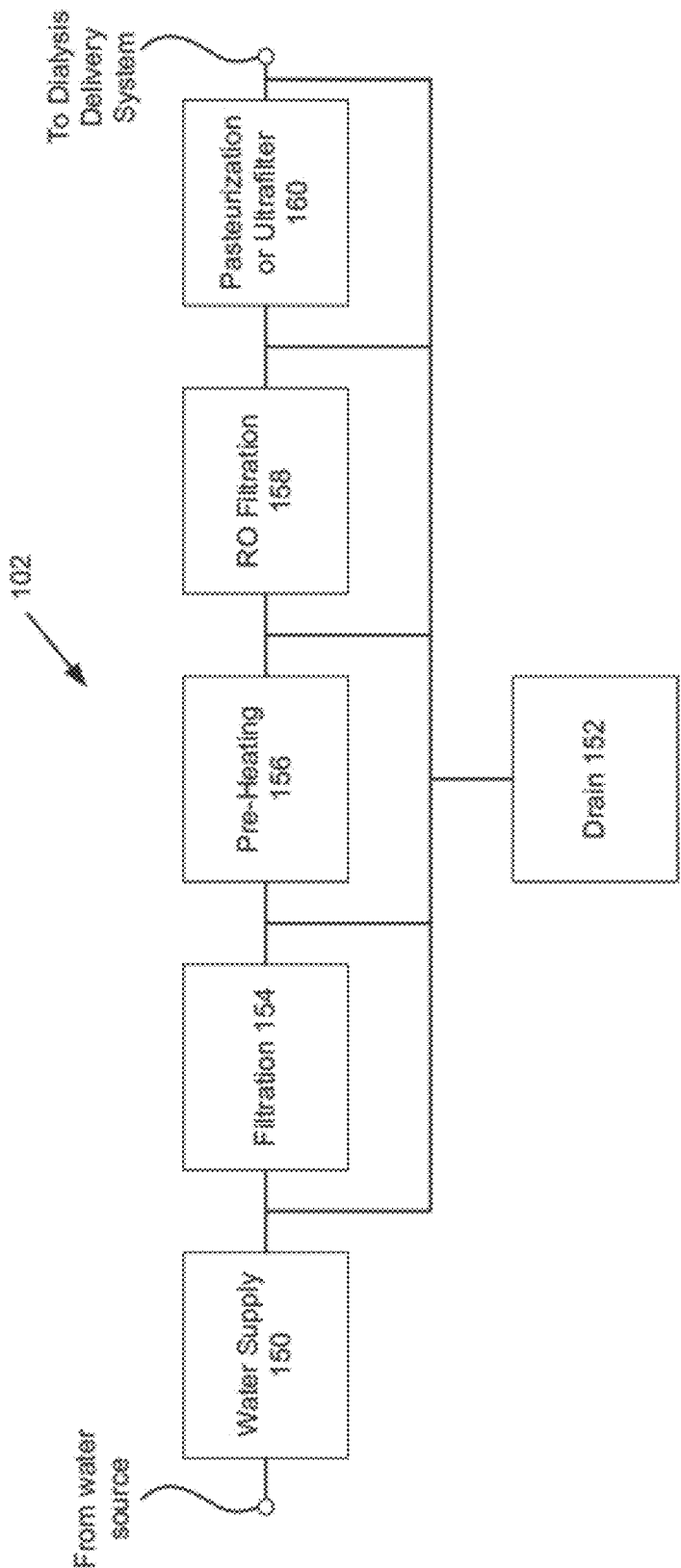
FIG. 8 is a schematic diagram showing a water supply subsystem, a filtration subsystem, a pre-heating subsystem, an RO filtration subsystem, and a pasteurization subsystem of the water purification system of the dialysis system.

Referring to FIG. 8, the water purification system 102 of the dialysis system can include one or more subsystems as described above in FIG. 7, including a water supply subsystem 150, a filtration subsystem 154, a pre-heating subsystem 156, an RO filtration subsystem 158, and a pasteurization or ultrafiltration subsystem 160. Each of the subsystems above can produce output to a drain 152. The water purification system 102 can be configured to purify a water source in real-time for dialysis therapy. For example, the water purification system can be connected to a residential water source (e.g., tap water) and prepare purified water in real-time. The purified water can then be used for dialysis therapy (e.g., with the dialysis delivery system) without the need to heat and cool large batched quantities of water typically associated with water purification methodologies.

Figure 9:
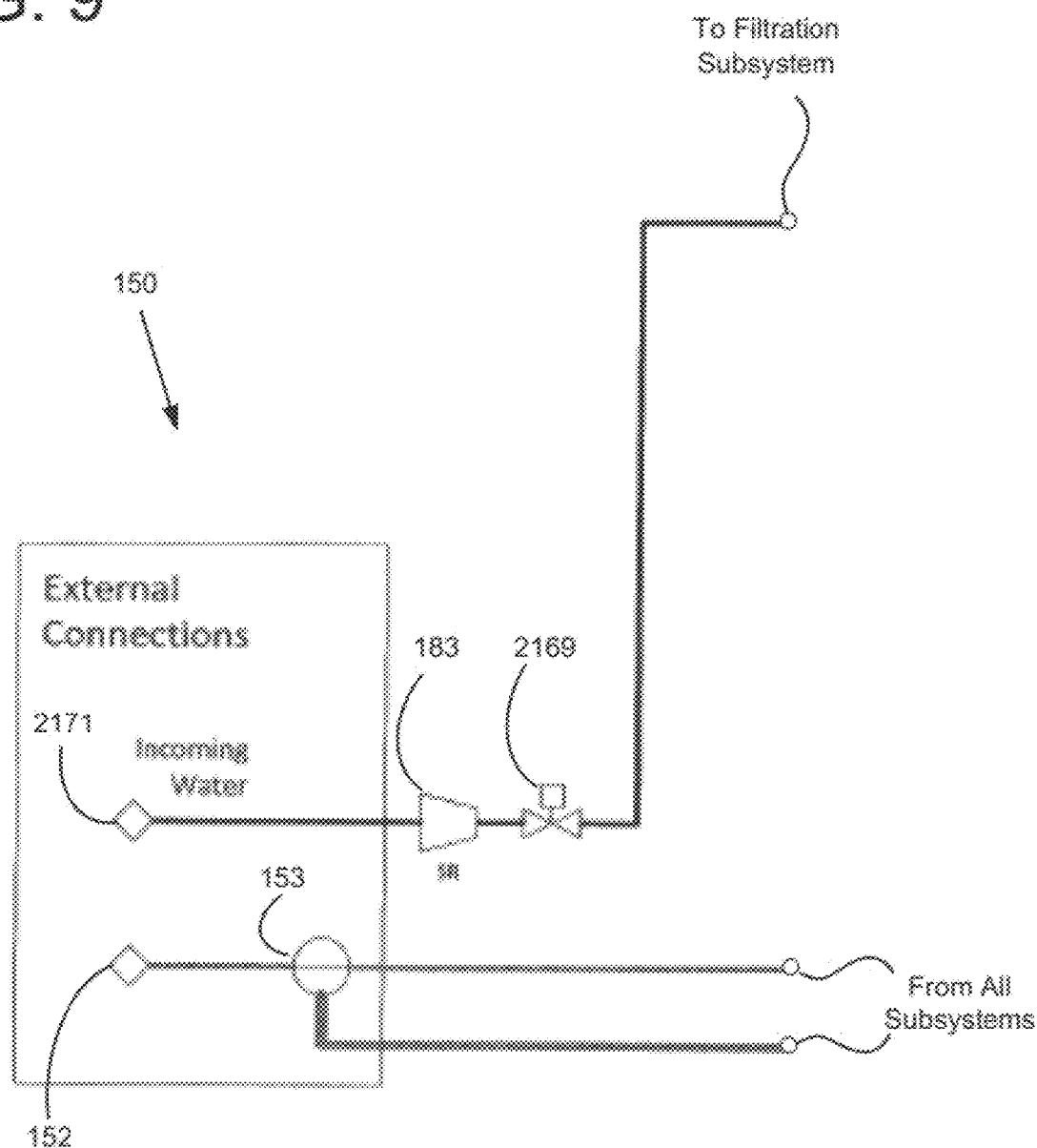
FIG. 9 shows the features of the water supply subsystem of the water purification system.

FIG. 9 shows the features of the water supply subsystem 150 of the water purification system, which can include a variety of valves (e.g., three-way valves, control valves, etc.) for controlling fluid flow through the water purification system. For example, at least one valve 2169 can be opened to allow water to flow into the water purification system for purification. The incoming water can flow in from a tap water source 2171, for example. Fluid returning from the water purification system can be directed to drain 152 through one or more of the valves. Furthermore, the subsystem can include a supply regulator 183 that can adjust the water supply pressure to a set value. A drain pressure sensor 153 can measure the pressure at the drain. Water can flow from the water supply subsystem 150 on to the filtration subsystem, described next.

Figure 10:
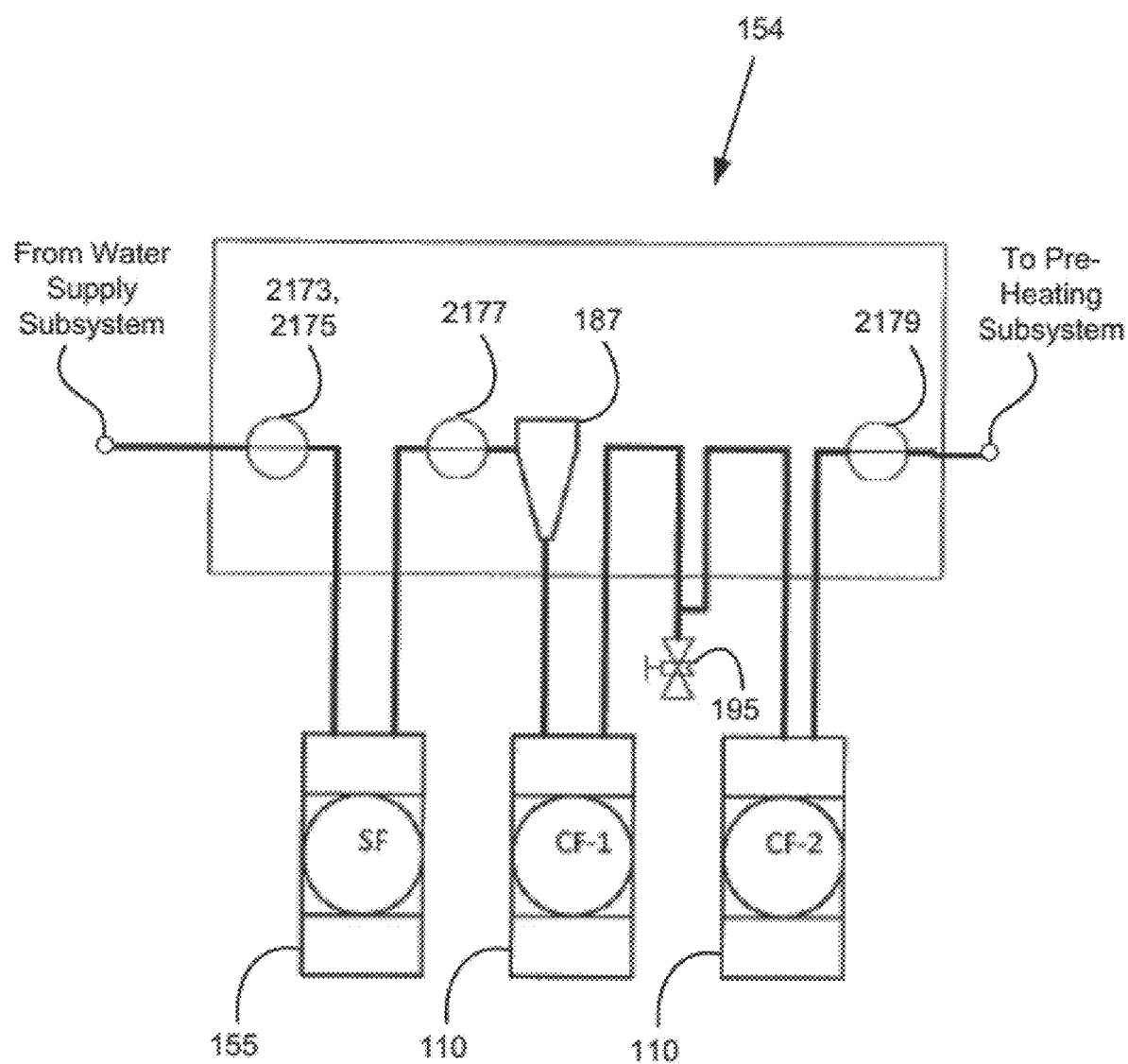
FIG. 10 shows one embodiment of a filtration subsystem of the water purification system.

FIG. 10 shows one embodiment of a filtration subsystem 154 of the water purification system. The filtration subsystem can receive water from the water supply subsystem 150 described in FIG. 9. Water can first pass through a supply pressure sensor 2173 configured to measure the water pressure and a supply temperature sensor 2175 configured to sense the temperature of the incoming water supply. The filtration subsystem can include a sediment filter 155, for example, a 5-micron polypropylene cartridge filter. The filter typically requires replacement every 6 months. Based on the high capacity of the sediment filter and the relatively low flow rate through the filter, the life expectancy is estimated to be over 1 year based on the average municipal water quality in the US. A replacement interval of 6 months provides high assurance that premature sediment filter fouling should be rare. Also, expected to be a rare occurrence based on the construction and materials of the filter is a failure that results in unfiltered water passing through the filter. A post-sediment pressure sensor 2177 can measure the pressure drop across the sediment filter to monitor and identify when the sediment filter needs to be replaced. Should the sediment filter allow unfiltered water to pass the result would be fouling of the carbon filters which would be detected by a pressure drop at post-sediment pressure sensor 2177. If this pressure drop is the significant factor when the sensor drops to 5 psig, the system will require replacement of both the carbon filters and the sediment filters prior to initiating therapy.

The water can then flow through one or more carbon filters 110 (shown as CF-1 and CF-2) configured to filter materials such as organic chemicals, chlorine, and chloramines from the water. For example, the carbon filters 110 can include granulated carbon block cartridges having 10-micron filters. The carbon filters can be connected in series with a chlorine sample port 195 positioned in the flow path between the carbon filters. The chlorine sample port can provide a user with access (such as through the front panel of the system) to the flowing water such as for quality control purposes to ensure the total chlorine concentration level of the water is below a certain threshold (e.g., below 0.1 ppm). Additionally, a post-carbon pressure sensor 2179 can be placed after the carbon filter(s) to monitor the fluid pressure in the line after the sediment and carbon filtration. As is also shown in FIG. 10, an optional air separator 187 can be placed between the sediment filter and the carbon filter(s) to remove excess air and bubbles from the line. In some embodiments, each carbon filter can specified to have a service life of 2500 gallons producing water that has less than 0.5 ppm of free chlorine and chloramine when operating in high chlorine conditions and at a higher flow rate than the instrument supports so an expected life of greater than 2500 gallons is expected. Based on a maximum treatment flow rate of 400 mL/min through the carbon filters the expected for a single carbon filter is approximately 6 months to a year or more depending on incoming water quality. The system typically requires replacement of both filters every 6 months. Most carbon filters cannot tolerate heat or chemical disinfection, therefore a recirculation/disinfection fluid path, implemented by the water supply and drain systems, does not include the carbon filters (or the sediment filters). Since the chlorine absorption capacity of carbon filters is finite and dependent on the incoming water quality, a water sample from the chlorine sample port 195 can be taken to verify that the water has a free chlorine concentration level of less than 0.1 ppm. Using the two stage carbon filtration and verifying the "equivalent absence" of free chlorine after the first carbon filter ensures that the second carbon filter remains at full capacity in complete redundancy to the first. When the first carbon filter does expire, both filters are typically replaced. Water can flow from the filtration subsystem to the pre-heating subsystem, described next.

Figure 11:
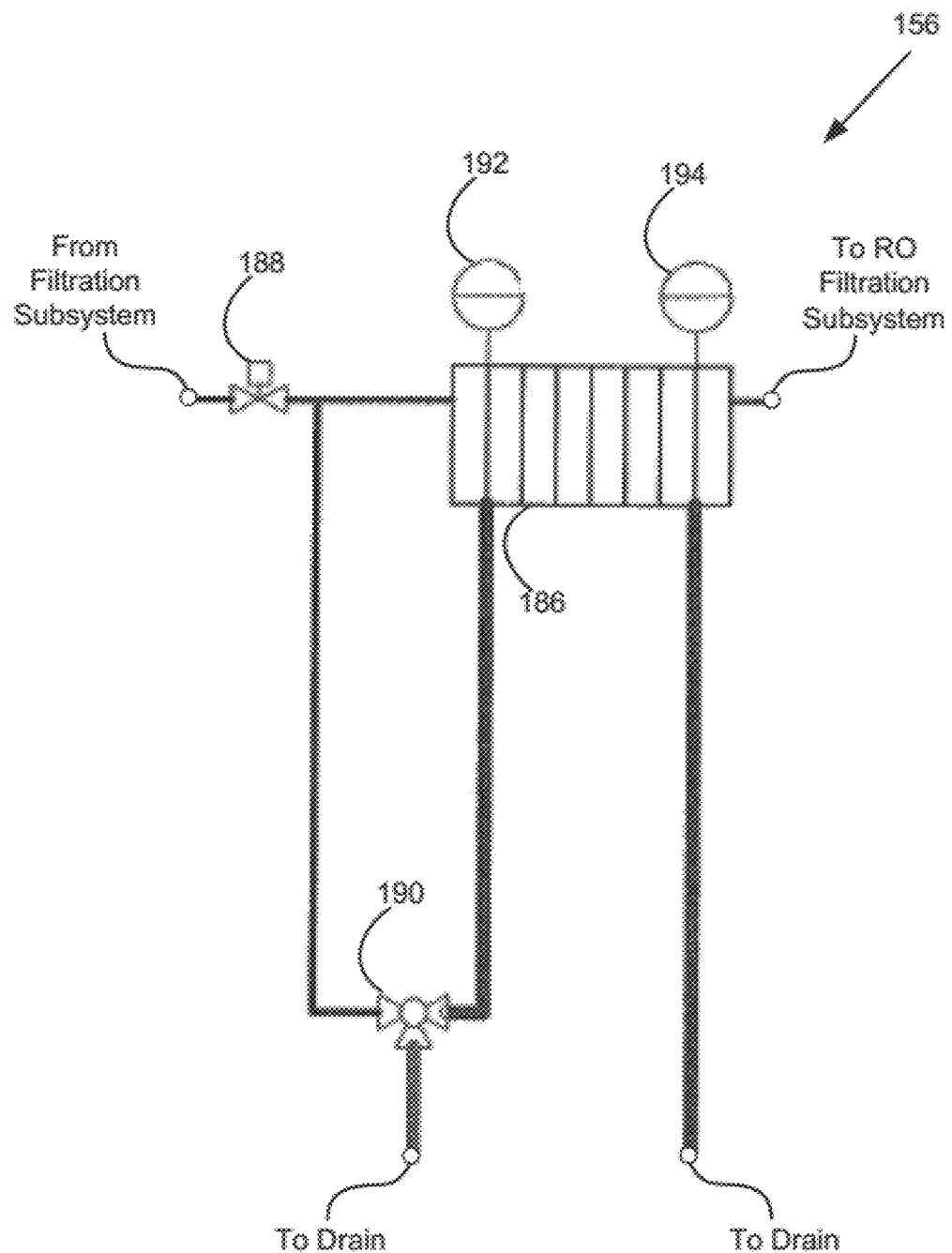
FIG. 11 shows one embodiment of a pre-heating subsystem of the water purification system.

FIG. 11 shows one embodiment of a pre-heating subsystem 156 of the water purification system. The pre-heating subsystem can be configured to control the temperature of water in the line to optimize RO filtration performance. The pre-heating subsystem can include one or more RO feed heaters 186, which can comprise, for example a thermoelectric device such as a Peltier heater/cooler. The RO feed heater 186 can be configured to regulate or adjust the temperature of the water before RO filtration. In one embodiment, the target temperature for reverse osmosis is 25 degrees C. for optimal RO filter performance. If the water is too cold the RO filters will have insufficient flow and the system will not make enough water. If the water is too warm the RO filters will allow more flow but also have reduced salt rejection. In one embodiment, 25° C. is the point at which flow and rejection are balanced to provide sufficient water volume with adequate rejection. The RO feed heater can be used to both heat or cool the fluid flowing through the heater. For example, in some embodiments, the RO feed heater can recover heat from waste water or used dialysate by way of the Peltier effect. In other embodiments, such as during a heat disinfect cycle, the RO feed heater can be placed in opposing polarity to negate Peltier effects. During water treatment, the incoming water flows through a titanium plate attached to the hot side of two thermoelectric wafers of the RO feed heater. Waste water can be directed through a separate titanium plate attached to the cold side of the wafers. Heat is therefore pumped from the waste water to the incoming water via the Peltier effect. At maximum power when the preheating system achieves a coefficient of performance of two, meaning half of the power heating the incoming water is recovered from waste water and the other half is from the electrical heating of the wafers. At lower power levels the coefficient of performance is higher meaning a higher percentage of the heat is recovered from the waste stream. During heat disinfect the thermoelectric wafers of the RO feed heater can be placed in opposing polarity. In this way both titanium plates are heated and the Peltier effect is negated. This ensures that the water is heated only and is always above the incoming temp on either side of the heater.

As shown in FIG. 11, the pre-heating subsystem 156 can include a process supply valve 188 in the line between the filtration subsystem and the RO feed heater, and a used dialysate return valve 190 for routing used dialysate to the drain. The RO feed heater can include a pair of temperature sensors 192 and 194 to measure the temperature of the fluid on either side of the heater. Water can flow from the pre-heating subsystem to the RO filtration subsystem, described next.

Figure 12:
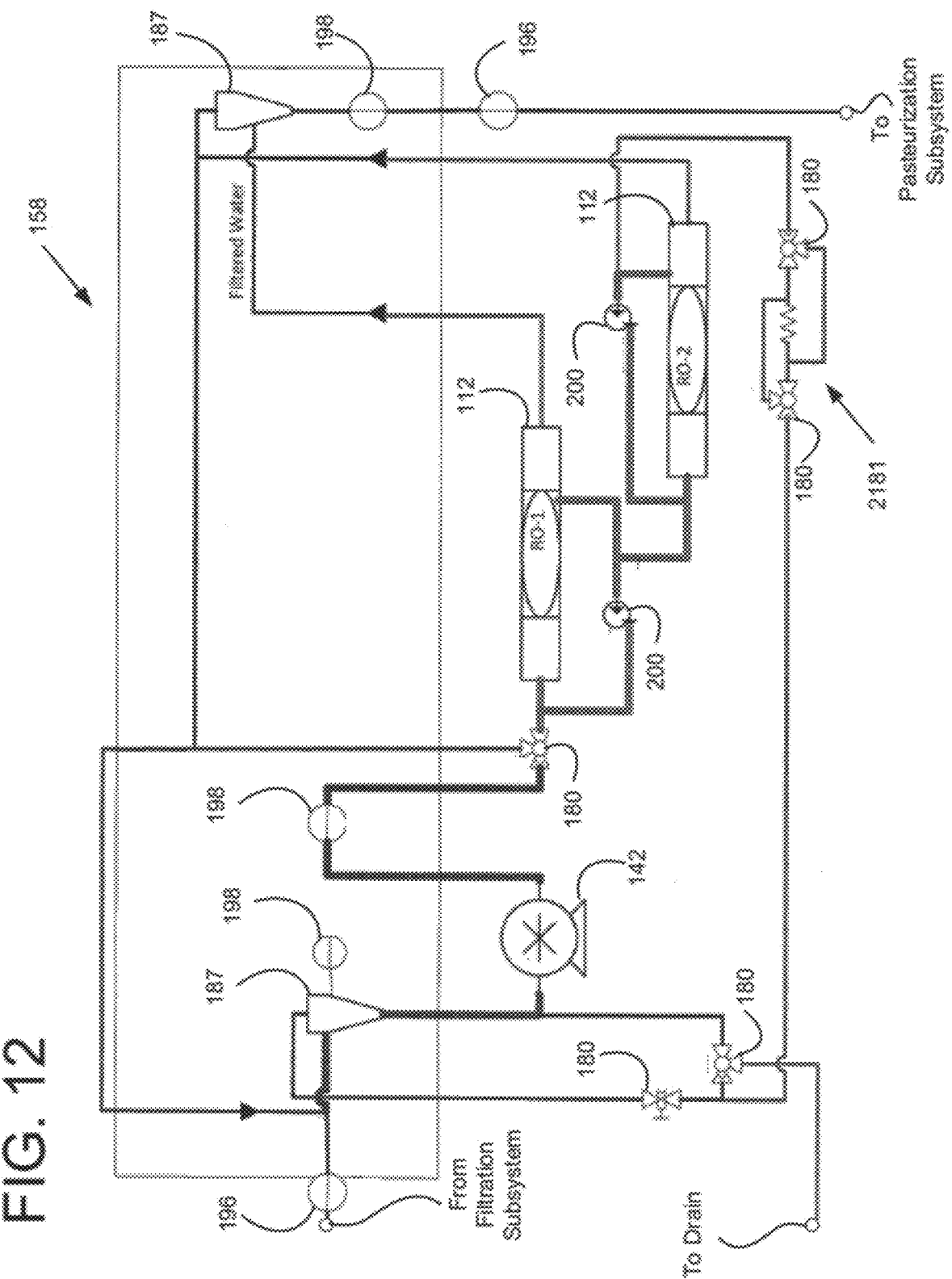
FIG. 12 shows one embodiment of a RO filtration subsystem of the water purification system.

FIG. 12 shows one embodiment of a RO filtration subsystem 158 of the water purification system. The RO filtration subsystem can receive pre-heated water from the pre-heating subsystem described above. The RO filtration subsystem can include a RO feed pump 142 that can drive water across one or more RO filters 112 (shown as RO-1 and RO-2) to produce a permeate flow and a concentrate flow. The concentrate flow can be filtered by more than one RO filter. In addition, the permeate flow can be combined with excess permeate and be recirculated back to blend with incoming water. In addition, each RO filter 112 can include a recirculation pump 200 to keep fluidic line flow velocity high over the RO filters. The recirculation pumps can run at a constant velocity, driving any flow emanating from the concentrate flow back into the inlet of the RO filters. Using a separate recirculation pump instead of recirculating through the RO feed pump lowers overall power consumption and keeps flow velocity over the RO membranes high to reducing fouling and allow for high water production rates. In some embodiments, the RO feed pump can be high pressure but relatively low flow pumps compared to the recirculation pump(s), which can be low pressure but high flow pumps.

The pressure created by the RO feed pump and a RO concentrate flow restrictor 2181 can control the flow rate of waste to the drain. To ensure that the restriction does not become fouled or plugged, the flow through the RO concentrate flow restrictor can be periodically reversed by actuating valves 180. In addition, to improve filter life and performance, recirculation pumps can be used to increase fluid flow rate in the RO filter housings. This increase in flow rate can serve to reduce a boundary layer effect that can occur near the surface of RO filters where water near the filter membrane may not flow. The boundary layer can create an area with a higher concentration of total dissolved solids that can build up over the surface of the RO filter and may collect and foul the RO filter.

The RO filtration subsystem can include on or more conductivity sensors 196 configured to measure the conductivity of water flowing through the subsystem to measure solute clearance, or per, pressure sensors 198 configured to monitor fluid pressures, and air separators 187 configured to separate and remove air and air bubbles from the fluid. Additionally, the RO filtration subsystem can include a variety of valves 180, including check valves, and fluid pumps for controlling flow through the RO filters and on to the pasteurization subsystem, back through the RO filtration subsystem for further filtration, or to the drain. Water can flow from the RO filtration subsystem to the pasteurization subsystem, described next.

Figure 13:
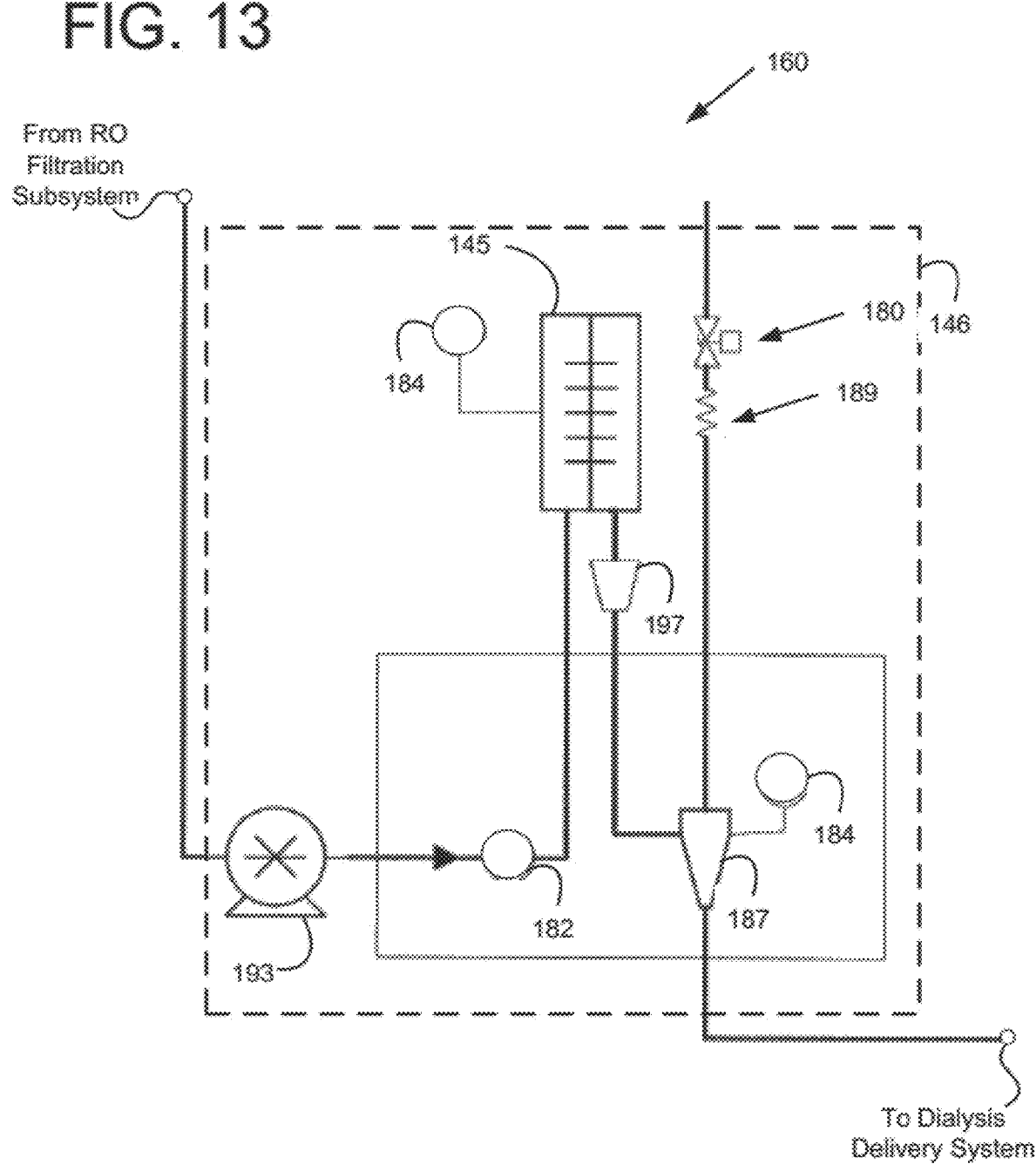
FIG. 13 illustrates one embodiment of a pasteurization subsystem of the water preparation system.

FIG. 13 illustrates one embodiment of a pasteurization subsystem 160 of the water preparation system. The pasteurization subsystem can be configured to minimize patient exposure to microbiological contamination by heating the fluid to eliminate microbiological contamination and endotoxins from the system. The pasteurization subsystem can include a heat exchanger (HEX) 145 configured to heat water to pasteurization temperature, allow the water to dwell at the high temperature, and then cool the water back to a safe temperature for the creation of dialysate.

In some embodiments, the HEX 145 can heat water received by the pasteurization subsystem to a temperature of approximately 148 degrees Celsius. The heated water can be held in a dwell chamber of the HEX for a time period sufficient to eliminate and kill bacteria and denature endotoxins. Endotoxins can be described as the carcasses of dead bacteria, characterized by long lipid chains. During water and dialysate preparation, endotoxins can be monitored along with bacteria to judge the purity of the dialysate. Endotoxins in dialysate can cause an undesirable inflammatory response in users. Therefore, it is desirable to minimize the levels of endotoxin in the dialysate. Endotoxins are not readily trapped by the pore size of typical ultrafilters. Instead, the endotoxins are stopped by ultrafilters through surface adsorption which can become saturated with endotoxins to the point that additional endotoxin will start to pass through. Heating endotoxins in superheated water to temperatures as low as 130 degrees C. have been demonstrated to denature endotoxins but the required dwell time is very long (many minutes). At these elevated temperatures, where the water remains in the liquid phase, water which is typically considered a polar solvent and begins to behave like a non-polar solvent to denature the lipid chains of the endotoxin. As the temperature increases to 220 degrees C. or higher, the denaturing of endotoxins occurs in seconds. The HEX of the present disclosure can run at 220 degrees C. or higher while maintaining a pressure (approximately 340 psi for 220 degrees C., but the HEX can withstand pressures of over 1000 psi) that keeps the water in liquid form. In one embodiment, a preferred temperature and pressure range of the HEX is 180-220 degrees C. and 145-340 psi. The water can then be cooled as it exits the dwell chamber. The HEX 145 is a self-contained counterflow heat exchanger that simultaneously heats incoming water and cools outgoing water to reduce energy consumption.

The pasteurization subsystem can include a HEX pump 193 configured to maintain a fluid pressure in the fluid line, to prevent the water from boiling. After the water passes through the HEX 145, a water regulator 197 can reduce the pressure of the water for use in the dialysis delivery system.

One or more pressure sensors 182 or temperature sensors 184 can be included for measuring pressure and temperature, respectively, of the water flowing through the pasteurization subsystem. Furthermore, an air separator 187 can further remove air and air bubbles from the water. In one embodiment, a flow restrictor 189 and valve 180 can be used to limit water dumped to the drain when the HEX 145 is heating up. Once the water has passed through the pasteurization subsystem, it has traveled through the entire water purification system and is clean and pure enough to be used in dialysate preparation and delivery by the dialysis delivery system.

Figure 28:
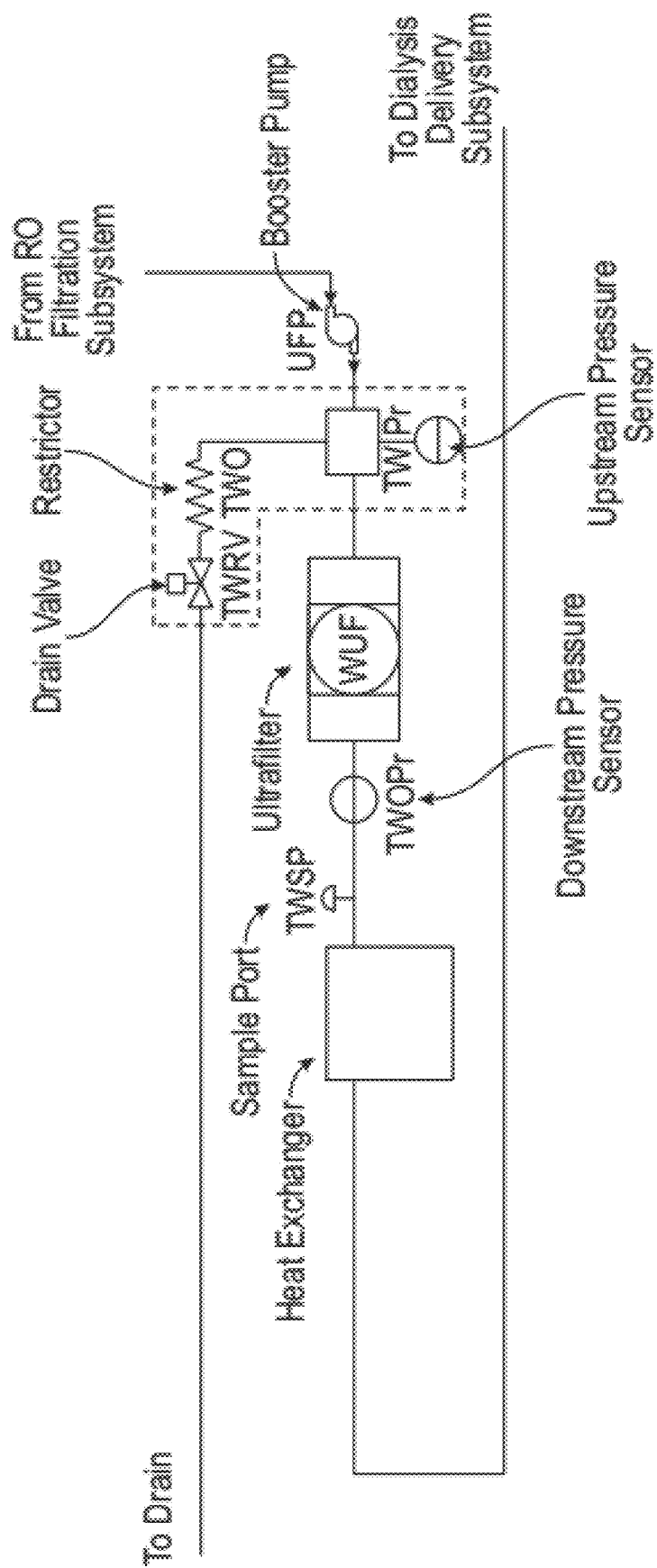
FIG. 28 is a schematic drawing of an ultrafiltration system that can be implemented in place of the pasteurization subsystem of FIG. 13.

FIG. 28 illustrates a different embodiment of an ultrafiltration subsystem that may be used in place of pasteurization subsystem of FIG. 13. This ultrafiltration subsystem uses a nanometer scale filter (ultrafilter) to remove microbiological contamination and endotoxins from the system. In some embodiments, the pore size of the ultrafilter is 5 nanometers. In some embodiments, the material of the ultrafilter is polysulfone, although the ultrafilter may comprise any material known in the art that may be fashioned into a filter structure of sufficient porosity. The ultrafiltration subsystem can include a booster pump to provide enough pressure to drive the flow of water through the ultrafilter. The pressure across the filter can be monitored by an upstream pressure sensor and a downstream pressure sensor, which can alert the user of the filter has been clogged and needs to be changed. Flow maybe diverted to drain through a drain valve and restrictor if needed. The ultrafiltration subsystem also comprises a sample port accessible from the exterior of the system for drawing water to confirm proper functionality of the ultrafilter. In some embodiments, the ultrafiltration subsystem may comprise flow through a heat exchanger to facilitate cooling or heating of fluid paths elsewhere in the system architecture.

Figure 14:
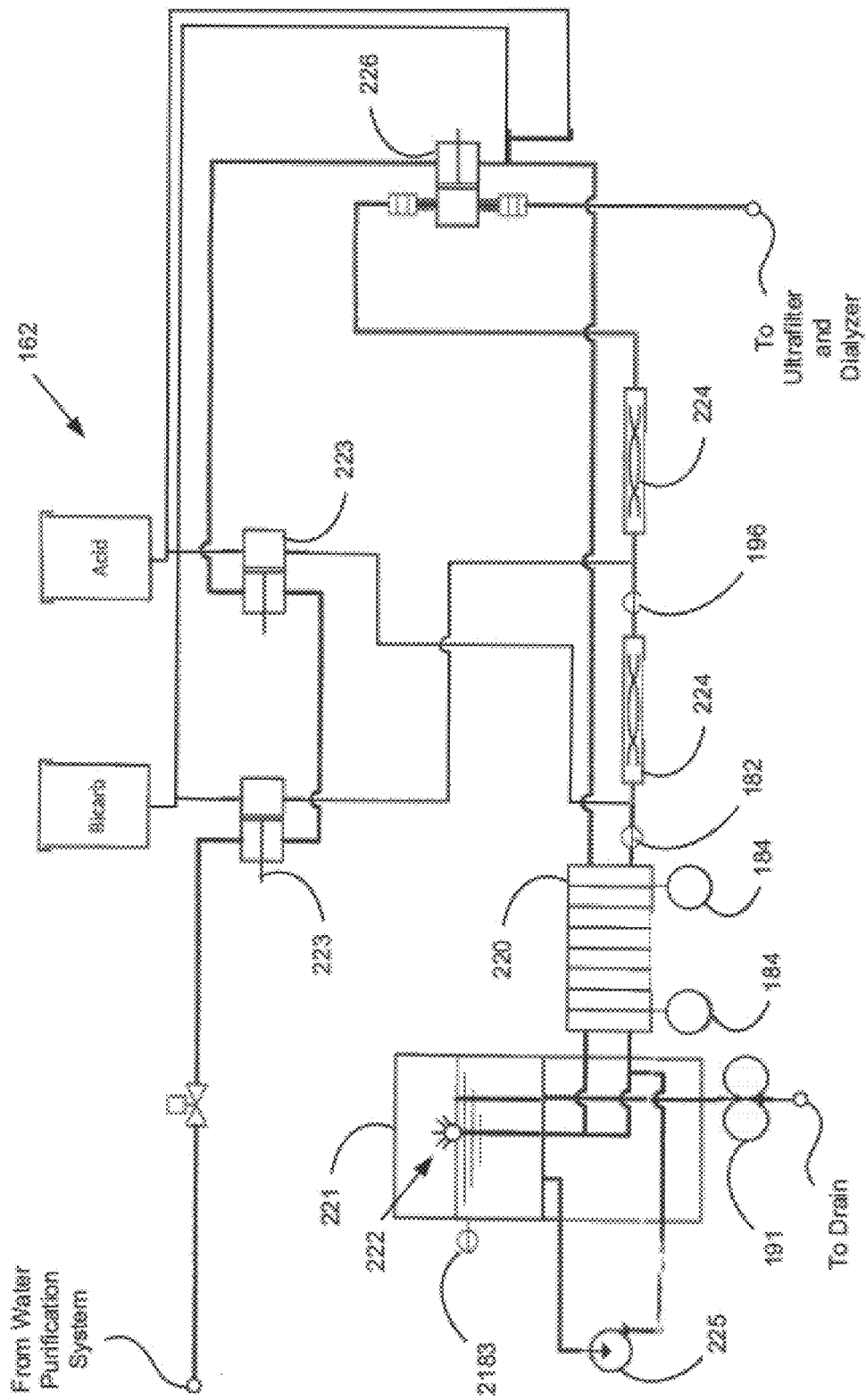
FIG. 14 illustrates a schematic of a mixing subsystem of the dialysis delivery system.

FIG. 14 illustrates a schematic of a mixing subsystem 162 of the dialysis delivery system. Purified water from the water purification system can be routed into the dialysis delivery system, where it can flow through heater 220 in preparation for final de-aeration in de-aeration chamber 221. In one embodiment, water flowing into the heater 220 can be approximately 43-47 degrees C., and the heater can heat the water up to 50 degrees C. or higher. The de-aeration chamber can be, for example, a spray chamber including a pump sprayer 222. During de-aeration, spray chamber recirculation pump 225 draws fluid at a high flow rate from the bottom of the de-aeration chamber. Heated water entering from the heater 220 then enters the de-aeration chamber above the fluid level through a pump sprayer 222. The temperature of the water as it enters and exits the heater can be monitored with temperature sensors 184. This restrictive spray head in combination with the high flow rate of the spray chamber recirculation pump 225 creates a vacuum in the de-aeration chamber ranging from −7 psig to −11 psig. The vacuum pressure and heat combine to effectively de-aerate the incoming water. As air collects in the top of the de-aeration chamber and the water level drops below level sensor 2183, the degas pump 191 can turn on or run faster to remove the collected air from the top of the de-aeration chamber. The degas pump 191 can remove a combination of air and liquid from the de-aeration chamber.

Figure 15:
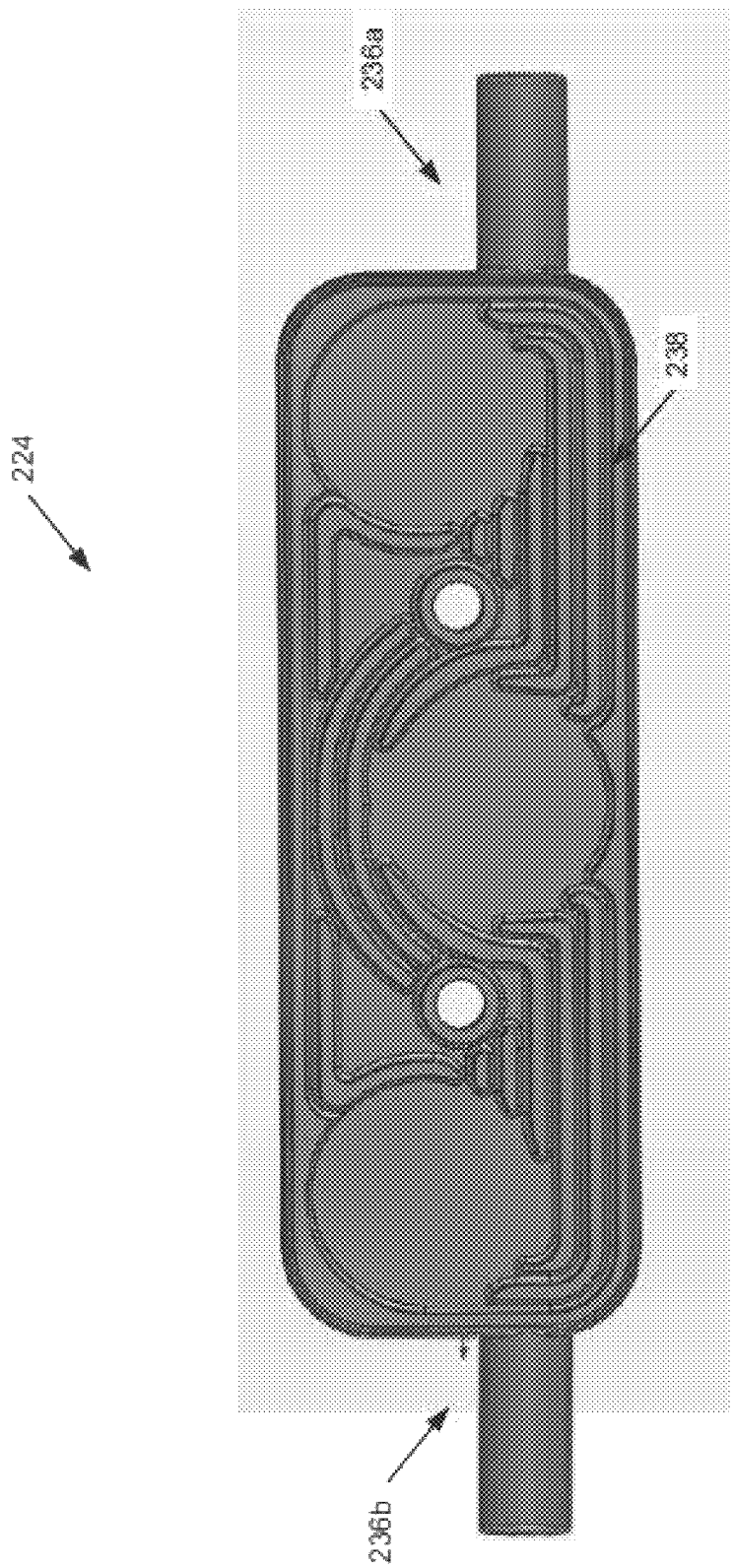
FIG. 15 shows one embodiment of a mixing chamber.

After de-aeration and subsequent cooling with the heater 220 to approximately body temperature, acid and bicarbonate concentrates can be volumetrically proportioned into the fluid path by way of concentrate pumps 223 in order to reach the desired dialysate composition. The water and concentrates can be mixed in a series of mixing chambers 224 that utilize a time delay or volumetric mixing instead of in-line mixing to smooth the introduction of fluids. FIG. 15 shows one embodiment of a mixing chamber 224, which can include an inlet portion 236*a* and an outlet portion 236*b*. The mixing chamber can include a plurality of channels 238 connecting the inlet portion to the outlet portion. The channels can be arranged so that some of the channels include longer paths from the inlet portion to the outlet portion than other channels. Thus, fluid traveling through the channels of the mixing chamber can be separated and divided along the varying channel lengths before being recombined to achieve more complete mixing of "lumpy" incoming fluid by the time it exits the mixing chamber.

Smart Flow

During dialysis therapy, the user has the ability to change the dialysate flow rate from the dialysis system to suit the patient's prescription. Oftentimes, this setting is toggled once at the beginning of the treatment, and the flow rate is held throughout the entire treatment. Dialysis providers typically set the maximum dialysate flow rate to maximize the waste clearances, although studies show that clearance rates witness diminishing returns at higher flow rates. As most dialysis machines run on a central water loop, with central dialysis concentrates, there is typically little incentive to conserve dialysate during treatment.

The dialysis system of the present disclosure is unique as it uses a finite volume of concentrates to proportion dialysate on-the-fly, as described above. In one embodiment, the dialysis system of the present disclosure can conserve dialysate concentrate by actively monitoring the amount of dialysate used during therapy and modulating the dialysate flow rate to lower the consumption of acid and bicarbonate concentrates. The ratio of pressures across the dialyzer (e.g., patient venous pressure, dialysate pressure, etc.) can be automatically maintained by the dialysis system while the dialysate flow is lowered, ensuring the appropriate ultrafiltration profile.

Depending on treatment goal, running at a lower dialysate flow rate may be appropriate. For example, running a longer treatment at lower dialysate and blood flow rates has a gentler physiological effect on the body, and may be appropriate for patients dialyzing at night or who have compromised physiology. The onboard monitoring of dialysate consumption, and real-time dialysate flow rate control, allows for laissez faire dialysis treatments while retaining appropriate device efficiency.

Figure 20:
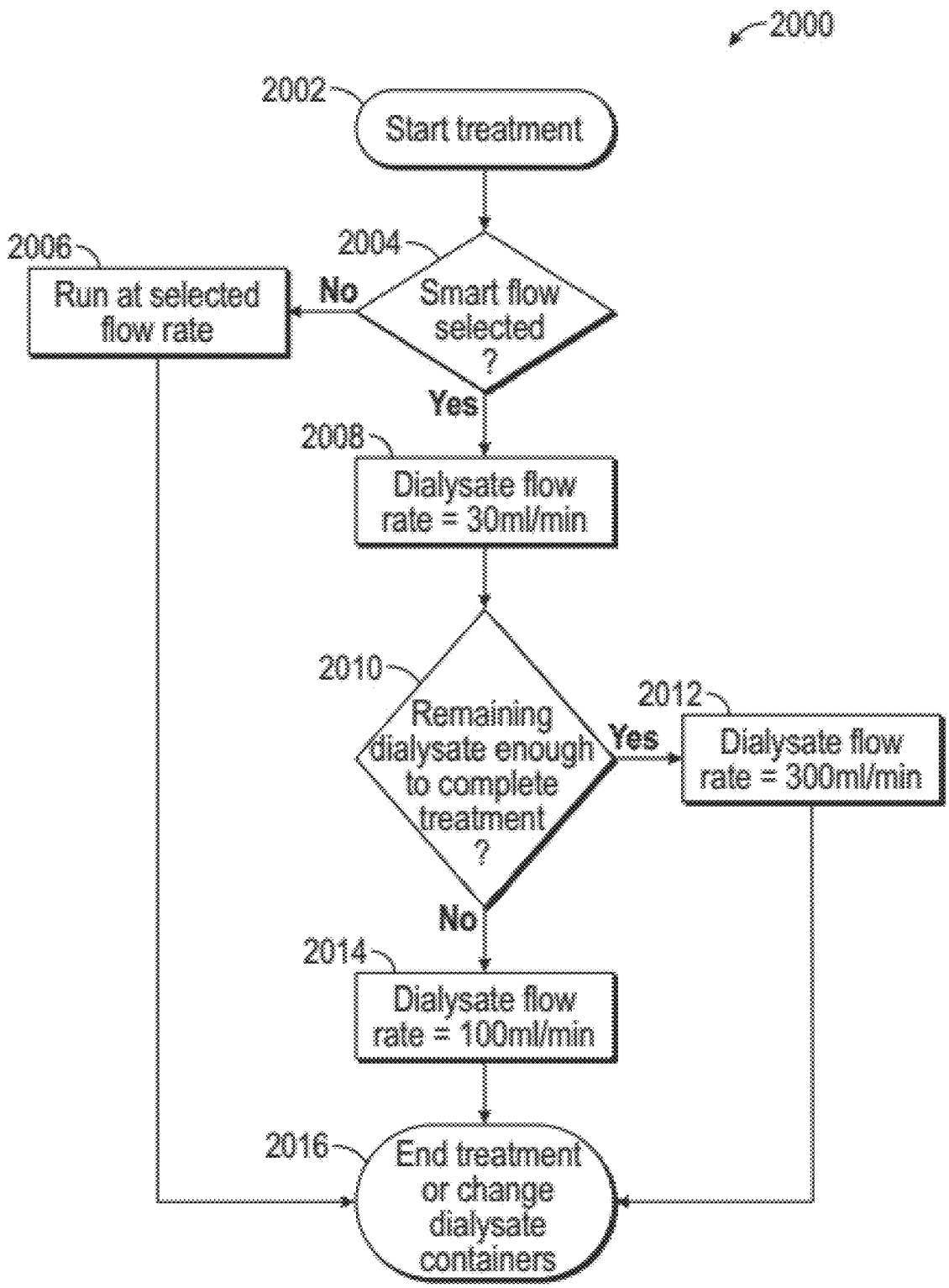
FIG. 20 is a flowchart describing an example of a method for conserving dialysate during therapy.

FIG. 20 is a flowchart 2000 showing one example of a method of monitoring dialysate consumption during therapy and adjusting dialysate flow rates to conserve dialysate. At step 2002 of flowchart 2000, a dialysis treatment can be started with the dialysis system. At step 2004 of flowchart 2000, the dialysis system can include an option to run a "smartflow" configuration in which the dialysis system monitors dialysis consumption during therapy. If smartflow is not selected, or is turned off, then the treatment or therapy runs as normal at the selected dialysate flow rate for the course of the treatment, shown by step 2006 of flowchart 2000.

If, however, the "smartflow" option is enabled at step 2004, then at step 2008 of flowchart 2000 the treatment can initially begin at a selected dialysate flow rate (e.g., 300 ml/min). The dialysis system can monitor dialysate consumption in real-time, and at step 2010 of flowchart 2000, the dialysis system can calculate and determine if the amount of remaining dialysate (or dialysate concentrates) are enough to complete the scheduled treatment. Step 2010 can be performed constantly during treatment, or can be performed and repeated at scheduled intervals during the therapy (e.g., every 30 seconds, every minute, every 5 minutes, etc.).

If there is enough dialysate remaining to complete the treatment at step 2010, then at step 2012 the dialysis system can complete the treatment at the original dialysate flow rate (e.g., 300 ml/min). If, however, there is not enough dialysate to complete the treatment, then at step 2014 of flowchart 2000, the dialysate flow rate can be reduced to a flow rate that permits completion of treatment with the amount of dialysate on hand (e.g., a flow rate of 100 ml/min). The dialysis system can be configured to maintain a pressure within the dialysis system when the flow rate is reduced. The therapy can continue at the flow rates of steps 2006, 2012, or 2014 until completion of the treatment at step 2016.

The smartflow calculations of the dialysis system are determined by comparing the potential dialysate remaining in the concentrate bottles to the dialysate consumed by a single dialysis treatment. As the dialysis system operates from dialysate concentrates of fixed volume, the dialysis system can, in real-time, calculate the amount of concentrates consumed and adjust the dialysate flow rate accordingly to conserve concentrate fluids. The calculation of dialysate used versus dialysate remaining is determined as following:

The total dialysate needed for a treatment is calculated by multiplying the sum of the concentrate and water flow rates by the total treatment time.

Total Dialysate Needed=(Acid Flow Rate+Bicarb Flow Rate+Water Flow Rate)*Total Treatment Time    (eq. 1)

Typically, bicarbonate concentrate is the limiting factor, as it has a higher consumption rate than acid concentrate. As such, the total dialysate available in any given treatment is dependent on bicarbonate volume and flow rate:

Amount of Available Time For Bicarbonate=Total Bicarb Volume/Bicarb Flow Rate    (eq. 2)

Dialysate Available=Dialysate Flow Rate*Amount of Available Time For Bicarbonate    (eq. 3)

The amount of dialysate consumed during a treatment is calculated real-time.

Dialysate Used=Dialysate Flow Rate*Elapsed Time in Treatment    (eq. 4)

From here, the dialysis system actively calculates the dialysate flow rate necessary to completely deplete the concentrates, thus completing the treatment without user intervention.

Time Remaining in Treatment=Total Treatment Time−Elapsed Time in Treatment    (eq. 5)

Dialysate Flow Rate Necessary=(Dialysate Available−Dialysate Used)/Time Remaining in Treatment    (eq. 6)

The Dialysate Flow Rate Necessary (eq. 6) for treatment completion will drop from the initial flow rate over the course of a treatment. If the calculated Dialysate Flow Rate Necessary falls to a predetermined set point, the system will immediately modulate the flow rate to the appropriate, lower, dialysate flow rate in order to complete the treatment.

In one embodiment, the concentrate pumps can run at an elevated rate to push out any air bubbles in the pumping mechanism (e.g., can run at upwards of 30 ml/min compared to ~7 ml/min during normal operation). Once the dialysate is mixed, a dialysate pump 226 can control the flow of dialysate through the dialysis delivery system. The mixing subsystem 162 can include various pressure sensors 182, temperature sensors 184, and conductivity sensors 196 to monitor the fluid during the dialysate preparation. The conductivity sensors can be used to measure the fluid ionic properties to confirm that the composition is correct.

The flow path within the dialysate delivery system can include one or more bypass or circulation routes that permit circulation of cleaning and/or sterilization fluid through the flow path. The circulation route may be an open flow loop wherein fluid flowing through the circulation route can be dischargeable from the system after use. In another embodiment, the circulation route may be a closed flow loop wherein fluid flowing through the circulation route is not dischargeable from the system.

A method of providing dialysis therapy to a patient is provided, comprising combining a dialysate concentrate and water with a dialysis system to produce a dialysate on-demand, providing a first flow of the dialysate through the dialysis system at a first dialysate flow rate, monitoring consumption of the dialysate concentrate by the dialysis system, determining if enough dialysate concentrate remains to complete the dialysis therapy at the first dialysate flow rate, and if there is not enough dialysate concentrate to complete the dialysis therapy at the first dialysate flow rate, calculating a second dialysate flow rate that allows for completion of the dialysis therapy, and providing a second flow of the dialysate through the dialysis system at the second dialysate flow rate.

In some examples, the dialysis system houses a finite supply of dialysate concentrate. In another example, the second dialysate flow rate is lower than the first dialysate flow rate. In one example, the first dialysis flow rate is approximately 300 ml/min, and the second dialysis flow rate is approximately 100 ml/min.

In one example, the determining step further comprises determining if enough dialysate concentrate remains based on the first dialysate flow rate, an amount of dialysate concentrate remaining, and a total treatment time. In one example, the method further includes maintaining a pressure within the dialysis system when the second flow of dialysate is provided.

Figure 16:
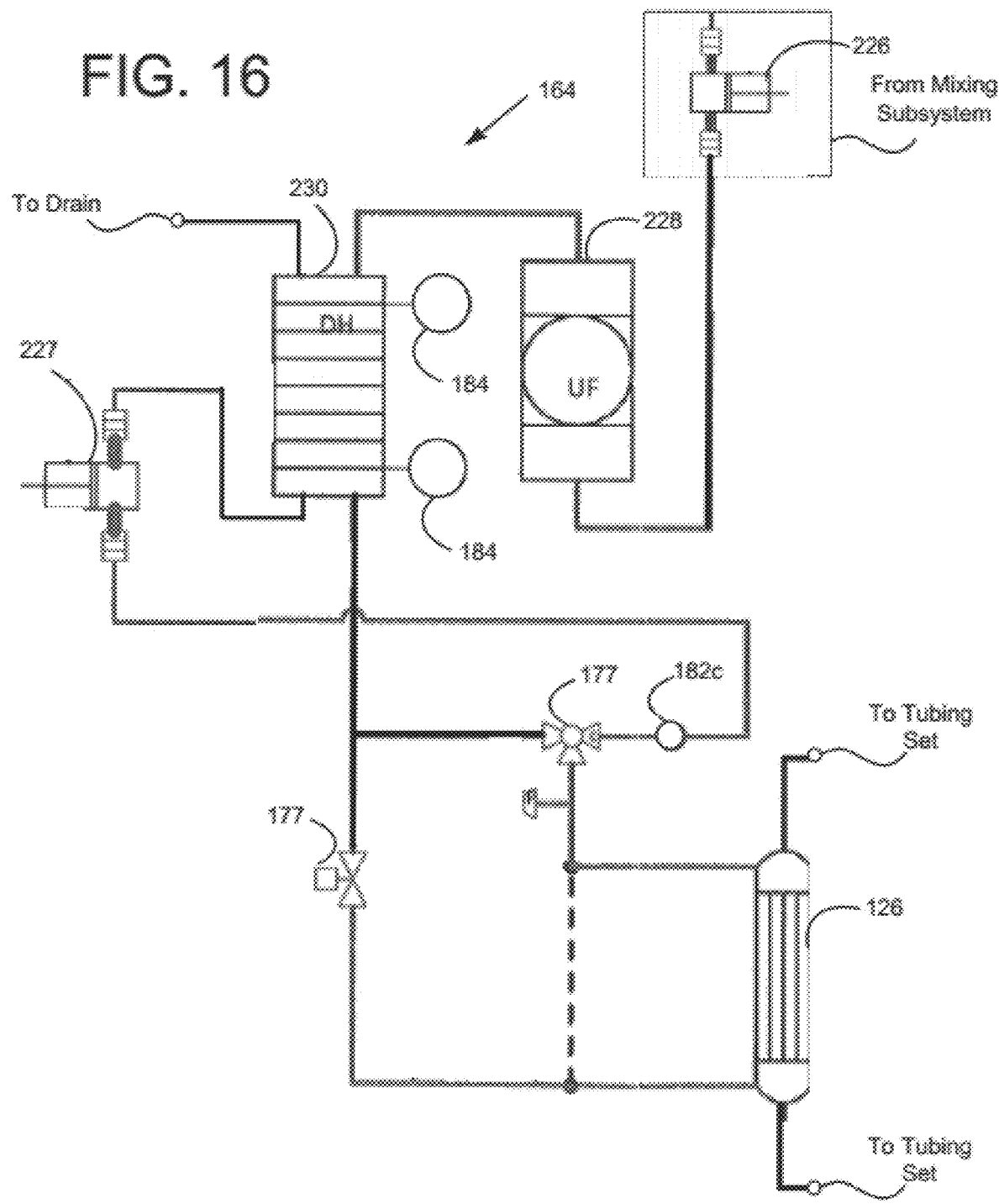
FIG. 16 illustrates an ultrafiltration subsystem of the dialysis delivery system which can receive the prepared dialysate from the mixing subsystem.

FIG. 16 illustrates an ultrafiltration subsystem 164 of the dialysis delivery system which can receive the prepared dialysate from the mixing subsystem. The ultrafiltration subsystem is configured to receive prepared dialysate from the mixing subsystem 162. Dialysate pump 226 and used dialysate pump 227 can be operated to control the flow of dialysate through the ultrafiltration subsystem. The pumps 226 and 227 can control the flow of dialysate to pass through an ultrafilter 228 and a dialysate heater 230 before entering dialyzer 126. Temperature sensors 184 can measure the temperature of the dialysate before and after passing through the dialysate heater 230. The dialysate heater can be user configurable to heat the dialysate based on the user's preference, typically between 35-39 degrees C. After passing through the dialyzer, the used dialysate can flow through a used dialysate pump 230 and back through the dialysate heater 228 before returning to drain. In one embodiment, the degas pump from FIG. 14 can be used to wet the back of the used dialysate pump 227. The ultrafiltration subsystem can include one or more actuators or valves 177 that can be controlled to allow dialysate to pass through the dialyzer 126, or alternatively, to prevent dialysate from passing through the dialyzer in a "bypass mode". A pressure sensor 182c disposed between the dialysate pump 226 and the used dialysate pump 227 can be configured to measure a pressure of the dialysate between the pumps when dialysate is prevented from passing through the dialyzer in the "bypass mode".

Figure 17:
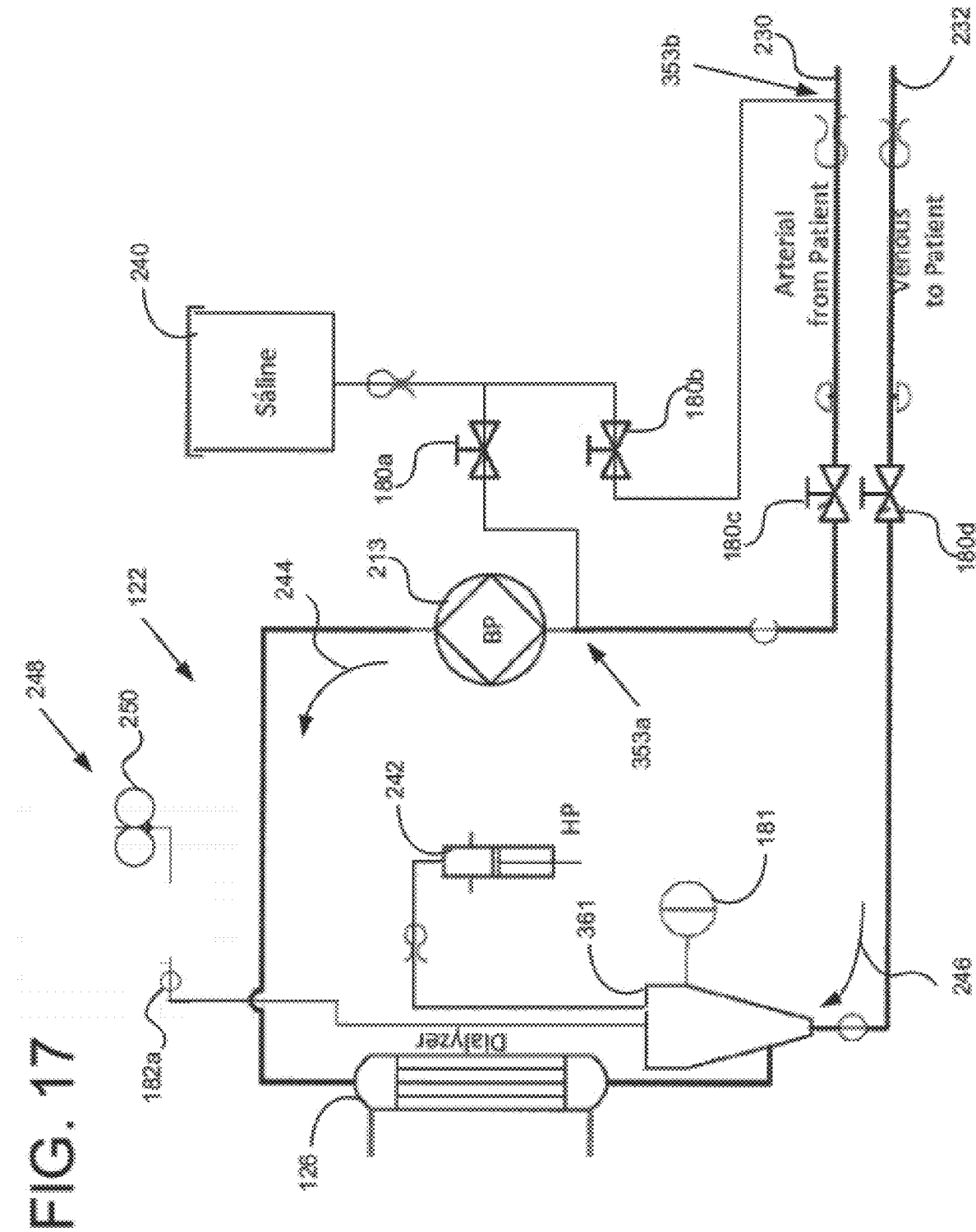
FIG. 17 shows a schematic diagram illustrating the flow of saline through tubing set during blood return to the user.

FIG. 17 illustrates a blood circuit subsystem 166 which is configured to pull blood from the patient and create a flow of blood through the dialyzer during dialysis therapy to pass fluid from the blood-side of the dialyzer to the dialysate-side of the dialyzer or vice versa. As described above, the blood circuit subsystem 166 can include, among other features described herein, the tubing set 122, blood pump 213, pinch valves 180a-d, venous drip chamber 361, venous level sensor(s) 181, arterial line 230, and venous line 232, saline source 240, and infusion pump 242. The blood pump 213 can be controlled to operate in first and second modes of operation. During dialysis therapy, the blood pump 213 can be operated in a first operating mode in which the pump pulls blood from the patient through arterial line 230, flows through the tubing set in the direction of arrow 244, flows through the dialyzer 126, flows through the venous drip chamber 361, and is returned to the patient through venous line 232. The blood pump can also be operated in a second operating mode in which the pump direction is reversed to cause fluid in the lines to flow in the direction of arrow 246 (for example, during a priming sequence as described above.

The blood circuit subsystem can also include a venting circuit 248 adapted to automatically control the fluid level in venous level chamber 361, as described above. The venting circuit can include a bi-directional peristaltic pump 250. The venous pressure sensor 182a of the system can also be located in the venting circuit 248. During dialysis therapy, the venous level sensor(s) 181 can monitor a fluid level of blood in the venous drip chamber 361. The electronic controller can receive the fluid level information from the sensor(s) and automatically maintaining the fluid level of the blood in the venous drip chamber by pumping or venting air out of the venous drip chamber with bi-directional peristaltic pump 250 and/or venting valves 252 if sensor(s) detect the fluid level dropping below a lower threshold, and by pumping air into the venous drip chamber with bi-directional peristaltic pump 250 if the sensor(s) detect the fluid level rising above an upper threshold.

Still referring to FIG. 17, a method of returning blood in the tubing set to the patient after dialysis therapy will be described. First, the user can clamp the line on their arterial needle (not shown in diagram) at the point where the arterial line 230 enters their body. This clamp can be located in between saline connection 353b and the user's body. The user can then confirm ACLMP is open, which is another clamp on the arterial line distal to the saline connection 353b. Next, the electronic controller of the dialysis system can open pinch valves 180b and 180c, and close pinch valve 180a. Next, the electronic controller can direct blood pump 213 to operate in the "forward direction" to draw saline from the saline source (e.g., a saline bag) into the arterial line 230 at saline connection 353b through pinch valve 180b, which is very close to where the arterial line connects to the patient. The blood pump can operate for a specified time, or can run until a predetermined volume of saline (e.g., 300-600 ml) is drawn into the tubing set, to return the blood in the tubing set and dialyzer into the patient through venous line 232. In some embodiments, the blood return process can be manually stopped based on the color of the saline in the tubing set (i.e., stopping the blood pump when the color of the saline becomes clear or a light-pink color).

The dialysate pump and used dialysate pump described above can be part of an electronic circuit in communication with the electronic controller of the dialysis system to achieve a controlled ultrafiltration rate, and can also be adjusted to precisely control the addition or removal of fluid to or from the patient.

The dialysate pump and used dialysate pump can be controlled with a high degree of precision to achieve dynamic balancing, periodic balancing, and continuous correction. Referring to FIGS. 16-17, dialysate pump 226 and used dialysate pump 227 can be configured to pump dialysate through the dialysis delivery system. The dialysate pump can be controlled to push the dialysate through the ultrafilter and the dialysate heater to get heated.

To calibrate the flow of the system, the system can be controlled to enter a bypass mode in which valves 177 are actuated to prevent dialysate flow through the dialyzer. This isolates the patient tubing set on the blood side of the dialyzer from the dialysate flow and creates a closed system for dialysate flow that will not allow ultrafiltration. Whenever the system is in bypass the used dialysate pump can be servoed to maintain constant pressure as measured by pressure sensor 182c, which is positioned between the dialysate pump 226 and used dialysate pump 227. The pump speed of the used dialysate can be adjusted while the pump speed of the dialysate pump is maintained at a constant speed until the pressure measured by pressure sensor 182c stabilizes. Once the pressure is stabilized, the pump speed of the used dialysate pump vs the pump speed of the dialysate pump can be recorded as the pump speed ratio that results in zero ultrafiltration. When the systems exits bypass and returns to dialysis therapy, the used dialysate pump speed can be adjusted based on the desired ultrafiltration rate.

When dialyzer is bypassed, pressure measurements of the dialysate can be made independent of influences or pressures from the blood-side of the dialyzer (e.g., isolated from the blood tubing set). When the dialysate and used dialysate pumps operate at the same rate there is no pressure change at pressure sensor 182c positioned between the two pumps, so there is no flow imbalance between the pumps. However, if the dialysate and used dialysate pumps operate at different rates then a flow imbalance is created between the pumps, and a pressure change representing this flow imbalance can be measured at pressure sensor 182c. In some embodiments, the flow imbalance can be controlled based on the pump strokes of the respective pumps. In other embodiments, the flow imbalance can be controlled based on lookup tables that determine the optimal pump speeds based on the measured venous pressure. The electronic controller of the system can be configured to automatically control the flow of fluid across the dialyzer (i.e., ultrafiltration) by adjusting a pump speed of the used dialysate pump 227 with respect to dialysate pump 226 (or alternatively, of the dialysate pump 226 with respect to used dialysate pump 227) to create a flow imbalance between the dialysate-side and blood-side of the dialyzer. When a flow imbalance is created on the dialysate-side of the dialyzer by operating the pumps 226 and 227 at different speeds, then fluid can flow across the dialyzer membranes from the blood-side to the dialysate-side, and vice versa, to equalize that flow imbalance.

The pump speeds of the dialysate pump 226 and used dialysate pump 227 can be locked in by the system based on a desired rate of ultrafiltration, and valve 180 can be opened for normal operation during dialysis therapy. During therapy, the system can continue to monitor venous pressure on user side at pressure sensor 182a. If the venous pressure changes (e.g., greater than 30 mm-Hg mercury in change), the system can be configured to automatically rebalance the pumps with the same technique described above. This allows the pumps to be balanced to achieve the desired amount of fluid transfer through the dialyzer, or alternatively, to achieve no fluid transfer through the dialyzer. In one specific embodiment, the system can detect changes in the venous pressure of the user and automatically adjust the speed of the used dialysate pump 227 based on a look-up table of speeds against venous pressure to maintain ultrafiltration balance in the user. Once the system has been calibrated, the used dialysate pump speed can be modulated to adjust the rate of fluid removal from the patient. In some embodiments, a pump speed of the used dialysate pump can be alternatively increased or decreased relative to the dialysate pump to enable hemodiafiltration (e.g., pushing/pulling fluid onto the patient).

In some embodiments, there are two phases of operation of the dialysate pump and the used dialysate pump. In the first phase of operation, the speed of the used dialysate pump is greater than the speed of the dialysate pump, resulting in net fluid flux from the blood side of the dialyzer and into the dialysate side of the dialyzer. The speed differential may be set such that fluid is removed from the patient's blood at a rate that is physiologically tolerable over a short duration, perhaps up to a rate of 100 mL/min. To achieve this, for example, the dialysate pump may be set to run at 300 mL/min, and the used dialysate pump may be set to run at 400 mL/min. In this phase, convective clearance of solutes is increased. However, because of a limited volume of fluid in the patient's circulation, indefinite application of this first phase of operation is not sustainable, as it would hemoconcentrate the blood in the dialyzer. In the second phase of operation, the speed of the dialysate pump is greater than the speed of the used dialysate pump, resulting in net fluid flux from the dialysate side of the dialyzer into the blood side of the dialyzer. In this second phase, at least some of the fluid removed from the patient's circulation during the first phase is replaced, allowing the first phase to be repeated. Convective clearance of solutes is reduced during the second phase, although diffusive clearance would still take place. Current systems that are used for hemodiafiltration typically inject replacement fluid into the patient's extracorporeal circuit directly, which requires extremely high standards for microbiological purity. These replacement fluids are typically pre-manufactured and provided in large bags, which are cumbersome to handle and add considerable cost. In the disclosed invention, the replacement fluid is produced on-line and is additionally filtered by the dialyzer before coming into contact with the patient's blood, obviating the need for pre-manufactured fluids and direct connections into the patient's extracorporeal circuit. In some embodiments, the duration and/or net fluid flux of the first phase of the second phase are equal. In some embodiments, the duration and/or net fluid flux of the first phase and the second phase are not equal. In further embodiments, the net fluid flux produced by the two phases sum up to equal the total fluid removal goal during the treatment. In further embodiments, the invention comprises a plurality of any number of operating phases with varying durations and/or net fluid fluxes, or a continuum thereof.

Pump Burn-In

The dialysis system described herein includes a number of pumps, including pumps that may interact directly with fluids such as dialysate, saline, or blood that are delivered to the patient. A vane pump can include internal graphite components whereas the gear pump can include of PEEK materials which shed off during normal pump operations. These particles may enter components such as filters or regulators of the dialysis system which may result in premature failures. By design, vane pumps and gear pumps operate under a positive displacement principle, where internal pump components will grind against one another to move fluid. As such, surface imperfections on the internal pump components will continue to shed over use. Under high temperature and/or pressure conditions, the stress on the internal pump components will increase, thereby increasing the amount of shedding observed. This disclosure provides a vane and gear pump burn in process designed to reduce particulate shedding amounts during dialysis system operation.

The intent of a burn-in process is to remove loose particulates present in the pumps by running the pumps at elevated temperatures and/or elevated pressures during the first few hours of the pumps lifetime. For example, the process can include running the pumps at temperatures and/or pressures that are higher than the temperatures and pressures that the pumps will encounter during normal operation. In running these pumps in an extreme condition, the surface imperfections on the internal pump will be sanded down, thus making a more flush interface between components. Smooth to smooth surface contact on internal vanes and gears yields fewer particulates shed, thereby preventing premature failure of other components in the system. In one example, running these pumps at 70 deg C and 100 psi for 8 hours maximizes the amount of infant shedding, thus leading to reduced shedding during normal operation modes (25 deg C and 100 psi).

Figure 21:
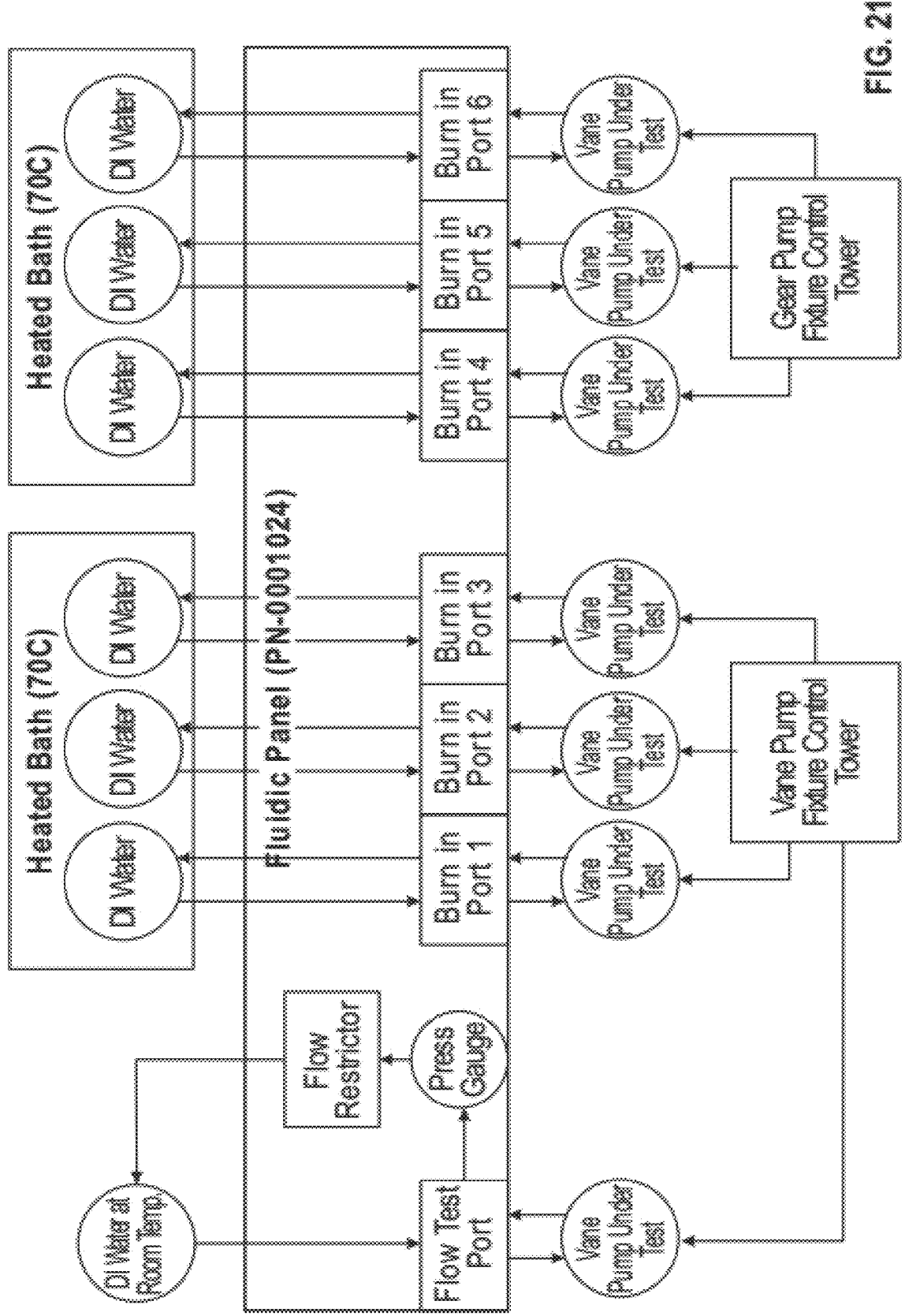
FIGS. 21, 22, 23, 24 and 25 show an example of a pump burn-in system to prevent particulates from the pumps from entering the dialysis system.

FIG. 21 illustrates a fluidic schematic of a pump burn-in fixture. The pump burn-in fixture can be used to burn in vane and/or gear pumps to remove loose particulates prior to installing the pumps in a dialysis system. Several vane pumps and gear pumps may be run in parallel in the pump burn-in fixture. In one embodiment, the fixture can include a computer running an embedded program to control the pumps. In another embodiment, the burn-in fixture may be controlled by a voltage control potentiometer. The pump burn-in fixture can form a closed-loop fluidic path with one or more pumps under test when the pumps are connected to the pump burn-in fixture. In some embodiments, the pump burn-in fixture can include one or more heating elements configured to heat a fluid within the pump burn-in fixture to temperatures higher than what the pumps are exposed to during normal operation. For example, the heating elements can be configured to heat a fluid within the pump burn-in fixture to temperatures up to and including 100 deg C. In one example, a preferred temperature for the fluid within the pump burn-in fixture is 70 deg C.

Figure 22:
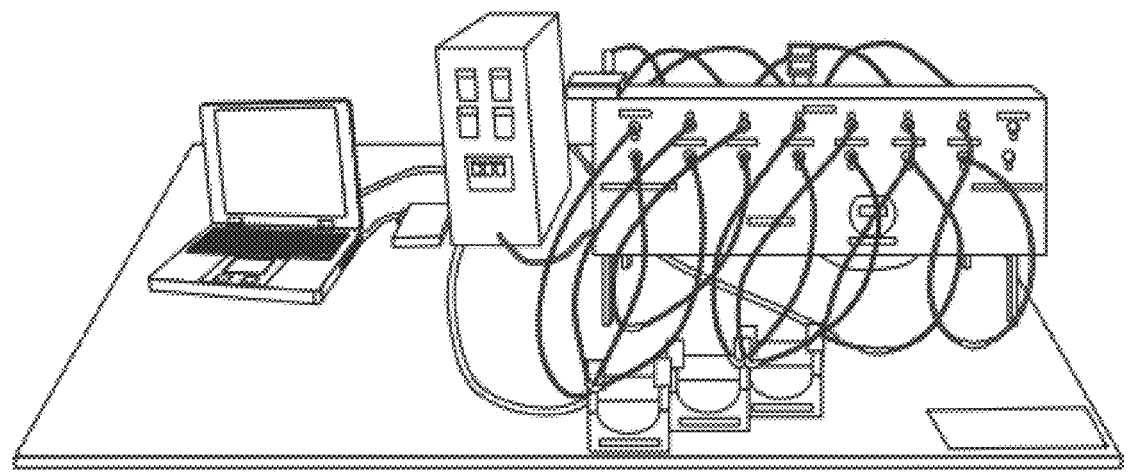
Figure 24:
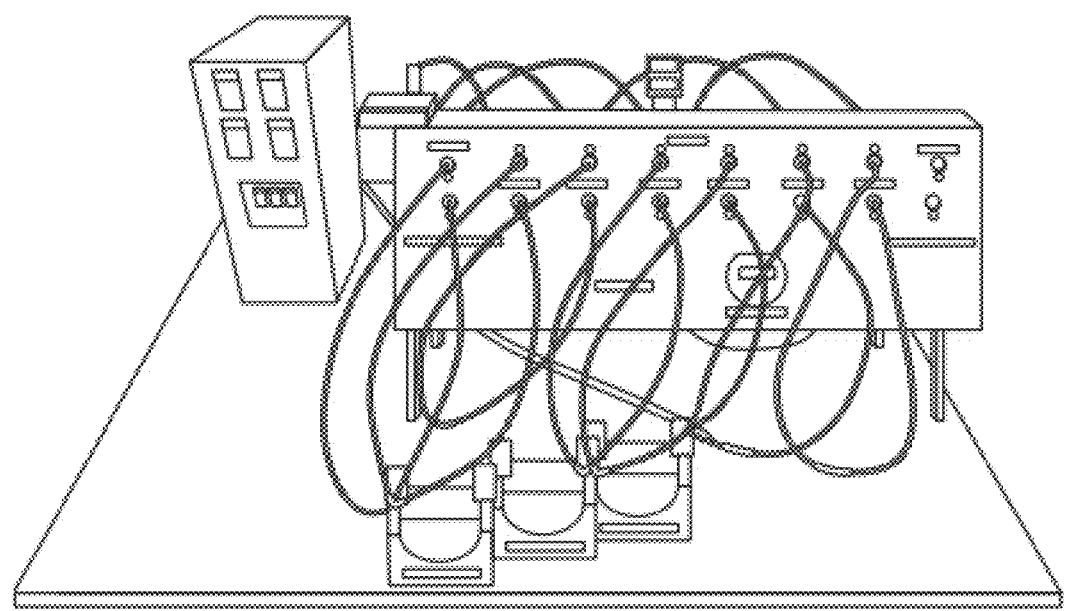

FIGS. 22 and 24 are pictures of the pump burn-in fixture from FIG. 21, including the closed-loop fluidic path between the pumps and the fixture. FIG. 22 also illustrates a computer or electronic controller (e.g., a laptop) controlling the software which controls operation of the pump burn-in fixture.

Figure 23:
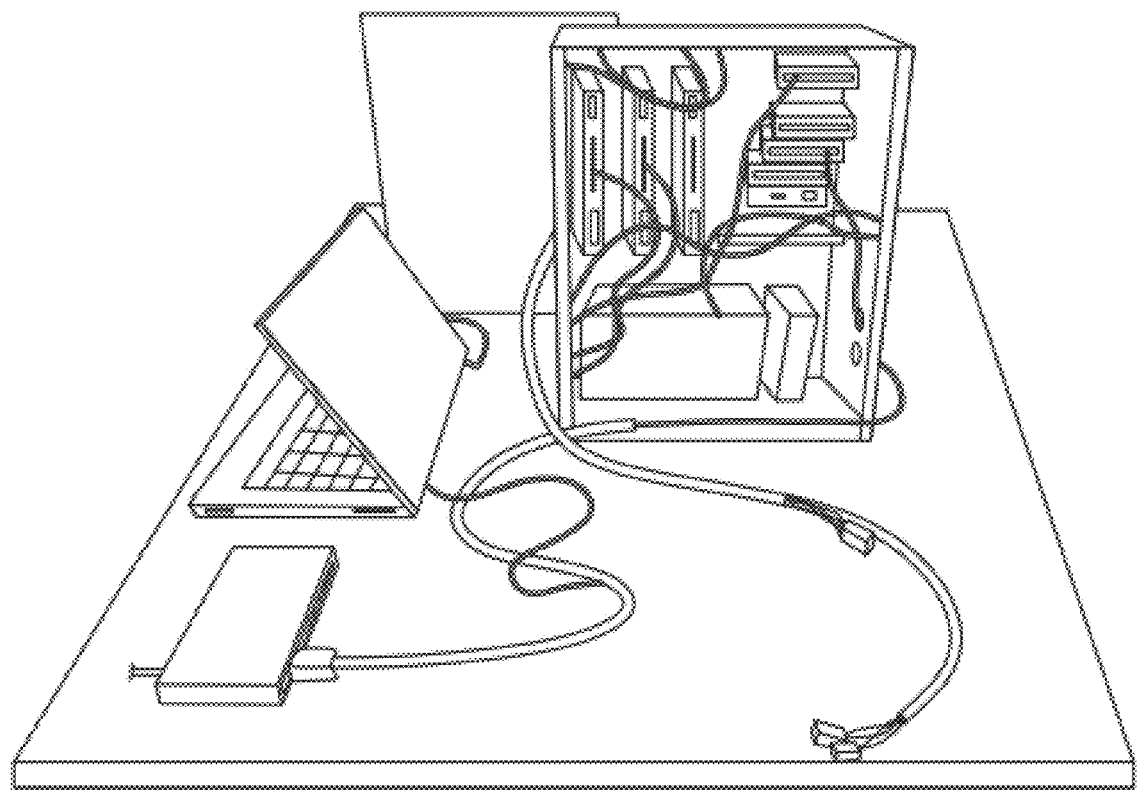
Figure 25:
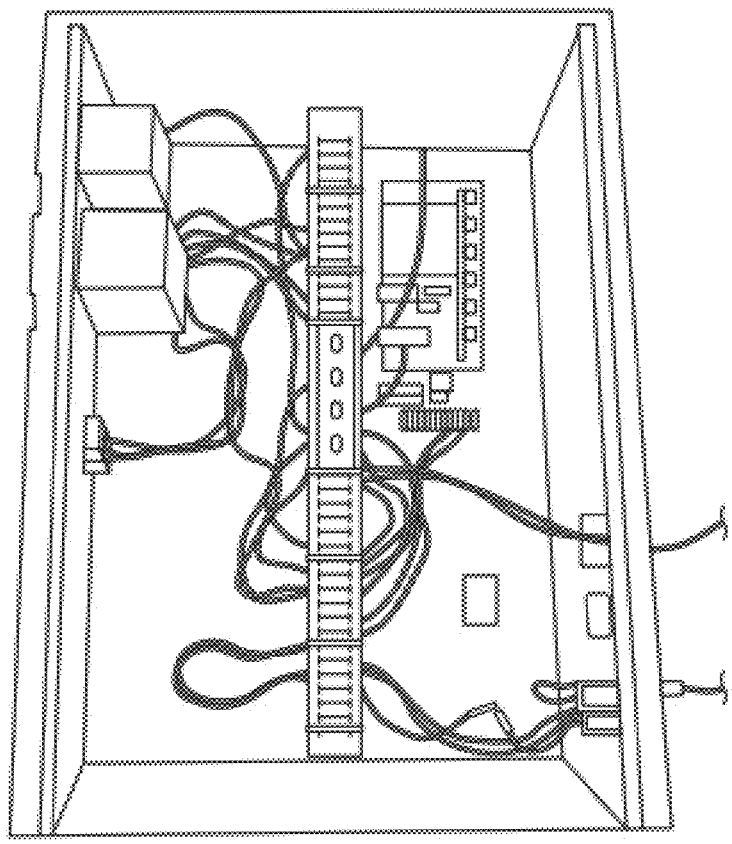

FIGS. 23 and 25 are pictures showing additional electronics that drive the burn-in fixture, including a power supply that can toggle 24 VDC and 48 VDC, and provide power to the microcontrollers and motor drivers to actuate the pumps.

A method of improving durability and operation of one or more displacement pumps, can comprise connecting one or more displacement pumps to a pump burn-in fixture to form a closed-loop fluidic path between the one or more displacement pumps and the pump burn-in fixture, increasing a temperature and pressure of fluid within the closed-loop fluidic path, and operating the one or more displacement pumps to flow the fluid through the closed-loop fluidic path for a predetermined period of time to reduce surface imperfections internal to the one or more displacement pumps.

In some embodiments, the increasing step further comprises increasing the temperature and pressure of the fluid to levels that are above what the one or more displacement pumps encounter during normal operation. For example, this can include increasing the temperature of the fluid above 25 deg C. In another example, the method can include increasing the pressure of the fluid above 100 psi.

As described above, the water purification system and the dialysate delivery system can both include a variety of pumps, valves, sensors, air separators, air sensors, heat exchangers, and other safety features. All of these features can be controlled electronically and automatically by the electronic controller of the dialysis system.

Automated Conductivity Calibration

The dialysis system described herein includes a number of conductivity sensors to monitor the quality of the incoming water, the effectiveness of the water purification system and to ensure proper proportioning of the dialysate fluid generated. As with many sensors, it can necessary to perform periodic re-calibration of these sensors to ensure accuracy. Typically, each conductivity sensor is calibrated in isolation, where the fluid connections to the rest of the system on either side of the sensor are broken, and then re-connected to a source of conductivity calibration fluid and a calibrated external conductivity meter. This conductivity calibration fluid which has a known conductivity, is passed through the sensor, and additionally verified by the external conductivity meter, which verifies that the sensor under test is properly calibrated, or allows for adjustment of its calibration constants if it is out of calibration. The type of calibration fluid used may be different for each sensor, as the conductivity range it is meant to read could be different from other conductivity sensors in the system. Disclosed herein is a method to perform automated calibration of all the conductivity sensors within the system that does not require breaking the fluidic path. In some embodiments, the automatic conductivity calibration method comprises connecting a calibration fluid concentrate to the acid or bicarbonate pumps. Optionally, an external conductivity meter may be connected to the fluidic circuit of the system, for example using the inlet and outlet connectors that are used to connect to a dialyzer. Using the proportioning pumps, the system will mix the calibration fluid concentrate and purified water produced by the water purification module to produce a calibration fluid of a nominally known conductivity. In this state, the fluidic path of the system is a single-pass flow through, where the mixed fluid is sent to drain. Once the conductivity of the mixed calibration fluid has stabilized, the proportioning pump(s) can be stopped, and the fluidic path of the system is automatically reconfigured to recirculate the fluid instead of sending it to drain. The recirculation path of the system can be configured to include all the conductivity sensors within the system, including the optional external conductivity meter, which will now all be exposed to the same recirculating fluid. Measurements from any or all of the conductivity sensors can then be compared with other sensors, including the optional external conductivity sensor, and calibration constants may be adjusted as needed. In some embodiments, the this process can be automatically repeated multiple times, with different mixing ratios of calibration fluid producing final mixed fluids of different conductivities. As such a multi-point calibration curve can be generated. Furthermore, conductivity sensors in different portions of the fluid path typically sense fluids of different conductivity ranges. The calibration fluid can be sequentially proportioned to cover the different typical operating ranges of the different conductivity sensors. Calibration of the each of the conductivity sensors can be more heavily weighted, or done exclusively, with calibration fluid representative of its native operating range.

What is claimed is:

1. A method of priming a tubing set and a dialyzer of a dialysis system, comprising the steps of:
    connecting an arterial line of a tubing set to a venous line of the tubing set to form a continuous loop in the tubing set;
    pumping air out of the tubing set with an air pump;
    pulling a flow of fluid from a fluid source into the tubing set with the air pump;
    operating a blood pump of the dialysis system in a forward operating mode to flow fluid from the fluid source into the tubing set in a first direction; and
    operating the blood pump in a reverse operating mode to flow fluid through the tubing set in a second direction opposite to the first direction.

2. The method of claim 1, wherein the pulling step further comprises pulling the fluid into the tubing set with the air pump until the fluid is detected by a first level sensor in a venous drip chamber.

3. The method of claim 2, wherein operating the blood pump in the forward operating mode further comprises operating the blood pump in a forward operating mode to flow fluid from the fluid source into the tubing set until the fluid is detected by a second level sensor in the venous drip chamber.

4. The method of claim 2, further comprising, after the pulling step, allowing a fluid level in the venous drip chamber to fall below the first level sensor.

5. The method of claim 4, wherein operating the blood pump in the forward operating mode further comprises operating the blood pump in a forward operating mode to flow fluid from the fluid source into the tubing set until the fluid is detected by the first level sensor in the venous drip chamber.

\* \* \* \* \*